US011306355B2

United States Patent
Song et al.

(10) Patent No.: US 11,306,355 B2
(45) Date of Patent: *Apr. 19, 2022

(54) BISULFITE-FREE, BASE-RESOLUTION IDENTIFICATION OF CYTOSINE MODIFICATIONS

(71) Applicant: Ludwig Institute for Cancer Research Ltd, Zurich (CH)

(72) Inventors: Chunxiao Song, Oxford (GB); Yibin Liu, Oxford (GB)

(73) Assignee: Ludwig Institute for Cancer Research Ltd, Zurich (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/201,825

(22) Filed: Mar. 15, 2021

(65) Prior Publication Data

US 2021/0317519 A1    Oct. 14, 2021

Related U.S. Application Data

(63) Continuation of application No. 16/960,510, filed as application No. PCT/US2019/012627 on Jan. 8, 2019.

(60) Provisional application No. 62/771,409, filed on Nov. 26, 2018, provisional application No. 62/660,523, filed on Apr. 20, 2018, provisional application No. 62/614,798, filed on Jan. 8, 2018.

(51) Int. Cl.

| C12Q 1/6869 | (2018.01) |
| C12P 17/16 | (2006.01) |
| C12Q 1/6844 | (2018.01) |
| C12Q 1/6874 | (2018.01) |
| C12Q 1/6876 | (2018.01) |

(52) U.S. Cl.
CPC ............ *C12Q 1/6869* (2013.01); *C12P 17/16* (2013.01); *C12Q 1/6844* (2013.01); *C12Q 1/6874* (2013.01); *C12Q 1/6876* (2013.01); *C12Q 2600/154* (2013.01); *C12Y 204/01026* (2013.01); *C12Y 204/01027* (2013.01)

(58) Field of Classification Search
None
See application file for complete search history.

(56) References Cited

U.S. PATENT DOCUMENTS

| 7,582,420 B2 | 9/2009 | Oliphant et al. |
| 8,741,567 B2 | 6/2014 | He et al. |
| 9,267,117 B2 | 2/2016 | Guan et al. |
| 2014/0127678 A1 | 5/2014 | Guan et al. |
| 2014/0322707 A1 | 10/2014 | He et al. |
| 2017/0176421 A1 | 6/2017 | Rao et al. |
| 2017/0253924 A1 | 9/2017 | Lu et al. |
| 2018/0251815 A1 | 9/2018 | Okamoto et al. |
| 2020/0024643 A1 | 1/2020 | Arensdorf et al. |
| 2020/0370114 A1 | 11/2020 | Song et al. |

FOREIGN PATENT DOCUMENTS

| EP | 2694686 B1 | 11/2017 |
| WO | WO 2013/017853 | 2/2013 |
| WO | WO 2014/074450 | 5/2014 |
| WO | WO 2014/165770 | 10/2014 |
| WO | WO 2015/021282 | 2/2015 |
| WO | WO 2017/039002 | 3/2017 |
| WO | WO 2017/176630 | 10/2017 |
| WO | WO 2019/136413 | 7/2019 |

OTHER PUBLICATIONS

Zuo et al. Nucleic Acids Res. (1995) 23(16): 3239-3243 (Year: 1995).*
Ponnaluri et al. Biochem. Biophys. Res. Comm. (2013) 436: 115-120 (Year: 2013).*
Chaurasia et al. Biochem: An Indian Journal (2012) 6(7): 237-242 (Year: 2012).*
Liu et al. Nature Chem. Biol. (2017) 13: 181-187 (Year: 2017).*
Aparici-Espert, I. et al., A Combined Experimental and Theoretical Approach to the Photogeneration of 5,6-Dihydropyrimidin-5-yl Radicals in Nonaqueous Medica, J. Org. Chem. 81(10):4031-4038 (2016), with supporting information.
Booth, M.J., et al., Quantitative Sequencing of 5-Methylcytosine and 5-Hydroxymethylcytosine at Single-Base Resolution, Science, 336(6083):934-937, (2012).
E.P. Consortium, An integrated encyclopedia of DNA elements in the human genome, Nature 489(7414):57-74, (2012).
Holmes, E.E., et al. Performance Evaluation of Kits for Bisulfite-Conversion of DNA from Tissues, Cell Lines, FFPE Tissues, Aspirates, Lavages, Effusions, Plasma, Serum, and Urine, PLoS One, 9(4):1-15:e93933 (2014).
International Search Report, PCT/US1019/012627, ISA/US, 5 pages, dated May 7, 2019.
Krueger F. and Andrews R., Bismark: a flexible aligner and methylation caller for bisulfite-seq applications, Bioinformatics, 27(11):1571-1572, (2011).
Li, H., and Durbin, R., Fast and accurate short read alignment with Burrows-Wheeler transform, Bioinformatics, 25(5):1754-1760 (2009).
Liu, Y. et al., Bisulfite-Free, Base-Resolution, and Quantitative Sequencing of Cytosine Modifications, bioRxiv, pp. 1-18, (2018). entire document.
Lu, X. et al., Chemical Modification-Assisted Bisulfite Sequencing (CAB-Seq) for 5-Carboxylcytosine Detection in DNA, J Am Chem Soc, 135(25):9315-9317, (2013). entire document.
Matsushita, T., et al., DNA-friendly Cu (ii)/TEMPO-catalyzed 5-hydroxymethylcytosine-specific oxidation, Chemical Communications, 53(42):5756-5759, (2017).
Pais, J. E. et al., Biochemical Characterization of a Naegleria TET-Like Oxygenase and its Application in Single Molecule Sequencing of 5-Methylcytosine, Proceedings of the National Academy of Sciences, 112(14):4316-4321, (2015). entire document.

(Continued)

*Primary Examiner* — Susan M Hanley
(74) *Attorney, Agent, or Firm* — Casimir Jones S.C.; J. Mitchell Jones

(57) ABSTRACT

This disclosure provides methods for bisulfite-free identification in a nucleic acid sequence of the locations of 5-methylcytosine, 5-hydroxymethylcytosine, 5-carboxylcytosine and 5-formylcytosine.

14 Claims, 29 Drawing Sheets

Specification includes a Sequence Listing.

(56) References Cited

OTHER PUBLICATIONS

Quinlan, A.R. and Hall, I.M., BEDTools: a flexible suite of utilities for comparing genomic features, Bioinformatics 26(6):841-842 (2010).
Robinson, J.T., et al., Integrative genomics viewer, Nat. Biotechnol, 29(1):24-26, (2011).
Schüler, Peter and Miller, Aubry K., Sequencing the Sixth Base (5-Hydroxymethylcytosine): Selective DNA Oxidation Enables Base-Pair Resolution, Angewandte Chemie International Edition, 51(43): 10704-10707 (2012). entire document.
Song, C.X. et al., Genome-wide Profiling of 5-Formylcytosine Reveals Its Roles in Epigenetic Priming, Cell, 153(3):678-691, (2013). entire document.
Wen, L., et al., Whole-genome analysis of 5-hydroxymethylcytosine and 5-methylcytosine at base resolution in the human brain, Genome Biology 15(3):R49, (2014).
Written Opinion, PCT/US2019/012627, ISA/US, 12 pages, dated May 7, 2019.
Xia, B., et al., Bisulfite-free, base-resolution analysis of 5-formylcytosine at the genome scale, Nat. Methods, 12(11)1047-1050 (2015).
Yu, M., et al., Base-resolution analysis of 5-hydroxymethylcytosine in the mammalian genome. Cell 149:1368-1380, (2012).
Zhu, C., et al., Single-Cell 5-Formylcytosine Landscapes of Mammalian Early Embryos and ESCs at Single-Base Resolution, Cell Stem Cell, 20:720-731, (2017).
Song et al., "Selective chemical labeling reveals the genome-wide distribution of 5-hydroxymethylcytosine" Nat Biotechnol. Jan. 2011 ; 29(1): 68-72.
Ambrogelly et al., Screening of Reducing Agents for the PEGylation of Recombinant Human IL-10, Protein J (2013) 32:337-342.

International Search Report and Written Opinion, PCT/US2019/017902, dated Apr. 11, 2019, 6 pages.
Yu, Miao et al. "Tet-assisted bisulfite sequencing of 5-hydroxymethylcytosine" Nature Protocols, vol. 7, No. 12, Nov. 29, 2012, pp. 2159-2170.
Liu, Yibin et al. "Bisulfite-free direct detection of 5-methylcytosine and 5-hydroxymethylcytosine at base resolution", Nature Biotechnology, 37, 2019, pp. 424-429.
Nestor, Colm E. et al. "Tissue type is a major modifier of the 5-hydroxymethylcytosine content of human genes", Gnome Research, vol. 22; Cold Spring Harbor Laboratory Press, Sep. 6, 2016, pp. 467-477.
Roberston, Adam B. et al. "A novel method for the efficient and selective identification of 5-hydroxymethylcytosine in genomic DNA", Nucleic Acids Research, vol. 39, No. 8, Feb. 7, 2011, pp. 1-10.
Ruhaak, L. Renee et al. "2-Picoline-borane: A non-toxic reducing agent for oligosaccharide labeling by reductive amination" Proteomics, vol. 10, Mar. 24, 2010, pp. 2330-2336.
Song, Chunxiao, "Bisulfite-free, base resolution, and quantitative identification of cytosine modifications", Keystone Symposia Conference, DNA & RNA Methylation, Ludwig Institute for Cancer Research, University of Oxford, Jan. 24, 2018, pp. 1-23.
Tahiliani, Mamta, et al., "Conversion of 5-Methylcytosine to 5-Hydroxymethylcytosine in Mammalian DNA by MML Partner TET1", Science vol. 324, 930, May 15, 2009, pp. 930-935.
Song C. et al. 5-Hydroxymethylcytosine signatures in cell-free DNA provide information about tumor types and stages, Cell Research (2017) :1-12.
Iyer, L. et al. Comparative genomics of transcription factors and chromatin proteins in parasitic protists and other eukaryotes, Int J Parasitol. Jan. 2008;38(1):1-31.

* cited by examiner

FIG. 1
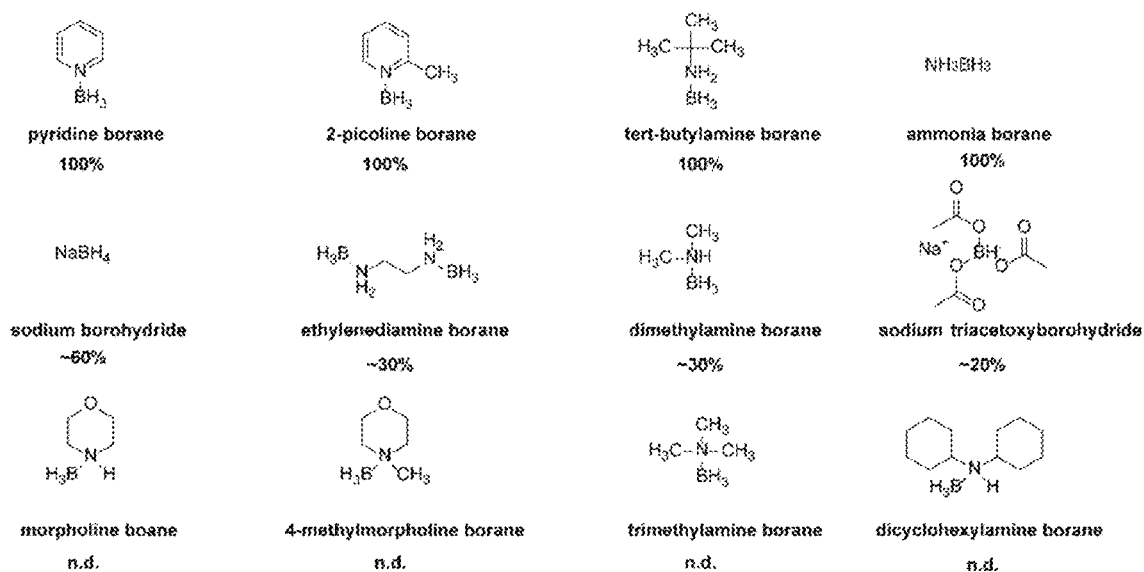
FIG. 2A
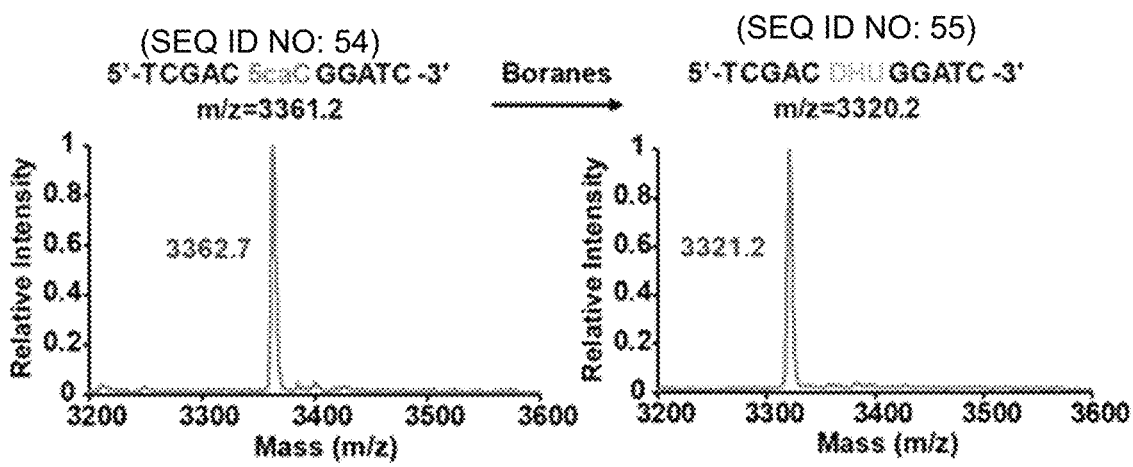
FIG. 2B
| Cytosine modification in Oligo | Conversion to DHU |
|---|---|
| C | 0% |
| 5mC | 0% |
| 5hmC | 0% |
| 5fC | 97.6±0.1% |
| 5caC | 98.1±0.6% |

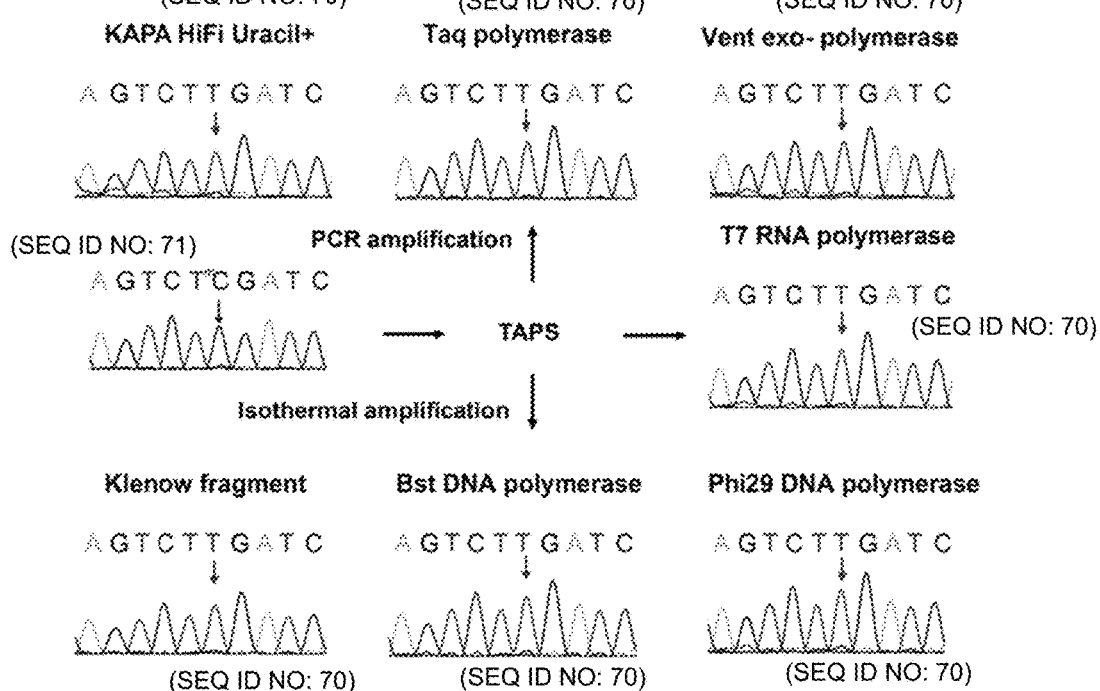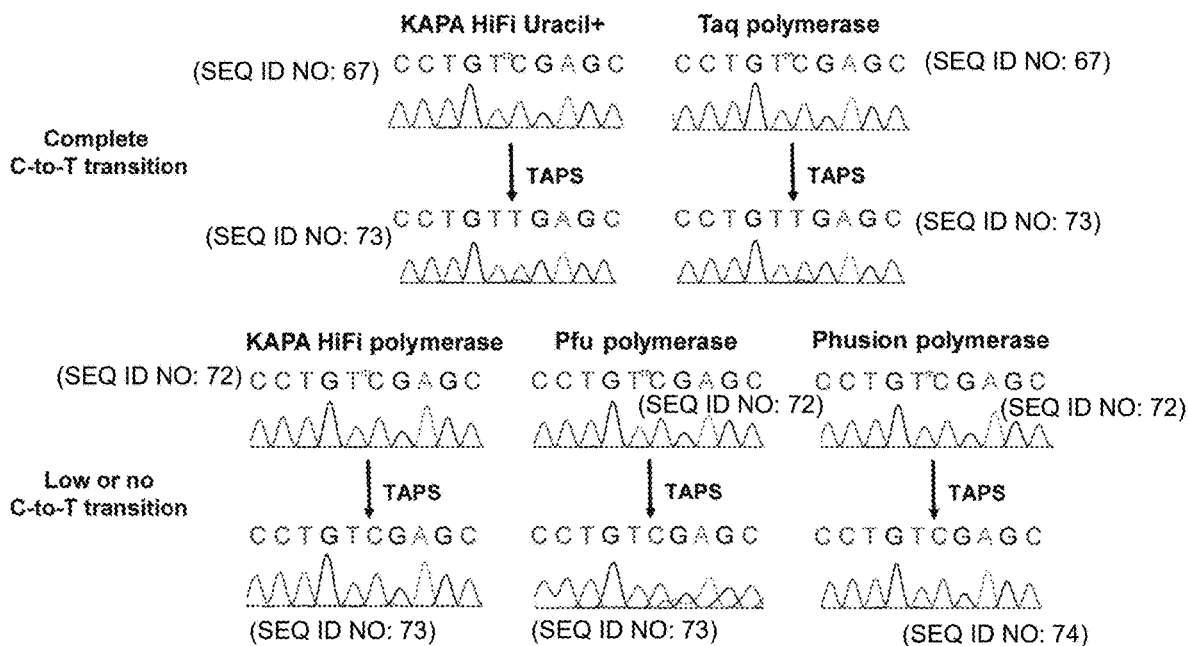

FIG. 19A
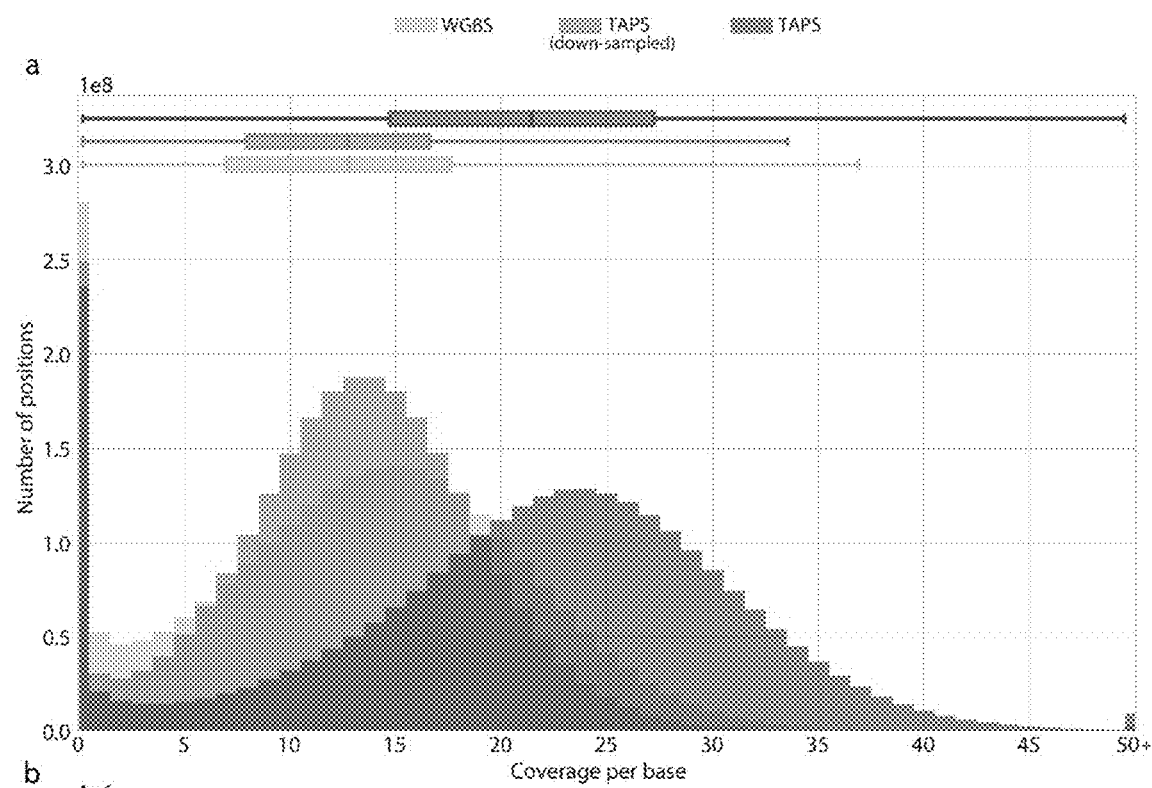
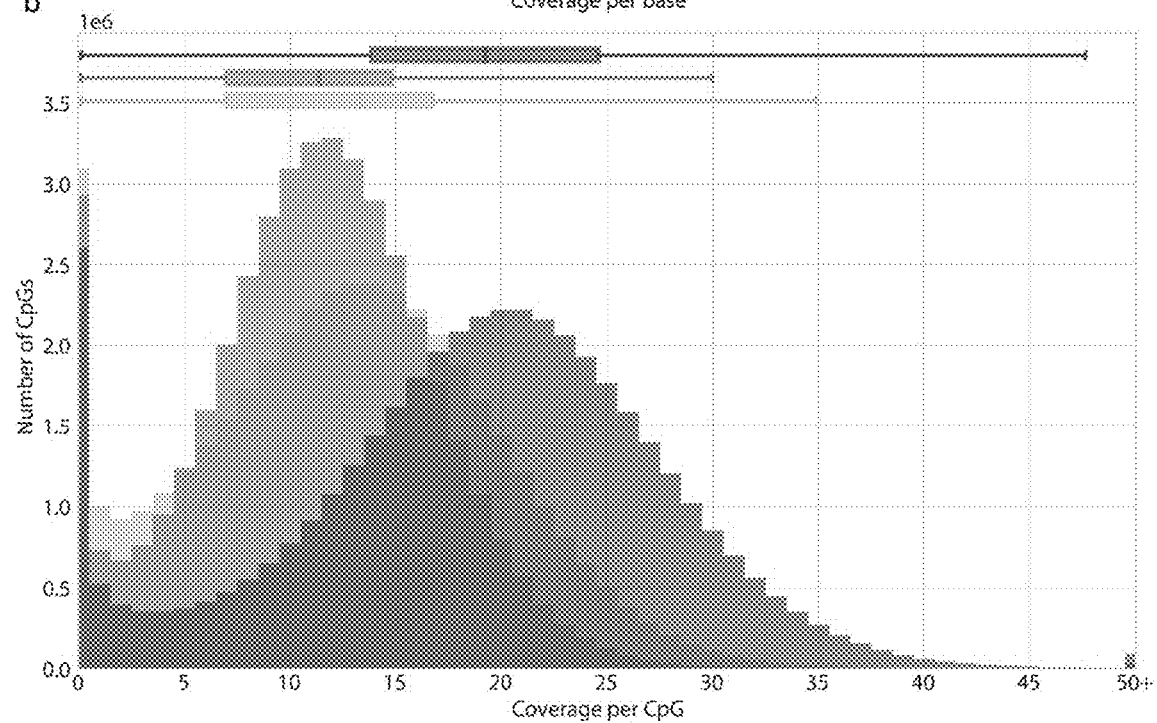
FIG. 19B

SEQUENCE LISTING

<160> NUMBER OF SEQ ID NOS: 84

<210> SEQ ID NO 1
<211> LENGTH: 12
<212> TYPE: DNA
<213> ORGANISM: Artificial Sequence
<220> FEATURE:
<223> OTHER INFORMATION: Primer

<400> SEQUENCE: 1
gtcgaccgga tc                                                        12

<210> SEQ ID NO 2
<211> LENGTH: 17
<212> TYPE: DNA
<213> ORGANISM: Artificial Sequence
<220> FEATURE:
<223> OTHER INFORMATION: Primer

<400> SEQUENCE: 2
ttggatccgg tcgactt                                                   17

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
cctgatgaaa caagcatgtc                                                20

<210> SEQ ID NO 4
<211> LENGTH: 20
<212> TYPE: DNA
<213> ORGANISM: Artificial Sequence
<220> FEATURE:

<223> OTHER INFORMATION: Primer

<400> SEQUENCE: 4
cautactcac utccccacut                                           20

<210> SEQ ID NO 5
<211> LENGTH: 36
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n=methylcytosine
<220> FEATURE:
<221> NAME/KEY: misc_feature
<222> LOCATION: (29)..(29)
<223> OTHER INFORMATION: n = hydroxymethylcytosine

<400> SEQUENCE: 5
cccgangcat gatctgtact tgatcgacng tgcaac                         36

<210> SEQ ID NO 6
<211> LENGTH: 58
<212> TYPE: DNA
<213> ORGANISM: Artificial Sequence
<220> FEATURE:
<223> OTHER INFORMATION: Primer

<400> SEQUENCE: 6
aatgatacgg cgaccaccga gatctacact ctttccctac acgacgctct tccgatct   58

<210> SEQ ID NO 7
<211> LENGTH: 64
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: n = phosphorylation

<400> SEQUENCE: 7
ngatcggaag agcacacgtc tgaactccag tcacgccaat atctcgtatg ccgtcttctg   60
cttg                                                            64

<210> SEQ ID NO 8
<211> LENGTH: 56
<212> TYPE: DNA
<213> ORGANISM: Artificial Sequence
<220> FEATURE:
<223> OTHER INFORMATION: Primer

<400> SEQUENCE: 8
tcttccgauc gttgcacggu cgatcaagua cagatcatgc gucgggagau cggaag     56

<210> SEQ ID NO 9
<211> LENGTH: 157
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (64)..(64)
<223> OTHER INFORMATION: n = methylcytosine

```
<220> FEATURE:
<221> NAME/KEY: misc_feature
<222> LOCATION: (87)..(87)
<223> OTHER INFORMATION: n = hydroxymethylcytosine

<400> SEQUENCE: 9
aatgatacgg cgaccaccga gatctacact ctttccctac acgacgctct tccgatctcc    60
cgangcatga tctgtacttg atcgacngtg caacgatcgg aagagcacac gtctgaactc   120
cagtcacgcc aatatctcgt atgccgtctt ctgcttg                            157

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
aatgatacgg cgaccaccga g                                              21

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
caagcagaag acggcatacg ag                                             22

<210> SEQ ID NO 12
<211> LENGTH: 34
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (9)..(9)
<223> OTHER INFORMATION: n = methylcytosine
<220> FEATURE:
<221> NAME/KEY: misc_feature
<222> LOCATION: (19)..(19)
<223> OTHER INFORMATION: n = methylcytosine
<220> FEATURE:
<221> NAME/KEY: misc_feature
<222> LOCATION: (27)..(27)
<223> OTHER INFORMATION: n = methylcytosine

<400> SEQUENCE: 12
agcagtctng atcagctgnt actgtangta gcat                                34

<210> SEQ ID NO 13
<211> LENGTH: 58
<212> TYPE: DNA
<213> ORGANISM: Artificial Sequence
<220> FEATURE:
<223> OTHER INFORMATION: Primer

<400> SEQUENCE: 13
aatgatacgg cgaccaccga gatctacact ctttccctac acgacgctct tccgatct     58

<210> SEQ ID NO 14
<211> LENGTH: 64
<212> TYPE: DNA
<213> ORGANISM: Artificial Sequence
<220> FEATURE:
```

<223> OTHER INFORMATION: Primer
<220> FEATURE:
<221> NAME/KEY: misc_feature
<222> LOCATION: (1)..(1)
<223> OTHER INFORMATION: n = phosphorylation

<400> SEQUENCE: 14
ngatcggaag agcacacgtc tgaactccag tcacgccaat atctcgtatg ccgtcttctg    60
cttg    64

<210> SEQ ID NO 15
<211> LENGTH: 41
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: n = phosphorylation

<400> SEQUENCE: 15
naggtgcgct aagttctaga tcgccaactg gttgtggcct t    41

<210> SEQ ID NO 16
<211> LENGTH: 61
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: n = phosphorylation

<400> SEQUENCE: 16
nctatagccg gcttgctctc tctgcctcta gcagctgctc cctatagtga gtcgtattaa    60
c    61

<210> SEQ ID NO 17
<211> LENGTH: 40
<212> TYPE: DNA
<213> ORGANISM: Artificial Sequence
<220> FEATURE:
<223> OTHER INFORMATION: Primer

<400> SEQUENCE: 17
atctagaact tagcgcacct agatcggaag agcgtcgtgt    40

<210> SEQ ID NO 18
<211> LENGTH: 74
<212> TYPE: DNA
<213> ORGANISM: Artificial Sequence
<220> FEATURE:
<223> OTHER INFORMATION: Primer

<400> SEQUENCE: 18
agagagcaag ccggctatag atgctacgta cagtagcagc tgatcaagac tgctaaggcc    60
acaaccagtt ggcg    74

<210> SEQ ID NO 19
<211> LENGTH: 42
<212> TYPE: DNA
<213> ORGANISM: Artificial Sequence
<220> FEATURE:
<223> OTHER INFORMATION: Primer

<400> SEQUENCE: 19
agacgtgtgc tcttccgatc gttaatacga ctcactatag gg                          42

<210> SEQ ID NO 20
<211> LENGTH: 255
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (107)..(107)
<223> OTHER INFORMATION: n = methylcytosine
<220> FEATURE:
<221> NAME/KEY: misc_feature
<222> LOCATION: (117)..(117)
<223> OTHER INFORMATION: n = methylcytosine
<220> FEATURE:
<221> NAME/KEY: misc_feature
<222> LOCATION: (125)..(125)
<223> OTHER INFORMATION: n = methylcytosine

<400> SEQUENCE: 20
aatgatacgg cgaccaccga gatctacact ctttccctac acgacgctct tccgatctag      60
gtgcgctaag ttctagatcg ccaactggtt gtggccttag cagtctngat cagctgntac     120
tgtangtagc atctatagcc ggcttgctct ctctgcctct agcagctgct ccctatagtg     180
agtcgtatta acgatcggaa gagcacacgt ctgaactcca gtcacgccaa tatctcgtat     240
gccgtcttct gcttg                                                      255

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
tgctagaggc agagagagca ag                                              22

<210> SEQ ID NO 22
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (9)..(9)
<223> OTHER INFORMATION: n= DHU or U or T or C

<400> SEQUENCE: 22
agcagtctng atcagct                                                    17

<210> SEQ ID NO 23
<211> LENGTH: 17
<212> TYPE: DNA
<213> ORGANISM: Artificial Sequence
<220> FEATURE:
<223> OTHER INFORMATION: Primer

<400> SEQUENCE: 23
gctactgtac gtagcat                                                    17

<210> SEQ ID NO 24

```
<211> LENGTH: 58
<212> TYPE: DNA
<213> ORGANISM: Artificial Sequence
<220> FEATURE:
<223> OTHER INFORMATION: Primer

<400> SEQUENCE: 24
aatgatacgg cgaccaccga gatctacact ctttccctac acgacgctct tccgatct      58

<210> SEQ ID NO 25
<211> LENGTH: 64
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: n = phosphorylation

<400> SEQUENCE: 25
ngatcggaag agcacacgtc tgaactccag tcacgccaat atctcgtatg ccgtcttctg      60
cttg                                                                  64

<210> SEQ ID NO 26
<211> LENGTH: 41
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: n = phosphorylation

<400> SEQUENCE: 26
naggtgcgct aagttctaga tcgccaactg gttgtggcct t                         41

<210> SEQ ID NO 27
<211> LENGTH: 61
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: n = phosphorylation

<400> SEQUENCE: 27
nctatagccg gcttgctctc tctgcctcta gcagctgctc cctatagtga gtcgtattaa      60
c                                                                     61

<210> SEQ ID NO 28
<211> LENGTH: 40
<212> TYPE: DNA
<213> ORGANISM: Artificial Sequence
<220> FEATURE:
<223> OTHER INFORMATION: Primer

<400> SEQUENCE: 28
atctagaact tagcgcacct agatcggaag agcgtcgtgt                            40

<210> SEQ ID NO 29
<211> LENGTH: 74
<212> TYPE: DNA
<213> ORGANISM: Artificial Sequence
```

```
<220> FEATURE:
<223> OTHER INFORMATION: Primer

<400> SEQUENCE: 29
agagagcaag ccggctatag atgctacgta cagtagcagc tgatcaagac tgctaaggcc      60
acaaccagtt ggcg                                                       74

<210> SEQ ID NO 30
<211> LENGTH: 42
<212> TYPE: DNA
<213> ORGANISM: Artificial Sequence
<220> FEATURE:
<223> OTHER INFORMATION: Primer

<400> SEQUENCE: 30
agacgtgtgc tcttccgatc gttaatacga ctcactatag gg                        42

<210> SEQ ID NO 31
<211> LENGTH: 255
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (107)..(107)
<223> OTHER INFORMATION: n = DHU or U or T or C

<400> SEQUENCE: 31
aatgatacgg cgaccaccga gatctacact ctttccctac acgacgctct tccgatctag      60
gtgcgctaag ttctagatcg ccaactggtt gtggccttag cagtctngat cagctgctac     120
tgtacgtagc atctatagcc ggcttgctct ctctgcctct agcagctgct ccctatagtg     180
agtcgtatta acgatcggaa gagcacacgt ctgaactcca gtcacgccaa tatctcgtat     240
gccgtcttct gcttg                                                     255

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
cacagatgtc tgcctgttca                                                 20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
agggtggtga atgtgaaacc                                                 20

<210> SEQ ID NO 34
<211> LENGTH: 2018
<212> TYPE: DNA
<213> ORGANISM: Artificial Sequence
<220> FEATURE:
<223> OTHER INFORMATION: Primer

<400> SEQUENCE: 34
```

| | | | | |
|---|---|---|---|---|
| cacagatgtc | tgcctgttca | tccgcgtcca | gctcgttgag | tttctccaga agcgttaatg | 60 |
| tctggcttct | gataaagcgg | gccatgttaa | gggcggtttt | ttcctgtttg gtcactgatg | 120 |
| cctccgtgta | aggggatttt | ctgttcatgg | gggtaatgat | accgatgaaa cgagagagga | 180 |
| tgctcacgat | acgggttact | gatgatgaac | atgcccggtt | actggaacgt tgtgagggta | 240 |
| aacaactggc | ggtatggatg | cggcgggacc | agagaaaaat | cactcagggt caatgccagc | 300 |
| gcttcgttaa | tacagatgta | ggtgttccac | agggtagcca | gcagcatcct gcgatgcaga | 360 |
| tccggaacat | aatggtgcag | ggcgctgact | ccgcgtttc | cagactttac gaaacacgga | 420 |
| aaccgaagac | cattcatgtt | gttgctcagg | tcgcagacgt | tttgcagcag cagtcgcttc | 480 |
| acgttcgctc | gcgtatcggt | gattcattct | gctaaccagt | aaggcaaccc cgccagccta | 540 |
| gccgggtcct | caacgacagg | agcacgatca | tgcgcacccg | tggggccgcc atgccggcga | 600 |
| taatggcctg | cttctcgccg | aaacgtttgg | tggcgggacc | agtgacgaag gcttgagcga | 660 |
| gggcgtgcaa | gattccgaat | accgcaagcg | acaggccgat | catcgtcgcg ctccagcgaa | 720 |
| agcggtcctc | gccgaaaatg | acccagagcg | ctgccggcac | ctgtcctacg agttgcatga | 780 |
| taaagaagac | agtcataagt | gcggcgacga | tagtcatgcc | ccgcgcccac cggaaggagc | 840 |
| tgactgggtt | gaaggctctc | aagggcatcg | gtcgagatcc | cggtgcctaa tgagtgagct | 900 |
| aacttacatt | aattgcgttg | cgctcactgc | ccgctttcca | gtcgggaaac ctgtcgtgcc | 960 |
| agctgcatta | atgaatcggc | caacgcgcgg | ggagaggcgg | tttgcgtatt gggcgccagg | 1020 |
| gtggtttttc | ttttcaccag | tgagacgggc | aacagctgat | tgcccttcac cgcctggccc | 1080 |
| tgagagagtt | gcagcaagcg | gtccacgctg | gtttgcccca | gcaggcgaaa atcctgtttg | 1140 |
| atggtggtta | acggcgggat | ataacatgag | ctgtcttcgg | tatcgtcgta tcccactacc | 1200 |
| gagatatccg | caccaacgcg | cagcccggac | tcggtaatgg | cgcgcattgc gcccagcgcc | 1260 |
| atctgatcgt | tggcaaccag | catcgcagtg | ggaacgatgc | cctcattcag catttgcatg | 1320 |
| gtttgttgaa | aaccggacat | ggcactccag | tcgccttccc | gttccgctat cggctgaatt | 1380 |
| tgattgcgag | tgagatattt | atgccagcca | gccagacgca | gacgcgccga gacagaactt | 1440 |
| aatgggcccg | ctaacagcgc | gatttgctgg | tgacccaatg | cgaccagatg ctccacgccc | 1500 |
| agtcgcgtac | cgtcttcatg | ggagaaaata | atactgttga | tgggtgtctg gtcagagaca | 1560 |
| tcaagaaata | acgccggaac | attagtgcag | gcagcttcca | cagcaatggc atcctggtca | 1620 |
| tccagcggat | agttaatgat | cagcccactg | acgcgttgcg | cgagaagatt gtgcaccgcc | 1680 |
| gctttacagg | cttcgacgcc | gcttcgttct | accatcgaca | ccaccacgct ggcacccagt | 1740 |
| tgatcggcgc | gagatttaat | cgccgcgaca | atttgcgacg | gcgcgtgcag ggccagactg | 1800 |
| gaggtggcaa | cgccaatcag | caacgactgt | ttgcccgcca | gttgttgtgc cacgcggttg | 1860 |
| ggaatgtaat | tcagctccgc | catcgccgct | tccactttt | ccgcgttttt cgcagaaacg | 1920 |
| tggctggcct | ggttcaccac | gcgggaaacg | gtctgataag | agacaccggc atactctgcg | 1980 |
| acatcgtata | acgttactgg | tttcacattc | accaccct | | 2018 |

<210> SEQ ID NO 35
<211> LENGTH: 120
<212> TYPE: DNA
<213> ORGANISM: Artificial Sequence
<220> FEATURE:
<223> OTHER INFORMATION: Template

<400> SEQUENCE: 35
atactcatca ttaaacttcg cccttaccta ccacttcgtg tatgtagata ggtagtatac    60

```
aattgatatc gaaatgagta cgtagatagt agaaagtaag atggaggtga gagtgagagt      120
```

<210> SEQ ID NO 36
<211> LENGTH: 38
<212> TYPE: DNA
<213> ORGANISM: Artificial Sequence
<220> FEATURE:
<223> OTHER INFORMATION: Primer

<400> SEQUENCE: 36

```
atactcatca ttaaacttcg cccttaccta ccacttcg                              38
```

<210> SEQ ID NO 37
<211> LENGTH: 120
<212> TYPE: DNA
<213> ORGANISM: Artificial Sequence
<220> FEATURE:
<223> OTHER INFORMATION: Template
<220> FEATURE:
<221> NAME/KEY: misc_feature
<222> LOCATION: (23)..(23)
<223> OTHER INFORMATION: n = hydroxymethylcytosine
<220> FEATURE:
<221> NAME/KEY: misc_feature
<222> LOCATION: (23)..(23)
<223> OTHER INFORMATION: n = 5-hydroxymethylcytosine
<220> FEATURE:
<221> NAME/KEY: misc_feature
<222> LOCATION: (37)..(37)
<223> OTHER INFORMATION: n = 5-hydroxymethylcytosine
<220> FEATURE:
<221> NAME/KEY: misc_feature
<222> LOCATION: (49)..(49)
<223> OTHER INFORMATION: n = 5-hydroxymethylcytosine

<400> SEQUENCE: 37

```
gcggcgtgat actggtcccg agnctgaagt taggccnggg atgactgana gtcttccgag      60
accgacgaca caggtctccc tatagtgagt cgtattatgg cgagagaatg aatctccatc     120
```

<210> SEQ ID NO 38
<211> LENGTH: 42
<212> TYPE: DNA
<213> ORGANISM: Artificial Sequence
<220> FEATURE:
<223> OTHER INFORMATION: Primer

<400> SEQUENCE: 38

```
gatggagatt cattctctcg ccataatacg actcactata gg                         42
```

<210> SEQ ID NO 39
<211> LENGTH: 90
<212> TYPE: DNA
<213> ORGANISM: Artificial Sequence
<220> FEATURE:
<223> OTHER INFORMATION: Template
<220> FEATURE:
<221> NAME/KEY: misc_feature
<222> LOCATION: (50)..(50)
<223> OTHER INFORMATION: n = A or G or T or C
<220> FEATURE:
<221> NAME/KEY: misc_feature
<222> LOCATION: (51)..(51)
<223> OTHER INFORMATION: n = methylcytosine
<220> FEATURE:
<221> NAME/KEY: misc_feature
<222> LOCATION: (52)..(52)
<223> OTHER INFORMATION: n = A or G or T or C
<220> FEATURE:
<221> NAME/KEY: misc_feature
<222> LOCATION: (53)..(53)

<223> OTHER INFORMATION: n = A or G or T or C

<400> SEQUENCE: 39
gaagatgcag aagacaggaa ggatgaaaca ctcaggcgca cgctggcatn nnngacaaac    60
cacaagaaca ggctagtgag aatgaaggga                                     90

<210> SEQ ID NO 40
<211> LENGTH: 90
<212> TYPE: DNA
<213> ORGANISM: Artificial Sequence
<220> FEATURE:
<223> OTHER INFORMATION: Template
<220> FEATURE:
<221> NAME/KEY: misc_feature
<222> LOCATION: (49)..(49)
<223> OTHER INFORMATION: n = A or G or T or C
<220> FEATURE:
<221> NAME/KEY: misc_feature
<222> LOCATION: (50)..(50)
<223> OTHER INFORMATION: n = hydroxymethylcytosine
<220> FEATURE:
<221> NAME/KEY: misc_feature
<222> LOCATION: (51)..(51)
<223> OTHER INFORMATION: n = A or G or T or C
<220> FEATURE:
<221> NAME/KEY: misc_feature
<222> LOCATION: (52)..(52)
<223> OTHER INFORMATION: n = A or G or T or C

<400> SEQUENCE: 40
ccaactctga aacccaccaa cgccaacatc caccacacaa cccaagatnn nngaccatct    60
tacaaacata tcccttcatt ctcactagcc                                     90

<210> SEQ ID NO 41
<211> LENGTH: 160
<212> TYPE: DNA
<213> ORGANISM: Artificial Sequence
<220> FEATURE:
<223> OTHER INFORMATION: Template
<220> FEATURE:
<221> NAME/KEY: misc_feature
<222> LOCATION: (50)..(50)
<223> OTHER INFORMATION: n = A or G or T or C
<220> FEATURE:
<221> NAME/KEY: misc_feature
<222> LOCATION: (51)..(51)
<223> OTHER INFORMATION: n = methylcytosine
<220> FEATURE:
<221> NAME/KEY: misc_feature
<222> LOCATION: (52)..(52)
<223> OTHER INFORMATION: n = A or G or T or C
<220> FEATURE:
<221> NAME/KEY: misc_feature
<222> LOCATION: (53)..(53)
<223> OTHER INFORMATION: n = A or G or T or C
<220> FEATURE:
<221> NAME/KEY: misc_feature
<222> LOCATION: (109)..(109)
<223> OTHER INFORMATION: n = A or G or T or C
<220> FEATURE:
<221> NAME/KEY: misc_feature
<222> LOCATION: (110)..(110)
<223> OTHER INFORMATION: n = A or G or T or C
<220> FEATURE:
<221> NAME/KEY: misc_feature
<222> LOCATION: (112)..(112)
<223> OTHER INFORMATION: n = A or G or T or C

<400> SEQUENCE: 41
gaagatgcag aagacaggaa ggatgaaaca ctcaggcgca cgctggcatn nnngacaaac    60
cacaagaaca ggctagtgag aatgaaggga tatgtttgta agatggtcnn gnatcttggg  120

```
ttgtgtggtg gatgttggcg ttggtgggtt tcagagttgg                                    160
```

<210> SEQ ID NO 42
<211> LENGTH: 160
<212> TYPE: DNA
<213> ORGANISM: Artificial Sequence
<220> FEATURE:
<223> OTHER INFORMATION: Template
<220> FEATURE:
<221> NAME/KEY: misc_feature
<222> LOCATION: (49)..(49)
<223> OTHER INFORMATION: n = A or G or T or C
<220> FEATURE:
<221> NAME/KEY: misc_feature
<222> LOCATION: (50)..(50)
<223> OTHER INFORMATION: n =hydroxymethylcytosine
<220> FEATURE:
<221> NAME/KEY: misc_feature
<222> LOCATION: (51)..(51)
<223> OTHER INFORMATION: n = A or G or T or C
<220> FEATURE:
<221> NAME/KEY: misc_feature
<222> LOCATION: (52)..(52)
<223> OTHER INFORMATION: n = A or G or T or C
<220> FEATURE:
<221> NAME/KEY: misc_feature
<222> LOCATION: (108)..(108)
<223> OTHER INFORMATION: n = A or G or T or C
<220> FEATURE:
<221> NAME/KEY: misc_feature
<222> LOCATION: (109)..(109)
<223> OTHER INFORMATION: n = A or G or T or C
<220> FEATURE:
<221> NAME/KEY: misc_feature
<222> LOCATION: (111)..(111)
<223> OTHER INFORMATION: n = A or G or T or C

<400> SEQUENCE: 42

```
ccaactctga aacccaccaa cgccaacatc caccacacaa cccaagatnn nngaccatct            60
tacaaacata tcccttcatt ctcactagcc tgttcttgtg gtttgtcnng natgccagcg           120
tgcgcctgag tgtttcatcc ttcctgtctt ctgcatcttc                                 160
```

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43

```
cctgatgaaa caagcatgtc                                                        20
```

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44

```
cattactcac ttccccactt                                                        20
```

<210> SEQ ID NO 45
<211> LENGTH: 40
<212> TYPE: DNA
<213> ORGANISM: Artificial Sequence
<220> FEATURE:
<223> OTHER INFORMATION: Primer

<400> SEQUENCE: 45
gctgcagatt ggagccaaag ttgatggtga tggtggagcc                                40

<210> SEQ ID NO 46
<211> LENGTH: 45
<212> TYPE: DNA
<213> ORGANISM: Artificial Sequence
<220> FEATURE:
<223> OTHER INFORMATION: Primer

<400> SEQUENCE: 46
tcagtgctca tggactcata ctataccctg ggagcaaagt tgttg                          45

<210> SEQ ID NO 47
<211> LENGTH: 41
<212> TYPE: DNA
<213> ORGANISM: Artificial Sequence
<220> FEATURE:
<223> OTHER INFORMATION: Primer

<400> SEQUENCE: 47
cccactagac atgctctgcc caaaatgttg cttgccttcc g                              41

<210> SEQ ID NO 48
<211> LENGTH: 40
<212> TYPE: DNA
<213> ORGANISM: Artificial Sequence
<220> FEATURE:
<223> OTHER INFORMATION: Primer

<400> SEQUENCE: 48
tccctgagcc ctgatctagt aatactggct gaccggttct                                40

<210> SEQ ID NO 49
<211> LENGTH: 40
<212> TYPE: DNA
<213> ORGANISM: Artificial Sequence
<220> FEATURE:
<223> OTHER INFORMATION: Primer

<400> SEQUENCE: 49
acaccacagc agaagagagc taggattgtt gcacaggcca                                40

<210> SEQ ID NO 50
<211> LENGTH: 41
<212> TYPE: DNA
<213> ORGANISM: Artificial Sequence
<220> FEATURE:
<223> OTHER INFORMATION: Primer

<400> SEQUENCE: 50
gctgagctgt atccttgagg tacacgtggg tattccacag c                              41

<210> SEQ ID NO 51
<211> LENGTH: 40
<212> TYPE: DNA
<213> ORGANISM: Artificial Sequence
<220> FEATURE:
<223> OTHER INFORMATION: Primer

<400> SEQUENCE: 51
gtggatcttc agtggtggca atgctccctc atcctttgca                                40

<210> SEQ ID NO 52
<211> LENGTH: 40

```
<212> TYPE: DNA
<213> ORGANISM: Artificial Sequence
<220> FEATURE:
<223> OTHER INFORMATION: Primer

<400> SEQUENCE: 52
agcctctgaa cttgactgcc gcctggaact cctgacagtc                              40

<210> SEQ ID NO 53
<211> LENGTH: 40
<212> TYPE: DNA
<213> ORGANISM: Artificial Sequence
<220> FEATURE:
<223> OTHER INFORMATION: Primer

<400> SEQUENCE: 53
ggtccttgat ccacccagac acatggtgct ggtctaaccg                              40

<210> SEQ ID NO 54
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n = 5-carboxylcytosine

<400> SEQUENCE: 54
tcgacnggat c                                                             11

<210> SEQ ID NO 55
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n = DHU

<400> SEQUENCE: 55
tcgacnggat c                                                             11

<210> SEQ ID NO 56
<211> LENGTH: 13
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (13)..(13)
<223> OTHER INFORMATION: n = 5-formylcytosine

<400> SEQUENCE: 56
gtcgaccgga tcn                                                           13

<210> SEQ ID NO 57
<211> LENGTH: 13
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (13)..(13)
```

```
<223> OTHER INFORMATION: 5 oxime cytosine

<400> SEQUENCE: 57
gtcgaccgga tcn                                                          13

<210> SEQ ID NO 58
<211> LENGTH: 13
<212> TYPE: DNA
<213> ORGANISM: Artificial Sequence
<220> FEATURE:
<223> OTHER INFORMATION: Prime
<220> FEATURE:
<221> NAME/KEY: misc_feature
<222> LOCATION: (13)..(13)
<223> OTHER INFORMATION: n = Dihydrouracil

<400> SEQUENCE: 58
gtcgaccgga tcn                                                          13

<210> SEQ ID NO 59
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n = 5-carboxylcytosine

<400> SEQUENCE: 59
tcgacnggat c                                                            11

<210> SEQ ID NO 60
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n = amide cytosine

<400> SEQUENCE: 60
tcgacnggat c                                                            11

<210> SEQ ID NO 61
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n = Dihydrouracil

<400> SEQUENCE: 61
tcgacnggat c                                                            11

<210> SEQ ID NO 62
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
```

```
<222> LOCATION: (6)..(6)
<223> OTHER INFORMATION: n = 5-Methylcytosine

<400> SEQUENCE: 62
tcgacnggat c                                                          11

<210> SEQ ID NO 63
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n = 5-formylcytosine

<400> SEQUENCE: 63
tcgacnggat c                                                          11

<210> SEQ ID NO 64
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n = 5-hydroxymethylcytosine

<400> SEQUENCE: 64
tcgacnggat c                                                          11

<210> SEQ ID NO 65
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n = glucosyl-5-hydroxymethyl-cytosine

<400> SEQUENCE: 65
tcgacnggat c                                                          11

<210> SEQ ID NO 66
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n = Dihydrouracil

<400> SEQUENCE: 66
tcgacnggat c                                                          11

<210> SEQ ID NO 67
<211> LENGTH: 10
<212> TYPE: DNA
<213> ORGANISM: Artificial Sequence
<220> FEATURE:
<223> OTHER INFORMATION: Primer
<220> FEATURE:
```

```
<221> NAME/KEY: misc_feature
<222> LOCATION: (6)..(6)
<223> OTHER INFORMATION: n = Methylcytosine

<400> SEQUENCE: 67 cctgtngagc                                                          10

<210> SEQ ID NO 68
<211> LENGTH: 10
<212> TYPE: DNA
<213> ORGANISM: Artificial Sequence
<220> FEATURE:
<223> OTHER INFORMATION: Primer

<400> SEQUENCE: 68
cctgtcgagc                                                          10

<210> SEQ ID NO 69
<211> LENGTH: 10
<212> TYPE: DNA
<213> ORGANISM: Artificial Sequence
<220> FEATURE:
<223> OTHER INFORMATION: Primer

<400> SEQUENCE: 69
cctgttgagc                                                          10

<210> SEQ ID NO 70
<211> LENGTH: 10
<212> TYPE: DNA
<213> ORGANISM: Artificial Sequence
<220> FEATURE:
<223> OTHER INFORMATION: Primer

<400> SEQUENCE: 70
agtcttgatc                                                          10

<210> SEQ ID NO 71
<211> LENGTH: 10
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n = Methylcytosine

<400> SEQUENCE: 71 agtctngatc                                                          10

<210> SEQ ID NO 72
<211> LENGTH: 10
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n = Methylcytosine

<400> SEQUENCE: 72 cctgtngagc                                                          10

<210> SEQ ID NO 73
<211> LENGTH: 10
```

```
<212> TYPE: DNA
<213> ORGANISM: Artificial Sequence
<220> FEATURE:
<223> OTHER INFORMATION: Primer

<400> SEQUENCE: 73
cctgttgagc                                                                  10

<210> SEQ ID NO 74
<211> LENGTH: 10
<212> TYPE: DNA
<213> ORGANISM: Artificial Sequence
<220> FEATURE:
<223> OTHER INFORMATION: Primer

<400> SEQUENCE: 74
cctgtcgagc                                                                  10

<210> SEQ ID NO 75
<211> LENGTH: 116
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (19)..(19)
<223> OTHER INFORMATION: n = Methylcytosine
<220> FEATURE:
<221> NAME/KEY: misc_feature
<222> LOCATION: (34)..(34)
<223> OTHER INFORMATION: n = Methylcytosine
<220> FEATURE:
<221> NAME/KEY: misc_feature
<222> LOCATION: (57)..(57)
<223> OTHER INFORMATION: n = hydroxymethylcytosine
<220> FEATURE:
<221> NAME/KEY: misc_feature
<222> LOCATION: (67)..(67)
<223> OTHER INFORMATION: n = hydroxymethylcytosine
<220> FEATURE:
<221> NAME/KEY: misc_feature
<222> LOCATION: (78)..(78)
<223> OTHER INFORMATION: n = hydroxymethylcytosine

<400> SEQUENCE: 75
atactcatca ttaaacttng cccttaccta cttngtgtat gatgataggt agtatanaat           60
tgatatngaa atgagtangt agatagtaga aagtaagatg gaggtgagag tgagag             116

<210> SEQ ID NO 76
<211> LENGTH: 119
<212> TYPE: DNA
<213> ORGANISM: Artificial Sequence
<220> FEATURE:
<223> OTHER INFORMATION: Primer

<400> SEQUENCE: 76
atactcatca ttaaacttcg cccttaccta ccacttcgtg tatgtagata ggtagtatac          60
aattgatatc gaaatgagta cgtagatagt agaaagtaag atggaggtga gagtgagag          119

<210> SEQ ID NO 77
<211> LENGTH: 119
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (20)..(20)
```

<223> OTHER INFORMATION: n = Methylcytosine
<220> FEATURE:
<221> NAME/KEY: misc_feature
<222> LOCATION: (38)..(38)
<223> OTHER INFORMATION: n = Methylcytosine
<220> FEATURE:
<221> NAME/KEY: misc_feature
<222> LOCATION: (71)..(71)
<223> OTHER INFORMATION: n = Methylcytosine
<220> FEATURE:
<221> NAME/KEY: misc_feature
<222> LOCATION: (82)..(82)
<223> OTHER INFORMATION: n = Methylcytosine

<400> SEQUENCE: 77
tatgagtagt aatttgaagn gggaatggat ggtgaagnac atacatatat ccatcatatg    60
ttaactatag ntttactcat gnatctatca tctttcattc tacctccact ctcactctc    119

<210> SEQ ID NO 78
<211> LENGTH: 113
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(2)
<223> OTHER INFORMATION: n = Methylcytosine
<220> FEATURE:
<221> NAME/KEY: misc_feature
<222> LOCATION: (16)..(16)
<223> OTHER INFORMATION: n = Methylcytosine
<220> FEATURE:
<221> NAME/KEY: misc_feature
<222> LOCATION: (20)..(20)
<223> OTHER INFORMATION: n = hydroxymethylcytosine
<220> FEATURE:
<221> NAME/KEY: misc_feature
<222> LOCATION: (34)..(34)
<223> OTHER INFORMATION: n = hydroxymethylcytosine
<220> FEATURE:
<221> NAME/KEY: misc_feature
<222> LOCATION: (46)..(46)
<223> OTHER INFORMATION: n = hydroxymethylcytosine
<220> FEATURE:
<221> NAME/KEY: misc_feature
<222> LOCATION: (54)..(54)
<223> OTHER INFORMATION: n = Methylcytosine
<220> FEATURE:
<221> NAME/KEY: misc_feature
<222> LOCATION: (60)..(60)
<223> OTHER INFORMATION: n = Methylcytosine
<220> FEATURE:
<221> NAME/KEY: misc_feature
<222> LOCATION: (63)..(63)
<223> OTHER INFORMATION: n = Methylcytosine
<220> FEATURE:
<221> NAME/KEY: misc_feature
<222> LOCATION: (88)..(88)
<223> OTHER INFORMATION: n = Methylcytosine
<220> FEATURE:
<221> NAME/KEY: misc_feature
<222> LOCATION: (98)..(98)
<223> OTHER INFORMATION: n = Methylcytosine

<400> SEQUENCE: 78
gngtgatact ggtccngagn ctgaagttag gccngggatg actganagtc ttcngagacn    60
gangacacag gtctccctat agtgagtngt attatggnga gagaatgaat ctc    113

<210> SEQ ID NO 79
<211> LENGTH: 113
<212> TYPE: DNA
<213> ORGANISM: Artificial Sequence

```
<220> FEATURE:
<223> OTHER INFORMATION: Primer

<400> SEQUENCE: 79
gcgtgatact ggtcccgagc ctgaagttag gcccgggatg actgacagtc ttccgagacc      60
gacgacacag gtctccctat agtgagtcgt attatggcga gagaatgaat ctc            113

<210> SEQ ID NO 80
<211> LENGTH: 113
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: n = Methylcytosine
<220> FEATURE:
<221> NAME/KEY: misc_feature
<222> LOCATION: (17)..(17)
<223> OTHER INFORMATION: n = Methylcytosine
<220> FEATURE:
<221> NAME/KEY: misc_feature
<222> LOCATION: (35)..(35)
<223> OTHER INFORMATION: n = Methylcytosine
<220> FEATURE:
<221> NAME/KEY: misc_feature
<222> LOCATION: (55)..(55)
<223> OTHER INFORMATION: n = Methylcytosine
<220> FEATURE:
<221> NAME/KEY: misc_feature
<222> LOCATION: (61)..(61)
<223> OTHER INFORMATION: n = Methylcytosine
<220> FEATURE:
<221> NAME/KEY: misc_feature
<222> LOCATION: (64)..(64)
<223> OTHER INFORMATION: n = Methylcytosine
<220> FEATURE:
<221> NAME/KEY: misc_feature
<222> LOCATION: (89)..(89)
<223> OTHER INFORMATION: n = Methylcytosine
<220> FEATURE:
<221> NAME/KEY: misc_feature
<222> LOCATION: (99)..(99)
<223> OTHER INFORMATION: n = Methylcytosine

<400> SEQUENCE: 80
cgnactatga ccagggntcg gacttcaatc cgggncctac tgactgtcag aaggntctgg      60
ntgntgtgtc cagagggata tcactcagna taataccgnt ctcttactta gag             113

<210> SEQ ID NO 81
<211> LENGTH: 6
<212> TYPE: DNA
<213> ORGANISM: Artificial Sequence
<220> FEATURE:
<223> OTHER INFORMATION: Primer

<400> SEQUENCE: 81 cgacgc                                                                  6

<210> SEQ ID NO 82
<211> LENGTH: 6
<212> TYPE: DNA
<213> ORGANISM: Artificial Sequence
<220> FEATURE:
<223> OTHER INFORMATION: Primer

<400> SEQUENCE: 82 accgtg                                                                  6
```

```
<210> SEQ ID NO 83
<211> LENGTH: 6
<212> TYPE: DNA
<213> ORGANISM: Artificial Sequence
<220> FEATURE:
<223> OTHER INFORMATION: Primer

<400> SEQUENCE: 83 cgatgc                                                              6

<210> SEQ ID NO 84
<211> LENGTH: 6
<212> TYPE: DNA
<213> ORGANISM: Artificial Sequence
<220> FEATURE:
<223> OTHER INFORMATION: Primer

<400> SEQUENCE: 84 actgtg                                                              6
```

BISULFITE-FREE, BASE-RESOLUTION IDENTIFICATION OF CYTOSINE MODIFICATIONS

CROSS-REFERENCE TO RELATED APPLICATIONS

This application is a continuation of U.S. patent application Ser. No. 16/960,510, filed Jul. 7, 2020, which is a 371 of International Patent Application No. PCT/US2019/012627, filed Jan. 8, 2019, which claims the benefit of U.S. Provisional Application Nos. 62/614,798 filed Jan. 8, 2018, 62/660,523 filed Apr. 20, 2018, and 62/771,409 filed Nov. 26, 2018, each of which is incorporated herein by reference in its entirety.

REFERENCE TO AN ELECTRONIC SEQUENCE LISTING

The contents of the electronic sequence listing (File Name: 39087-305_ST25.txt; Size: 27,000 bytes; and Date of Creation: Jul. 1, 2021), submitted on Jul. 1, 2021, is herein incorporated by reference in its entirety.

FIELD OF THE INVENTION

This disclosure provides methods for identifying in a nucleic acid sequence the locations of 5-methylcytosine, 5-hydroxymethylcytosine, 5-carboxylcytosine and/or 5-formylcytosine.

BACKGROUND

5-Methylcytosine (5mC) and 5-hydroxymethylcytosine (5hmC) are the two major epigenetic marks found in the mammalian genome. 5hmC is generated from 5mC by the ten-eleven translocation (TET) family dioxygenases. Tet can further oxidize 5hmC to 5-formylcytosine (5fC) and 5-carboxylcytosine (5caC), which exists in much lower abundance in the mammalian genome compared to 5mC and 5hmC (10-fold to 100-fold lower than that of 5hmC). Together, 5mC and 5hmC play crucial roles in a broad range of biological processes from gene regulation to normal development. Aberrant DNA methylation and hydroxymethylation have been associated with various diseases and are well-accepted hallmarks of cancer. Therefore, the determination of 5mC and 5hmC in DNA sequence is not only important for basic research, but also is valuable for clinical applications, including diagnosis and therapy.

5fC and 5caC are the two final oxidized derivatives of 5mC and can be converted to unmodified cytosine by Thymine DNA glycosylase (TDG) in base excision repair pathway. Therefore, 5fC and 5caC are two important key intermediates in the active demethylation process, which plays important role in embryonic development. 5fC and 5caC are found in these contexts and may serve as indicator of nearly complete 5mC demethylation. 5fC and 5caC may also play additional functions such as bind specific proteins and affect the rate and specificity of RNA polymerase II.

5mC is also a post-transcriptional RNA modification that has been identified in both stable and highly abundant tRNAs and rRNAs, and in mRNAs. In addition, 5mC has been detected in snRNA (small nuclear RNA), miRNA (microRNA), lncRNA (long noncoding RNA) and eRNA (enhancer RNA). However, there appears to be differences in the occurrence of 5mC in specific RNA types in different organisms. For example, 5mC appears not to be present in tRNA and mRNA from bacteria, while it has been found in tRNA and mRNA in eukaryotes and archaea.

5hmC has also been detected in RNA. For example, mRNA from *Drosophila* and mouse has been found to contain 5hmC. The same family of enzymes that oxidize 5mC in DNA was reported to catalyze the formation of 5hmC in mammalian total RNA. In flies, a transcriptome wide study using methylation RNA immunoprecipitation sequencing (MeRIP-seq) with 5hmC antibodies, detected the presence of 5hmC in many mRNA coding sequences, with particularly high levels in the brain. It was also reported that active translation is associated with high 5hmC levels in RNA, and flies lacking the TET enzyme responsible for 5hmC deposition in RNA have impaired brain development.

The current gold standard and most widely used method for DNA methylation and hydroxymethylation analysis is bisulfite sequencing (BS), and its derived methods such as Tet-assisted bisulfite sequencing (TAB-Seq) and oxidative bisulfite sequencing (oxBS). All of these methods employ bisulfite treatment to convert unmethylated cytosine to uracil while leaving 5mC and/or 5hmC intact. Through PCR amplification of the bisulfite-treated DNA, which reads uracil as thymine, the modification information of each cytosine can be inferred at a single base resolution (where the transition of C to T provides the location of the unmethylated cytosine). There are, however, at least two main drawbacks to bisulfite sequencing. First, bisulfite treatment is a harsh chemical reaction, which degrades more than 90% of the DNA due to depurination under the required acidic and thermal conditions. This degradation severely limits its application to low-input samples, such as clinical samples including circulating cell-free DNA and single-cell sequencing. Second, bisulfite sequencing relies on the complete conversion of unmodified cytosine to thymine. Unmodified cytosine accounts for approximately 95% of the total cytosine in the human genome. Converting all these positions to thymine severely reduces sequence complexity, leading to poor sequencing quality, low mapping rates, uneven genome coverage and increased sequencing cost. Bisulfite sequencing methods are also susceptible to false detection of 5mC and 5hmC due to incomplete conversion of unmodified cytosine to thymine.

Bisulfite sequencing has also been used to detect cytosine methylation in RNA. Unlike other methods for detecting 5mC in RNA such as methylated-RNA-immunoprecipitation, RNA-bisulfite-sequencing (RNA-BS-seq) has the advantage of being able to determine of the extent of methylation of a specific C position in RNA. RNA-BS-seq, however, suffers from the same drawbacks described above for bisulfite sequencing of DNA. In particular, the reaction conditions can cause substantial degradation of RNA.

There is a need for a method for DNA methylation and hydroxymethylation analysis that is a mild reaction that can detect the modified cytosine (5mC and 5hmC) at base-resolution quantitatively without affecting the unmodified cytosine. Likewise, there is a need for a method for RNA methylation and hydroxymethylation analysis that employs mild reaction conditions and can detect the modified cytosine quantitatively at base resolution without affecting the unmodified cytosine.

SUMMARY OF THE INVENTION

The present invention provides methods for identifying the location of one or more of 5-methylcytosine, 5-hydroxymethylcytosine, 5-carboxylcytosine and/or 5-formylcytosine in a nucleic acid. The methods described herein provide for DNA or RNA methylation and hydroxymethylation analysis involving mild reactions that detect the modified cytosine quantitatively with base-resolution without affecting the unmodified cytosine. Provided herein is a new method for identifying 5mC and 5hmC by combining TET oxidation and reduction by borane derivatives (e.g., pyridine borane and 2-picoline borane (pic-BH3)), referred to herein as TAPS (TET Assisted Pyridine borane Sequencing) (Table 1). TAPS detects modifications directly with high sensitivity and specificity, without affecting unmodified cytosines, and can be adopted to detect other cytosine modifications. It is non-destructive, preserving RNA and DNA up to 10 kbs long. Compared with bisulfite sequencing, TAPS results in higher mapping rates, more even coverage and lower sequencing costs, enabling higher quality, more comprehensive and cheaper methylome analyses. Variations of this method that do not employ the oxidation step are used to identify 5fC and/or 5caC as described herein.

In one aspect, the present invention provides a method for identifying 5-methylcytosine (5mC) in a target nucleic acid comprising the steps of:
 a. providing a nucleic acid sample comprising the target nucleic acid;
 b. modifying the nucleic acid comprising the steps of:
   i. adding a blocking group to the 5-hydroxymethylcytosine (5hmC) in the nucleic acid sample;
   ii. converting the 5mC in the nucleic acid sample to 5-carboxylcytosine (5caC) and/or 5-formylcytosine (5fC); and
   iii. converting the 5caC and/or 5fC to dihydrouracil (DHU) to provide a modified nucleic acid sample comprising a modified target nucleic acid; and
 c. detecting the sequence of the modified target nucleic acid; wherein a cytosine (C) to thymine (T) transition in the sequence of the modified target nucleic acid compared to the target nucleic acid provides the location of a 5mC in the target nucleic acid.

In embodiments of the method for identifying 5mC in a target nucleic acid, the percentages of the T at each transition location provide a quantitative level of 5mC at each location in the target nucleic acid. In embodiments, the nucleic acid is DNA. In other embodiments, nucleic acid is RNA.

In another aspect, the present invention provides a method for identifying 5mC or 5hmC in a target nucleic acid comprising the steps of:
 a. providing a nucleic acid sample comprising the target nucleic acid;
 b. modifying the nucleic acid comprising the steps of:
   i. converting the 5mC and 5hmC in the nucleic acid sample to 5-carboxylcytosine (5caC) and/or 5fC; and
   ii. converting the 5caC and/or 5fC to DHU to provide a modified nucleic acid sample comprising a modified target nucleic acid; and
 c. detecting the sequence of the modified target nucleic acid; wherein a cytosine (C) to thymine (T) transition in the sequence of the modified target nucleic acid compared to the target nucleic acid provides the location of either a 5mC or 5hmC in the target nucleic acid.

In embodiments of the method for identifying 5mC or 5hmC, the percentages of the T at each transition location provide a quantitative level of 5mC or 5hmC at each location in the target nucleic acid. In embodiments, the nucleic acid is DNA. In other embodiments, nucleic acid is RNA.

In another aspect, the invention provides a method for identifying 5mC and identifying 5hmC in a target nucleic acid comprising:

a. identifying 5mC in the target nucleic acid comprising the steps of:
   i. providing a first nucleic acid sample comprising the target nucleic acid;
   ii. modifying the nucleic acid in the first sample comprising the steps of:
     1. adding a blocking group to the 5-hydroxymethylcytosine (5hmC) in the first nucleic acid sample;
     2. converting the 5mC in the first nucleic acid sample to 5caC and/or 5fC; and
     3. converting the 5caC and/or 5fC to DHU to provide a modified first DNA sample comprising a modified target nucleic acid;
   iii. optionally amplifying the copy number of the modified target nucleic acid; and
   iv. detecting the sequence of the modified target nucleic acid; wherein a cytosine (C) to thymine (T) transition in the sequence of the modified target nucleic acid compared to the target nucleic acid provides the location of a 5mC in the target nucleic acid.
 b. identifying 5mC or 5hmC in the target nucleic acid comprising the steps of:
   i. providing a second nucleic acid sample comprising the target nucleic acid;
   ii. modifying the nucleic acid in the second sample comprising the steps of:
     1. converting the 5mC and 5hmC in the second nucleic acid sample to 5caC and/or 5fC; and
     2. converting the 5caC and/or 5fC to DHU to provide a modified second nucleic acid sample comprising a modified target nucleic acid;
   iii. optionally amplifying the copy number of the modified target nucleic acid;
   iv. detecting the sequence of the modified target nucleic acid from the second sample; wherein a cytosine (C) to thymine (T) transition in the sequence of the modified target nucleic acid compared to the target nucleic acid provides the location of either a 5mC or 5hmC in the target nucleic acid; and
 c. comparing the results of steps (a) and (b), wherein a C to T transitions present in step (b) but not in step (a) provides the location of 5hmC in the target nucleic acid.

In embodiments for identifying 5mC and identifying 5hmC in a target nucleic acid, in step (a) the percentages of the T at each transition location provide a quantitative level of 5mC in the target nucleic acid; in step (b), the percentages of the T at each transition location provide a quantitative level of 5mC or 5hmC in the target nucleic acid; and in step (c) the differences in percentages for a C to T transition identified in step (b), but not in step (a) provides the quantitative level of a 5hmC at each location in the target nucleic acid. In embodiments, the nucleic acid is DNA. In other embodiments, nucleic acid is RNA.

In embodiments of the invention, the blocking group added to 5hmC in the nucleic acid sample is a sugar. In embodiments, the sugar is a naturally-occurring sugar or a modified sugar, for example glucose or a modified glucose. In embodiments of the invention, the blocking group is added to 5hmC by contacting the nucleic acid sample with UDP linked to a sugar, for example UDP-glucose or UDP linked to a modified glucose in the presence of a glucosyltransferase enzyme, for example, T4 bacteriophage β-glucosyltransferase (βGT) and T4 bacteriophage α-glucosyltransferase (αGT) and derivatives and analogs thereof.

In embodiments of the invention, the step of converting the 5mC in the nucleic acid sample to 5caC and/or 5fC and the step of converting the 5mC and 5hmC in the nucleic acid sample to 5caC and/or 5fC each comprises contacting the nucleic acid sample with a ten eleven translocation (TET) enzyme. In further embodiments, the TET enzyme is one or more of human TET1, TET2, and TET3; murine Tet1, Tet2, and Tet3; *Naegleria* TET (NgTET); *Coprinopsis cinerea* (CcTET) and derivatives or analogues thereof. In embodiments, the TET enzyme is NgTET.

In another aspect, the invention provides a method for identifying 5caC or 5fC in a target nucleic acid comprising the steps of:
  a. providing a nucleic acid sample comprising the target nucleic acid;
  b. converting the 5caC and 5fC to DHU to provide a modified nucleic acid sample comprising a modified target nucleic acid;
  c. optionally amplifying the copy number of the modified target nucleic acid; and
  d. detecting the sequence of the modified target nucleic acid; wherein a cytosine (C) to thymine (T) transition in the sequence of the modified target nucleic acid compared to the target nucleic acid provides the location of either a 5caC or 5fC in the target nucleic acid.

In embodiments of the method for identifying 5caC or 5fC in a target nucleic acid, the percentages of the T at each transition location provide a quantitative level for 5caC or 5fC at each location in the target nucleic acid.

In another aspect, the invention provides a method for identifying 5caC in a target nucleic acid comprising the steps of:
  a. providing a nucleic acid sample comprising the target nucleic acid;
  b. adding a blocking group to the 5fC in the nucleic acid sample;
  c. converting the 5caC to DHU to provide a modified nucleic acid sample comprising a modified target nucleic acid;
  d. optionally amplifying the copy number of the modified target nucleic acid; and
  e. determining the sequence of the modified target nucleic acid; wherein a cytosine (C) to thymine (T) transition in the sequence of the modified target nucleic acid compared to the target nucleic acid provides the location of a 5caC in the target nucleic acid.

In embodiments of the method for identifying 5caC in a target nucleic acid, the percentages of the T at each transition location provide a quantitative level for 5caC at each location in the target nucleic acid. In embodiments, the nucleic acid is DNA. In other embodiments, nucleic acid is RNA.

In embodiments of the invention, adding a blocking group to the 5fC in the nucleic acid sample comprises contacting the nucleic acid with an aldehyde reactive compound including, for example, hydroxylamine derivatives (such as O-ethylhydroxylamine), hydrazine derivatives, and hydrazide derivatives.

In another aspect, the invention provides a method for identifying 5fC in a target nucleic acid comprising the steps of:
  a. providing a nucleic acid sample comprising the target nucleic acid;
  b. adding a blocking group to the 5caC in the nucleic acid sample
  c. converting the 5fC to DHU to provide a modified nucleic acid sample comprising a modified target nucleic acid;
  d. optionally amplifying the copy number of the modified target nucleic acid;
  e. detecting the sequence of the modified target nucleic acid; wherein a cytosine (C) to thymine (T) transition in the sequence of the modified target nucleic acid compared to the target nucleic acid provides the location of a 5fC in the target nucleic acid.

In embodiments of the method for identifying 5fC in a target nucleic acid, the percentages of the T at each transition location provide a quantitative level for 5fC at each location in the target nucleic acid. In embodiments, the nucleic acid (sample and target) is DNA. In other embodiments, nucleic acid (sample and target) is RNA.

In embodiments, the step of adding a blocking group to the 5caC in the nucleic acid sample comprises contacting the nucleic acid sample with a carboxylic acid derivatization reagent, including, for example, 1-ethyl-3-(3-dimethylaminopropyl)carbodiimide (EDC) and (ii) an amine (such as ethylamine), hydrazine, or hydroxylamine compound.

In embodiments of the invention, the methods above further comprise the step of amplifying the copy number of the modified target nucleic acid. In embodiments, this amplification step is performed prior to the step of detecting the sequence of the modified target nucleic acid. The step of amplifying the copy number when the modified target nucleic acid is DNA may be accomplished by performing the polymerase chain reaction (PCR), primer extension, and/or cloning. When the modified target nucleic acid is RNA, the step of amplifying the copy number may be accomplished by RT-PCR using oligo(dT) primer (for mRNA), random primers, and/or gene specific primers.

In embodiments of the invention, the DNA sample comprises picogram quantities of DNA. In embodiments of the invention, the DNA sample comprises about 1 pg to about 900 pg DNA, about 1 pg to about 500 pg DNA, about 1 pg to about 100 pg DNA, about 1 pg to about 50 pg DNA, about 1 to about 10 pg, DNA, less than about 200 pg, less than about 100 pg DNA, less than about 50 pg DNA, less than about 20 pg DNA, and less than about 5 pg DNA. In other embodiments of the invention, the DNA sample comprises nanogram quantities of DNA. In embodiments of the invention, the DNA sample contains about 1 to about 500 ng of DNA, about 1 to about 200 ng of DNA, about 1 to about 100 ng of DNA, about 1 to about 50 ng of DNA, about 1 ng to about 10 ng of DNA, about 1 ng to about 5 ng of DNA, less than about 100 ng of DNA, less than about 50 ng of DNA less than about 5 ng of DNA, or less that about 2 ng of DNA. In embodiments of the invention, the DNA sample comprises circulating cell-free DNA (cfDNA). In embodiments of the invention the DNA sample comprises microgram quantities of DNA.

In embodiments of the invention, the step of converting the 5caC and/or 5fC to DHU comprises contacting the nucleic acid sample with a reducing agent including, for example, pyridine borane, 2-picoline borane (pic-$BH_3$), borane, sodium borohydride, sodium cyanoborohydride, and sodium triacetoxyborohydride. In a preferred embodiment, the reducing agent is pic-$BH_3$ and/or pyridine borane.

In embodiments of the invention, the step of determining the sequence of the modified target nucleic acid comprises chain termination sequencing, microarray, high-throughput sequencing, and restriction enzyme analysis.

BRIEF DESCRIPTION OF THE FIGURES

FIG. 1. Borane-containing compounds screening. Borane-containing compounds were screened for conversion of 5caC to DHU in an 11 mer oligonucleotide ("oligo"), with conversion rate estimated by MALDI. 2-picoline borane (pic-borane), borane pyridine, and tert-butylamine borane could completely convert 5caC to DHU while ethylenediamine borane and dimethylamine borane gave around 30% conversion rate. No detectable products measured (n.d.) with dicyclohexylamine borane, morpholine borane, 4-methylmorpholine borane, and trimethylamine borane. Other reducing agents such as sodium borohydride and sodium tri(acetoxy)borohydride decomposed rapidly in acidic media and lead to incomplete conversion. Sodium cyanoborohydride was not used due to potential for hydrogen cyanide formation under acidic condition. Pic-borane and pyridine borane were chosen because of complete conversion, low toxicity and high stability.

FIG. 2A-B. Pic-borane reaction on DNA oligos. (A) MALDI characterization of 5caC-containing 11 mer model DNA treated with pic-borane. Calculated mass (m/z) shown above each graph, observed mass shown to the left of the peak. (B) The conversion rates of dC and various cytosine derivatives were quantified by HPLC-MS/MS. Data shown as mean±SD of three replicates.

FIG. 13A-B. (A) TAPS is compatible with various DNA and RNA polymerase and induces complete C-to-T transition as shown by Sanger sequencing. Model DNA containing methylated CpG sites for the polymerase test and primer sequences are described herein. After TAPS treatment, 5mC was converted to DHU. KAPA HiFi Uracil plus polymerase, Taq polymerase, and Vent exo-polymerase would read DHU as T and therefore induce complete C-to-T transition after PCR. Alternatively, primer extension was done with biotin-labelled primer and isothermal polymerases including Klenow fragment, Bst DNA polymerase, and phi29 DNA polymerase. The newly synthesized DNA strand was separated by Dynabeads MyOne Streptavidin Cl and then amplified by PCR with Taq polymerase and processed for Sanger sequencing. T7 RNA polymerase could efficiently bypass DHU and insert adenine opposite to DHU site, which is proved by RT-PCR and Sanger sequencing. (B) Certain other commercialized polymerases did not amplify DHU containing DNA efficiently. After TAPS treatment, 5mC was converted to DHU. KAPA HiFi Uracil plus polymerase and Taq polymerase would read DHU as T and therefore induce complete C-to-T transition. Low or no C-to-T transition was observed with certain other commercialized polymerases including KAPA HiFi polymerase, Pfu polymerase, Phusion polymerase and NEB Q5 polymerase (not shown).

FIG. 19A-B. TAPS resulted in more even coverage and fewer uncovered positions than WGBS. Comparison of depth of coverage across (A) all bases and (B) CpG sites between WGBS and TAPS, computed on both strands. For "TAPS (down-sampled)", random reads out of all mapped TAPS reads were selected so that the median coverage matched the median coverage of WGBS. Positions with coverage above 50× are shown in the last bin.

due to plasma nuclease digestion. After library construction, it becomes ~300 bp, which is the sharp band in (B).

FIG. 26A-D. High-quality cell-free DNA TAPS. (A) Conversion rate of 5mC in TAPS-treated cfDNA. (B) False positive rate in TAPS-treated cfDNA. (C) Fraction of all sequenced read pairs that were uniquely mapped to the genome. (D) Fraction of all sequenced read pairs that were uniquely mapped to the genome and after removal of PCR duplication reads. CHG and CHH are non-CpG contexts.

Figure 27:
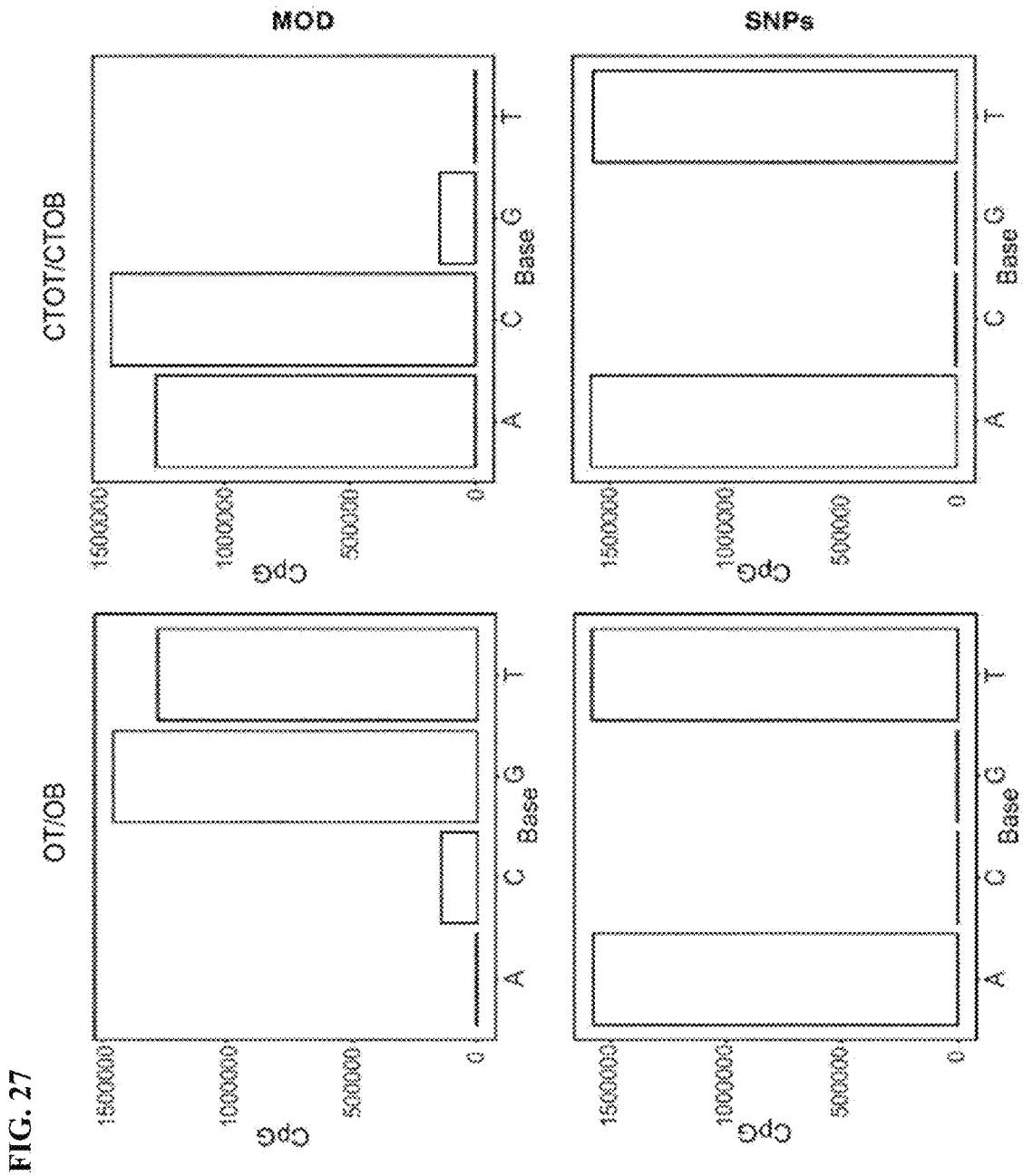

FIG. 27. TAPS can detect genetic variants. Methylation (MOD, top row) and C-to-T SNPs (bottom row) showed distinct base distribution patterns in original top strand (OT)/original bottom strand (OB), left column, and in strands complementary to OT (CTOT) and OB (CTOB), right column.

DETAILED DESCRIPTION OF THE INVENTION

The present invention provides a bisulfite-free, base-resolution method for detecting 5mC and 5hmC in a sequence, herein named TAPS. TAPS consists of mild enzymatic and chemical reactions to detect 5mC and 5hmC directly and quantitatively at base-resolution without affecting unmodified cytosine. The present invention also provides methods to detect 5fC and 5caC at base resolution without affecting unmodified cytosine. Thus, the methods provided herein provide mapping of 5mC, 5hmC, 5fC and 5caC and overcome the disadvantages of previous methods such as bisulfate sequencing.

TABLE 1

Comparison of BS and related methods versus TAPS, TAPSβ and CAPS for 5mC and 5hmC sequencing.

| Base | BS | TAB-Seq | oxBS | TAPS | TAPSβ | CAPS |
|---|---|---|---|---|---|---|
| C | T | T | T | C | C | C |
| 5mC | C | T | C | T | T | C |
| 5hmC | C | C | T | T | C | T |

Methods for Identifying 5mC

In one aspect, the present invention provides a method for identifying 5-methylcytosine (5mC) in a target DNA comprising the steps of:
a. providing a DNA sample comprising the target DNA;
b. modifying the DNA comprising the steps of:
   i. adding a blocking group to the 5-hydroxymethylcytosine (5hmC) in the DNA sample;
   ii. converting the 5mC in the DNA sample to 5-carboxylcytosine (5caC) and/or 5-formylcytosine (5fC); and
   iii. converting the 5caC and/or 5fC to DHU to provide a modified DNA sample comprising a modified target DNA;
c. detecting the sequence of the modified target DNA; wherein a cytosine (C) to thymine (T) transition in the sequence of the modified target DNA compared.

In embodiments of the method for identifying 5mC in the target DNA, the method provides a quantitative measure for the frequency the of 5mC modification at each location where the modification was identified in the target DNA. In embodiments, the percentages of the T at each transition location provide a quantitative level of 5mC at each location in the target DNA.

In order to identify 5mC in a target DNA without including 5hmC, the 5hmC in the sample is blocked so that it is not subject to conversion to 5caC and/or 5fC. In the methods of the present invention, 5hmC in the sample DNA are rendered non-reactive to the subsequent steps by adding a blocking group to the 5hmC. In one embodiment, the blocking group is a sugar, including a modified sugar, for example glucose or 6-azide-glucose (6-azido-6-deoxy-D-glucose). The sugar blocking group is added to the hydroxymethyl group of 5hmC by contacting the DNA sample with uridine diphosphate (UDP)-sugar in the presence of one or more glucosyltransferase enzymes.

In embodiments, the glucosyltransferase is T4 bacteriophage β-glucosyltransferase (βGT), T4 bacteriophage α-glucosyltransferase (αGT), and derivatives and analogs thereof βGT is an enzyme that catalyzes a chemical reaction in which a beta-D-glucosyl (glucose) residue is transferred from UDP-glucose to a 5-hydroxymethylcytosine residue in a nucleic acid.

By stating that the blocking group is, for example, glucose, this refers to a glucose moiety (e.g., a beta-D-glucosyl residue) being added to 5hmC to yield glucosyl 5-hydroxymethyl cytosine. The sugar blocking group can be any sugar or modified sugar that is a substrate of the glucosyltransferase enzyme and blocks the subsequent conversion of the 5hmC to 5caC and/or 5fC. The step of converting the 5mC in the DNA sample to 5caC and/or 5fC is then accomplished by the methods provided herein, such as by oxidation using a TET enzyme. And converting the 5caC and/or 5fC to DHU is accomplished by the methods provided herein, such by borane oxidation.

The method for identifying 5-methylcytosine (5mC) can be performed on an RNA sample to identify the location of, and provide a quantitative measure of, 5mC in a target RNA.

Methods for Identifying 5mC or 5hmC (Together)

In another aspect, the present invention provides a method for identifying 5mC or 5hmC in a target DNA comprising the steps of:
a. providing a DNA sample comprising the target DNA;
b. modifying the DNA comprising the steps of:
   i. converting the 5mC and 5hmC in the DNA sample to 5-carboxylcytosine (5caC) and/or 5fC; and
   ii. converting the 5caC and/or 5fC to DHU to provide a modified DNA sample comprising a modified target DNA;
c. detecting the sequence of the modified target DNA; wherein a cytosine (C) to thymine (T) transition in the sequence of the modified target DNA compared to the target DNA provides the location of either a 5mC or 5hmC in the target DNA.

In embodiments of the method for identifying 5mC or 5hmC in the target DNA, the method provides a quantitative measure for the frequency the of 5mC or 5hmC modifications at each location where the modifications were identified in the target DNA. In embodiments, the percentages of the T at each transition location provide a quantitative level of 5mC or 5hmC at each location in the target DNA.

This method for identifying 5mC or 5hmC provides the location of 5mC and 5hmC, but does not distinguish between the two cytosine modifications. Rather, both 5mC and 5hmC are converted to DHU. The presence of DHU can be detected directly, or the modified DNA can be replicated by known methods where the DHU is converted to T.

The method for identifying 5mC or 5hmC can be performed on an RNA sample to identify the location of, and provide a quantitative measure of, 5mC or 5hmC in a target RNA.

Methods for Identifying 5mC and Identifying 5hmC

The present invention provides a method for identifying 5mC and identifying 5hmC in a target DNA by (i) performing the method for identifying 5mC on a first DNA sample described herein, and (ii) performing the method for identifying 5mC or 5hmC on a second DNA sample described herein. The location of 5mC is provided by (i). By comparing the results of (i) and (ii), wherein a C to T transitions detected in (ii) but not in (i) provides the location of 5hmC in the target DNA. In embodiments, the first and second DNA samples are derived from the same DNA sample. For example, the first and second samples may be separate aliquots taken from a sample comprising DNA to be analyzed.

Because the 5mC and 5hmC (that is not blocked) are converted to 5fC and 5caC before conversion to DHU, any existing 5fC and 5caC in the DNA sample will be detected as 5mC and/or 5hmC. However, given the extremely low levels of 5fC and 5caC in genomic DNA under normal conditions, this will often be acceptable when analyzing methylation and hydroxymethylation in a DNA sample. The 5fC and 5caC signals can be eliminated by protecting the 5fC and 5caC from conversion to DHU by, for example, hydroxylamine conjugation and EDC coupling, respectively.

The above method identifies the locations and percentages of 5hmC in the target DNA through the comparison of 5mC locations and percentages with the locations and percentages of 5mC or 5hmC (together). Alternatively, the location and frequency of 5hmC modifications in a target DNA can be measured directly. Thus, in one aspect the invention provides a method for identifying 5hmC in a target DNA comprising the steps of:
  a. providing a DNA sample comprising the target DNA;
  b. modifying the DNA comprising the steps of:
    i. converting the 5hmC in the DNA sample to 5fC; and
    ii. converting the 5fC to DHU to provide a modified DNA sample comprising a modified target DNA;
  c. detecting the sequence of the modified target DNA; wherein a cytosine (C) to thymine (T) transition in the sequence of the modified target DNA compared to the target DNA provides the location of a 5hmC in the target DNA.

In embodiments, the step of converting the 5hmC to 5fC comprises oxidizing the 5hmC to 5fC by contacting the DNA with, for example, potassium perruthenate ($KRuO_4$) (as described in Science. 2012, 33, 934-937 and WO2013017853, incorporated herein by reference); or Cu(II)/TEMPO (copper(II) perchlorate and 2,2,6,6-tetramethylpiperidine-1-oxyl (TEMPO)) (as described in Chem. Commun., 2017, 53, 5756-5759 and WO2017039002, incorporated herein by reference). The 5fC in the DNA sample is then converted to DHU by the methods disclosed herein, e.g., by the borane reaction.

The method for identifying 5mC and identifying 5hmC can be performed on an RNA sample to identify the location of, and provide a quantitative measure of, 5mC and 5hmC in a target RNA.

Methods for Identifying 5caC or 5fC

In one aspect, the invention provides a method for identifying 5caC or 5fC in a target DNA comprising the steps of:
  a. providing a DNA sample comprising the target DNA;
  b. converting the 5caC and/or 5fC to DHU to provide a modified DNA sample comprising a modified target DNA;
  c. optionally amplifying the copy number of the modified target DNA;
  d. detecting the sequence of the modified target DNA; wherein a cytosine (C) to thymine (T) transition in the sequence of the modified target DNA compared to the target DNA provides the location of either a 5caC or 5fC in the target DNA.

This method for identifying 5fC or 5caC provides the location of 5fC or 5caC, but does not distinguish between these two cytosine modifications. Rather, both 5fC and 5caC are converted to DHU, which is detected by the methods described herein.

Methods for Identifying 5caC

In another aspect, the invention provides a method for identifying 5caC in a target DNA comprising the steps of:
  a. providing a DNA sample comprising the target DNA;
  b. adding a blocking group to the 5fC in the DNA sample;
  c. converting the 5caC to DHU to provide a modified DNA sample comprising a modified target DNA;
  d. optionally amplifying the copy number of the modified target DNA; and
  e. determining the sequence of the modified target DNA; wherein a cytosine (C) to thymine (T) transition in the sequence of the modified target DNA compared to the target DNA provides the location of a 5caC in the target DNA.

In embodiments of the method for identifying 5caC in the target DNA, the method provides a quantitative measure for the frequency the of 5caC modification at each location where the modification was identified in the target DNA. In embodiments, the percentages of the T at each transition location provide a quantitative level of 5caC at each location in the target DNA.

In this method, 5fC is blocked (and 5mC and 5hmC are not converted to DHU) allowing identification of 5caC in the target DNA. In embodiments of the invention, adding a blocking group to the 5fC in the DNA sample comprises contacting the DNA with an aldehyde reactive compound including, for example, hydroxylamine derivatives, hydrazine derivatives, and hyrazide derivatives. Hydroxylamine derivatives include ashydroxylamine; hydroxylamine hydrochloride; hydroxylammonium acid sulfate; hydroxylamine phosphate; O-methylhydroxylamine; O-hexylhydroxylamine; O-pentylhydroxylamine; O-benzylhydroxylamine; and particularly, O-ethylhydroxylamine (EtONH2), O-alkylated or O-arylated hydroxylamine, acid or salts thereof. Hydrazine derivatives include N-alkylhydrazine, N-arylhydrazine, N-benzylhydrazine, N,N-dialkylhydrazine, N,N-diarylhydrazine, N,N-dibenzylhydrazine, N,N-alkylbenzylhydrazine, N,N-arylbenzylhydrazine, and N,N-alkylarylhydrazine. Hydrazide derivatives include -toluenesulfonylhydrazide, N-acylhydrazide, N,N-alkylacylhydrazide, N,N-benzylacylhydrazide, N,N-arylacylhydrazide, N-sulfonylhydrazide, N,N-alkylsulfonylhydrazide, N,N-benzylsulfonylhydrazide, and N,N-arylsulfonylhydrazide.

The method for identifying 5caC can be performed on an RNA sample to identify the location of, and provide a quantitative measure of, 5caC in a target RNA.

Methods for Identifying 5fC

In another aspect, the invention provides a method for identifying 5fC in a target DNA comprising the steps of:
  a. providing a DNA sample comprising the target DNA;
  b. adding a blocking group to the 5caC in the DNA sample;
  c. converting the 5fC to DHU to provide a modified DNA sample comprising a modified target DNA;
  d. optionally amplifying the copy number of the modified target DNA;

e. detecting the sequence of the modified target DNA; wherein a cytosine (C) to thymine (T) transition in the sequence of the modified target DNA compared to the target DNA provides the location of a 5fC in the target DNA.

In embodiments of the method for identifying 5fC in the target DNA, the method provides a quantitative measure for the frequency the of 5fC modification at each location where the modification was identified in the target DNA. In embodiments, the percentages of the T at each transition location provide a quantitative level of 5fC at each location in the target DNA.

Adding a blocking group to the 5caC in the DNA sample can be accomplished by (i) contacting the DNA sample with a coupling agent, for example a carboxylic acid derivatization reagent like carbodiimide derivatives such as 1-ethyl-3-(3-dimethylaminopropyl)carbodiimide (EDC) or N,N'-dicyclohexylcarbodiimide (DCC) and (ii) contacting the DNA sample with an amine, hydrazine or hydroxylamine compound. Thus, for example, 5caC can be blocked by treating the DNA sample with EDC and then benzylamine, ethylamine or other amine to form an amide that blocks 5caC from conversion to DHU by, e.g., pic-$BH_3$. Methods for EDC-catalyzed 5caC coupling are described in WO2014165770, and are incorporated herein by reference.

The method for identifying 5fC can be performed on an RNA sample to identify the location of, and provide a quantitative measure of, 5fC in a target RNA.

Nucleic Acid Sample/Target Nucleic Acid

The present invention provides methods for identifying the location of one or more of 5-methylcytosine, 5-hydroxymethylcytosine, 5-carboxylcytosine and/or 5-formylcytosine in a target nucleic acid quantitatively with base-resolution without affecting the unmodified cytosine. In embodiments, the target nucleic acid is DNA. In other embodiments, the target nucleic acid is RNA. Likewise the nucleic acid sample that comprises the target nucleic acid may be a DNA sample or an RNA sample.

The target nucleic acid may be any nucleic acid having cytosine modifications (i.e., 5mC, 5hmC, 5fC, and/or 5caC). The target nucleic acid can be a single nucleic acid molecule in the sample, or may be the entire population of nucleic acid molecules in a sample (or a subset thereof). The target nucleic acid can be the native nucleic acid from the source (e.g., cells, tissue samples, etc.) or can be pre-converted into a high-throughput sequencing-ready form, for example by fragmentation, repair and ligation with adaptors for sequencing. Thus, target nucleic acids can comprise a plurality of nucleic acid sequences such that the methods described herein may be used to generate a library of target nucleic acid sequences that can be analyzed individually (e.g., by determining the sequence of individual targets) or in a group (e.g., by high-throughput or next generation sequencing methods).

A nucleic acid sample can be obtained from an organism from the Monera (bacteria), Protista, Fungi, Plantae, and Animalia Kingdoms. Nucleic acid samples may be obtained from a from a patient or subject, from an environmental sample, or from an organism of interest. In embodiments, the nucleic acid sample is extracted or derived from a cell or collection of cells, a body fluid, a tissue sample, an organ, and an organelle.

RNA Sample/Target RNA

The present invention provides methods for identifying the location of one or more of 5-methylcytosine, 5-hydroxymethylcytosine, 5-carboxylcytosine and/or 5-formylcytosine in a target RNA quantitatively with base-resolution without affecting the unmodified cytosine. In embodiments, the RNA is one or more of mRNA (messenger RNA), tRNA (transfer RNA), rRNA (ribosomal RNA), snRNA (small nuclear RNA), miRNA (microRNA), lncRNA (long non-coding RNA) and eRNA (enhancer RNA). The target RNA can be a single RNA molecule in the sample, or may be the entire population of RNA molecules in a sample (or a subset thereof). Thus, target RNA can comprise a plurality of RNA sequences such that the methods described herein may be used to generate a library of target RNA sequences that can be analyzed individually (e.g., by determining the sequence of individual targets) or in a group (e.g., by high-throughput or next generation sequencing methods).

DNA Sample/Target DNA

The methods of the invention utilize mild enzymatic and chemical reactions that avoid the substantial degradation associated with methods like bisulfate sequencing. Thus, the methods of the present invention are useful in analysis of low-input samples, such as circulating cell-free DNA and in single-cell analysis.

In embodiments of the invention, the DNA sample comprises picogram quantities of DNA. In embodiments of the invention, the DNA sample comprises about 1 pg to about 900 pg DNA, about 1 pg to about 500 pg DNA, about 1 pg to about 100 pg DNA, about 1 pg to about 50 pg DNA, about 1 to about 10 pg, DNA, less than about 200 pg, less than about 100 pg DNA, less than about 50 pg DNA, less than about 20 pg DNA, and less than about 5 pg DNA. In other embodiments of the invention, the DNA sample comprises nanogram quantities of DNA. The sample DNA for use in the methods of the invention can be any quantity including, DNA from a single cell or bulk DNA samples. In embodiments, the methods of the present invention can be performed on a DNA sample comprising about 1 to about 500 ng of DNA, about 1 to about 200 ng of DNA, about 1 to about 100 ng of DNA, about 1 to about 50 ng of DNA, about 1 to about 10 ng of DNA, about 2 to about 5 ng of DNA, less than about 100 ng of DNA, less than about 50 ng of DNA less than 5 ng, and less than 2 ng of DNA. In embodiments of the invention the DNA sample comprises microgram quantities of DNA.

A DNA sample used in the methods described herein may be from any source including, for example a body fluid, tissue sample, organ, organelle, or single cells. In embodiments, the DNA sample is circulating cell-free DNA (cell-free DNA or cfDNA), which is DNA found in the blood and is not present within a cell. cfDNA can be isolated from blood or plasma using methods known in the art. Commercial kits are available for isolation of cfDNA including, for example, the Circulating Nucleic Acid Kit (Qiagen). The DNA sample may result from an enrichment step, including, but is not limited to antibody immunoprecipitation, chromatin immunoprecipitation, restriction enzyme digestion-based enrichment, hybridization-based enrichment, or chemical labeling-based enrichment.

The target DNA may be any DNA having cytosine modifications (i.e., 5mC, 5hmC, 5fC, and/or 5caC) including, but not limited to, DNA fragments or genomic DNA purified from tissues, organs, cells and organelles. The target DNA can be a single DNA molecule in the sample, or may be the entire population of DNA molecules in a sample (or a subset thereof). The target DNA can be the native DNA from the source or pre-converted into a high-throughput sequencing-ready form, for example by fragmentation, repair and ligation with adaptors for sequencing. Thus, target DNA can comprise a plurality of DNA sequences such that the methods described herein may be used to generate a library of target DNA sequences that can be analyzed individually (e.g., by determining the sequence of individual targets) or in a group (e.g., by high-throughput or next generation sequencing methods).

Converting 5mC and 5hmC to 5caC and/or 5fC

Embodiments of the present invention, such as the TAPS method described herein, include the step of converting the 5mC and 5hmC (or just the 5mC if the 5hmC is blocked) to 5caC and/or 5fC. In embodiments of the invention, this step comprises contacting the DNA or RNA sample with a ten eleven translocation (TET) enzyme. The TET enzymes are a family of enzymes that catalyze the transfer of an oxygen molecule to the N5 methyl group on 5mC resulting in the formation of 5-hydroxymethylcytosine (5hmC). TET further catalyzes the oxidation of 5hmC to 5fC and the oxidation of 5fC to form 5caC (see FIG. 5A). TET enzymes useful in the methods of the invention include one or more of human TET1, TET2, and TET3; murine Tet1, Tet2, and Tet3; *Naegleria* TET (NgTET); *Coprinopsis cinerea* (CcTET) and derivatives or analogues thereof. In embodiments, the TET enzyme is NgTET. In other embodiments the TET enzyme is human TET1 (hTET1).

Converting 5caC and/or 5fC to DHU

Methods of the present invention include the step of converting the 5caC and/or 5fC in a nucleic acid sample to DHU. In embodiments of the invention, this step comprises contacting the DNA or RNA sample with a reducing agent including, for example, a borane reducing agent such as pyridine borane, 2-picoline borane (pic-BH$_3$), borane, sodium borohydride, sodium cyanoborohydride, and sodium triacetoxyborohydride. In a preferred embodiment, the reducing agent is pyridine borane and/or pic-BH$_3$.

Amplifying the Copy Number of Modified Target Nucleic Acid

The methods of the invention may optionally include the step of amplifying (increasing) the copy number of the modified target Nucleic acid by methods known in the art. When the modified target nucleic acid is DNA, the copy number can be increased by, for example, PCR, cloning, and primer extension. The copy number of individual target DNAs can be amplified by PCR using primers specific for a particular target DNA sequence. Alternatively, a plurality of different modified target DNA sequences can be amplified by cloning into a DNA vector by standard techniques. In embodiments of the invention, the copy number of a plurality of different modified target DNA sequences is increased by PCR to generate a library for next generation sequencing where, e.g., double-stranded adapter DNA has been previously ligated to the sample DNA (or to the modified sample DNA) and PCR is performed using primers complimentary to the adapter DNA.

Detecting the Sequence of the Modified Target Nucleic Acid

In embodiments of the invention, the method comprises the step of detecting the sequence of the modified target nucleic acid. The modified target DNA or RNA contains DHU at positions where one or more of 5mC, 5hmC, 5fC, and 5caC were present in the unmodified target DNA or RNA. DHU acts as a T in DNA replication and sequencing methods. Thus, the cytosine modifications can be detected by any direct or indirect method that identifies a C to T transition known in the art. Such methods include sequencing methods such as Sanger sequencing, microarray, and next generation sequencing methods. The C to T transition can also be detected by restriction enzyme analysis where the C to T transition abolishes or introduces a restriction endonuclease recognition sequence.

Kits

The invention additionally provides kits for identification of 5mC and 5hmC in a target DNA. Such kits comprise reagents for identification of 5mC and 5hmC by the methods described herein. The kits may also contain the reagents for identification of 5caC and for the identification of 5fC by the methods described herein. In embodiments, the kit comprises a TET enzyme, a borane reducing agent and instructions for performing the method. In further embodiments, the TET enzyme is TET1 and the borane reducing agent is selected from one or more of the group consisting of pyridine borane, 2-picoline borane (pic-BH$_3$), borane, sodium borohydride, sodium cyanoborohydride, and sodium triacetoxyborohydride. In a further embodiment, the TET1 enzyme is NgTet1 or murine Tet1 and the borane reducing agent is pyridine borane and/or pic-BH$_3$.

In embodiments, the kit further comprises a 5hmC blocking group and a glucosyltransferase enzyme. In further embodiments, the 5hmC blocking group is uridine diphosphate (UDP)-sugar where the sugar is glucose or a glucose derivative, and the glucosyltransferase enzyme is T4 bacteriophage β-glucosyltransferase (βGT), T4 bacteriophage α-glucosyltransferase (αGT), and derivatives and analogs thereof.

In embodiments the kit further comprises an oxidizing agent selected from potassium perruthenate (KRuO4) and/or Cu(II)/TEMPO (copper(II) perchlorate and 2,2,6,6-tetramethylpiperidine-1-oxyl (TEMPO)).

In embodiments, the kit comprises reagents for blocking 5fC in the nucleic acid sample. In embodiments, the kit comprises an aldehyde reactive compound including, for example, hydroxylamine derivatives, hydrazine derivatives, and hyrazide derivatives as described herein. In embodiments, the kit comprises reagents for blocking 5caC as described herein.

In embodiments, the kit comprises reagents for isolating DNA or RNA. In embodiments the kit comprises reagents for isolating low-input DNA from a sample, for example cfDNA from blood, plasma, or serum.

EXAMPLES

Methods

Preparation of Model DNA.

DNA oligos for MALDI and HPLC-MS/MS test. DNA oligonucleotides ("oligos") with C, 5mC and 5hmC were purchased from Integrated DNA Technologies (IDT). All the sequences and modifications could be found in FIGS. 6 and 7. DNA oligo with 5fC was synthesized by the C-tailing method: DNA oligos 5'-GTCGACCGGATC-3' (SEQ ID NO: 1) and 5'-TTGGATCCGGTCGACTT-3' (SEQ ID NO: 2) were annealed and then incubated with 5-formyl-2'-dCTP (Trilink Biotech) and Klenow Fragment 3'→5' exo- (New England Biolabs) in NEBuffer 2 for 2 hr at 37° C. The product was purified with Bio-Spin P-6 Gel Columns (Bio-Rad).

DNA oligo with 5caC was synthesized using Expedite 8900 Nucleic Acid Synthesis System with standard phosphoramidites (Sigma) 5-Carboxy-dC-CE Phosphoramidite (Glen Research). Subsequent deprotection and purification were carried out with Glen-Pak Cartridges (Glen Research) according to the manufacturer's instructions. Purified oligonucleotides were characterized by Voyager-DE MALDI-TOF (matrix-assisted laser desorption ionization time-of-flight) Biospectrometry Workstation.

222 bp Model DNA for conversion test. To generate 222 bp model DNA containing five CpG sites, bacteriophage lambda DNA (Thermo Fisher) was PCR amplified using Taq DNA Polymerase (New England Biolabs) and purified by AMPure XP beads (Beckman Coulter). Primers sequences are as follows: FW-5'-CCTGATGAAACAAGCATGTC-3' (SEQ ID NO: 3), RV-5'-CAUTACTCACUTCCCCACUT-3' (SEQ ID NO: 4). The uracil base in the reverse strand of PCR product was removed by USER enzyme (New England Biolabs). 100 ng of purified PCR product was then methylated in 20 μl solution containing 1× NEBuffer 2, 0.64 mM S-adenosylmethionine and 20 U M.SssI CpG Methyltransferase (New England Biolabs) for 2 hr at 37° C., followed by 20 min heat inactivation at 65° C. The methylated 222 bp model DNA was purified by AMPure XP beads.

Model DNA for TAPS, TAPSβ and CAPS validation with Sanger sequencing. 34 bp DNA oligo containing single 5mC and single 5hmC site was annealed with other DNA oligos in annealing buffer containing 5 mM Tris-Cl (pH 7.5), 5 mM $MgCl_2$, and 50 mM NaCl, and then ligated in a reaction containing 400 U T4 ligase (NEB) at 25° C. for 1 hr and purified by 1.8× AMPure XP beads.

| DNA | Sequence (5' to 3') |
|---|---|
| 34 bp mC and hmC | CCCGA$^m$CGCATGATCTGTACTTGATCGAC$^{hm}$CGTGCAAC_ (SEQ ID NO: 5) |
| TruSeq Universal Adapter | AATGATACGGCGACCACCGAGATCTACACTCTTTCCCT ACACGACGCTCTTCCGATCT (SEQ ID NO: 6) |
| TruSeq Adapter (Index 6) | /5Phos/GATCGGAAGAGCACACGTCTGAACTCCAGTCAC GCCAATATCTCGTATGCCGTCTTCTGCTTG (SEQ ID NO: 7) |
| Uracil linker | TCTTCCGAUCGUUGCACGGUCGATCAAGUACAGATCAT GCGUCGGGAGAUCGGAAG (SEQ ID NO: 8) |

The Uracil linker was removed by USER enzyme after ligation reaction resulting in a final product sequence (5' to 3'): AATGATACGGCGACCACCGAGATCTACACTCTTTCCCTACACGACGCTCTTCCGA TCTCCCGA$^m$CGCATGATCTGTACTTGATCGAC$^{hm}$CGTGCAACGATCGGAAGAGCA CACGTCTGAACTCCAGTCACGCCAATATCTCGTATGCCGTCTTCTGCTTG (SEQ ID NO: 9). PCR primers for amplification of the model DNA were: P5: 5'-AATGATACGGCGACCACCGAG-3' (SEQ ID NO: 10) and P7: 5'-CAAGCAGAAGACGGCATACGAG-3' (SEQ ID NO: 11).

Model DNA for polymerase test and Sanger sequencing. Model DNA for polymerase test and Sanger sequencing was prepared with the same ligation method above except different DNA oligos were used:

| DNA | Sequence (5' to 3') |
|---|---|
| 34 bp mC | AGCAGTCT$^m$CGATCAGCTG$^m$CTACTG TA$^m$CGTAGCAT (SEQ ID NO: 12) |
| TruSeq Universal Adapter | AATGATACGGCGACCACCGAGATCTACAC TCTTTCCCTACACGACGCTCTTCCGATCT (SEQ ID NO: 13) |
| TruSeq Adapter (Index 6) | /5Phos/GATCGGAAGAGCACACGTCTGAACTCCA GTCACGCCAATATCTCGTATGCCGTCTTCTGCTTG (SEQ ID NO: 14) |
| Insert_1_40_bp | /5Phos/AGGTGCGCTAAGTTCTAGATCGCCAACT GGTTGTGGCCTT (SEQ ID NO: 15) |
| Insert_2_60_bp | /5Phos/CTATAGCCGGCTTGCTCTCTCTGCCTC TAGCAGCTGCTCCCTATAGTGAGTCGTATTAAC (SEQ ID NO: 16) |
| 40_bp-Linker-1 | ATCTAGAACTTAGCGCACCTAGATCGGAAGAGCGT CGTGT (SEQ ID NO: 17) |
| 80_bp-Linker: | AGAGAGCAAGCCGGCTATAGATGCTACGTACAGTAGC AGCTGATCAAGACTGCTAAGGCCACAACCAGTTGGCG (SEQ ID NO: 18) |
| 42_bp-Linker-2: | AGACGTGTGCTCTTCCGATCGTTAATACGACTCACTA TAGGG (SEQ ID NO: 19) |

The final product sequence (5' to 3') was: AATGATACGGCGACCACCGAGATCTACACTCTTTCCCTACACGACGCTCTTCCGA TCTAGGTGCGCTAAGTTCTAGATCGCCAACTGGTTGTGGCCTTAGCAGTCT$^m$CGA TCAGCTG$^m$CTACTGTA$^m$CGTAGCATCTATAGCCGGCTTGCTCTCTCTGCCTCTAGC AGCTGCTCCCTATAGTGAGTCGTATTAACGATCGGAAGAGCACACGTCTGAACTC CAGTCACGCCAATATCTCGTATGCCGTCTTCTGCTTG (SEQ ID NO: 20). PCR primers to amplify the model DNA are the P5 and P7 primers provided above. Biotin-labelled primer sequence for primer extension is biotin linked to the 5' end of the P7 primer. PCR primers for RT-PCR after T7 RNA polymerase transcription were the P5 primer and RT: 5'-TGCTAGAGGCAGAGAGAGCAAG-3' (SEQ ID NO: 21).

Model DNA for PCR bias test. Model DNA for PCR bias test was prepared with the same ligation method above except different DNA oligos were used:

| DNA | Sequence (5' to 3') |
|---|---|
| 17 bp X | AGCAGTCTXGATCAGCT (SEQ ID NO: 22) (X = DHU or U or T or C) |
| 17 bp No Modification | GCTACTGTACGTAGCAT (SEQ ID NO: 23) |
| TruSeq Universal Adapter | AATGATACGGCGACCACCGAGATCTACAC TCTTTCCCTACACGACGCTCTTCCGATCT (SEQ ID NO: 24) |
| TruSeq Adapter (Index 6) | /5Phos/GATCGGAAGAGCACACGTCTGAACTCCA GTCACGCCAATATCTCGTATGCCGTCTTCTGCTTG (SEQ ID NO: 25) |
| Insert_1_40_bp | /5Phos/AGGTGCGCTAAGTTCTAGATCGCCAACT GGTTGTGGCCTT (SEQ ID NO: 26) |
| Insert_2_60_bp | /5Phos/CTATAGCCGGCTTGCTCTCTCTGCCTCT AGCAGCTGCTCCCTATAGTGAGTCGTATTAAC (SEQ ID NO: 27) |
| 40_bp-Linker-1 | ATCTAGAACTTAGCGCACCTAGATCGGAAGAGCGT CGTGT (SEQ ID NO: 28) |

| DNA | Sequence (5' to 3') |
|---|---|
| 80_bp-Linker | AGAGAGCAAGCCGGCTATAGATGCTACGTACAGTAGC AGCTGATCAAGACTGCTAAGGCCACAACCAGTTGGCG (SEQ ID NO: 29) |
| 42_bp-Linker-2 | AGACGTGTGCTCTTCCGATCGTTAATACGACTCACTA TAGGG (SEQ ID NO: 30) |

Final product sequence (5' to 3'): AATGATACGGCGAC-CACCGAGATCTACACTCTTTCCCTACACGACGCT-CTTCCGA TCTAGGTGCGCTAAGTTCTAGATCGC-CAACTGGTTGTGGCCTTAGCAGTCTXGAT CAGCT-GCTACTGTACGTAGCATCTATAGCCGGCTTGCT-CTCTCTGCCTCTAGCAGC TGCTCCCTATAGT-GAGTCGTATTAACGATCGGAAGAGCACACGTCT-GAACTCCAG TCACGCCAATATCTCGTATGCCGT-CTTCTGCTTG (SEQ ID NO: 31), where X=DHU or U or T or C. PCR primer to amplify the model DNA are the P5 and P7 primers provided above.

Preparation of Methylated Bacteriophage Lambda Genomic DNA

1 µg of unmethylated bacteriophage lambda DNA (Promega) was methylated in 50 µL reaction containing 0.64 mM SAM and 0.8 U/µl M.SssI enzyme in Mg$^{2+}$-free buffer (10 mM Tris-Cl pH 8.0, 50 mM NaCl, and 10 mM EDTA) for 2 hours at 37° C. Then, 0.5 µL of M.SssI enzyme and 1 µL of SAM were added and the reaction was incubated for additional 2 hours at 37° C. Methylated DNA was subsequently purified on 1× Ampure XP beads. To assure complete methylation, the whole procedure was repeated in NEB buffer 2. DNA methylation was then validated with HpaII digestion assay. 50 ng of methylated and unmethylated DNA were digested in 10 µL reaction with 2 U of HpaII enzyme (NEB) in CutSmart buffer (NEB) for 1 h at 37° C. Digestion products were run on 1% agarose gel together with undigested lambda DNA control. Unmethylated lambda DNA was digested after the assay whereas methylated lambda DNA remained intact confirming complete and successful CpG methylation. Sequence of lambda DNA can be found in GenBank—EMBL Accession Number: J02459.

Preparation of 2 kb Unmodified Spike-in Controls 2 kb spike-in controls (2 kb-1, 2, 3) were PCR amplified from pNIC28-Bsa4 plasmid (Addgene, cat. no. 26103) in the reaction containing 1 ng DNA template, 0.5 µM primers, 1 U Phusion High-Fidelity DNA Polymerase (Thermo Fisher). PCR primer sequences are listed in Table 2.

TABLE 2

Sequences of PCR primers for spike-ins.

| Primer name | Sequence (5' to 3') |
|---|---|
| 2kb-3_Forward | CACAGATGTCTGCCTGTTCA (SEQ ID NO: 32) |
| 2kb-3_Reverse | AGGGTGGTGAATGTGAAACC (SEQ ID NO: 33) |

PCR product was purified on Zymo-Spin column. 2 kb unmodified control sequence (5' to 3'):

(SEQ ID NO: 34)
CACAGATGTCTGCCTGTTCATCCGCGTCCAGCTCGTTGAGTTTCTCCAGA
AGCGTTAATGTCTGGCTTCTGATAAAGCGGGCCATGTTAAGGGCGGTTTT
TTCCTGTTTGGTCACTGATGCCTCCGTGTAAGGGGGATTTCTGTTCATGG
GGGTAATGATACCGATGAAACGAGAGAGGATGCTCACGATACGGGTTACT
GATGATGAACATGCCCGGTTACTGGAACGTTGTGAGGGTAAACAACTGGC
GGTATGGATGCGGCGGGACCAGAGAAAAATCACTCAGGGTCAATGCCAGC
GCTTCGTTAATACAGATGTAGGTGTTCCACAGGGTAGCCAGCAGCATCCT
GCGATGCAGATCCGGAACATAATGGTGCAGGGCGCTGACTTCCGCGTTTC
CAGACTTTACGAAACACGGAAACCGAAGACCATTCATGTTGTTGCTCAGG
TCGCAGACGTTTTGCAGCAGCAGTCGCTTCACGTTCGCTCGCGTATCGGT
GATTCATTCTGCTAACCAGTAAGGCAACCCCGCCAGCCTAGCCGGGTCCT
CAACGACAGGAGCACGATCATGCGCACCCGTGGGGCCGCCATGCCGGCGA
TAATGGCCTGCTTCTCGCCGAAACGTTTGGTGGCGGGACCAGTGACGAAG
GCTTGAGCGAGGGCGTGCAAGATTCCGAATACCGCAAGCGACAGGCCGAT
CATCGTCGCGCTCCAGCGAAAGCGGTCCTCGCCGAAAATGACCCAGAGCG
CTGCCGGCACCTGTCCTACGAGTTGCATGATAAAGAAGACAGTCATAAGT
GCGGCGACGATAGTCATGCCCCGCGCCCACCGGAAGGAGCTGACTGGGTT
GAAGGCTCTCAAGGGCATCGGTCGAGATCCCGGTGCCTAATGAGTGAGCT
AACTTACATTAATTGCGTTGCGCTCACTGCCCGCTTTCCAGTCGGGAAAC
CTGTCGTGCCAGCTGCATTAATGAATCGGCCAACGCGCGGGGAGAGGCGG
TTTGCGTATTGGGCGCCAGGGTGGTTTTTCTTTTCACCAGTGAGACGGGC
AACAGCTGATTGCCCTTCACCGCCTGGCCCTGAGAGAGTTGCAGCAAGCG
GTCCACGCTGGTTTGCCCCAGCAGGCGAAAATCCTGTTTGATGGTGGTTA
ACGGCGGGATATAACATGAGCTGTCTTCGGTATCGTCGTATCCCACTACC
GAGATATCCGCACCAACGCGCAGCCCGGACTCGGTAATGGCGCGCATTGC
GCCCAGCGCCATCTGATCGTTGGCAACCAGCATCGCAGTGGGAACGATGC
CCTCATTCAGCATTTGCATGGTTTGTTGAAAACCGGACATGGCACTCCAG
TCGCCTTCCCGTTCCGCTATCGGCTGAATTTGATTGCGAGTGAGATATTT
ATGCCAGCCAGCCAGACGCAGACGCGCCGAGACAGAACTTAATGGGCCCG
CTAACAGCGCGATTTGCTGGTGACCCAATGCGACCAGATGCTCCACGCCC
AGTCGCGTACCGTCTTCATGGGAGAAAATAATACTGTTGATGGGTGTCTG
GTCAGAGACATCAAGAAATAACGCCGGAACATTAGTGCAGGCAGCTTCCA
CAGCAATGGCATCCTGGTCATCCAGCGGATAGTTAATGATCAGCCCACTG
ACGCGTTGCGCGAGAAGATTGTGCACCGCCGCTTTACAGGCTTCGACGCC
GCTTCGTTCTACCATCGACACCACCACGCTGGCACCCAGTTGATCGGCGC
GAGATTTAATCGCCGCGACAATTTGCGACGGCGCGTGCAGGGCCAGACTG
GAGGTGGCAACGCCAATCAGCAACGACTGTTTGCCCGCCAGTTGTTGTGC
CACGCGGTTGGGAATGTAATTCAGCTCCGCCATCGCCGCTTCCACTTTTT

-continued

CCCGCGTTTTCGCAGAAACGTGGCTGGCCTGGTTCACCACGCGGGAAACG

GTCTGATAAGAGACACCGGCATACTCTGCGACATCGTATAACGTTACTGG

TTTCACATTCACCACCCT

Preparation of 120Mer Spike-in Controls 120 mer spike-in controls were produced by primer extension. Oligo sequences and primers are listed in the Table 3.

TABLE 3

Sequences of DNA oligos and primers used for preparation of 120 mer control spike-ins.

| Spike-in control | Template sequence (5' to 3') | Primer for extension (5' to 3') |
|---|---|---|
| 120 mer-1 | ATACTCATCATTAAACTTCGCCCTTACCTAC CACTTCGTGTATGTAGATAGGTAGTATACA ATTGATATCGAAATGAGTACGTAGATAGTA GAAAGTAAGATGGAGGTGAGAGTGAGAGT (SEQ ID NO: 35) | ATACTCATCATTAAA CTTCGCCCTTACCTAC CACTTCG (SEQ ID NO: 36) |
| 120 mer-2 | GCGGCGTGATACTGGTCCCGAG5hmCCTGA AGTTAGGCC5hmCGGGATGACTGA5hmCAG TCTTCCGAGACCGACGACACAGGTCTCCCT ATAGTGAGTCGTATTATGGCGAGAGAATGA ATCTCCATC (SEQ ID NO: 37) | GATGGAGATTCATTC TCTCGCCA TAATACGACTCACTA TAGG (SEQ ID NO: 38) |

Briefly, for 120 mer-1 spike-in, 3 μM oligo was annealed with 10 μM primer in the annealing buffer containing 5 mM Tris-Cl (pH 7.5), 5 mM MgCl$_2$, and 50 mM NaCl. For 120 mer-2 spike-in, 5 μM oligo was annealed with 7.5 μM primer. Primer extension was performed in the NEB buffer 2 with 0.4 μM dNTPs (120 mer-1: dATP/dGTP/dTTP/dhmCTP, 120 mer-2: dATP/dGTP/dTTP/dCTP) and 5 U of Klenow Polymerase (New England Biolabs) for 1 hour at 37° C. After reaction spike-in controls were purified on Zymo-Spin columns (Zymo Research). The 120 mer spike-in controls were then methylated in 50 nt reaction containing 0.64 mM SAM and 0.8 U/μl M.SssI enzyme in NEB buffer 2 for 2 hours at 37° C. and purified with Zymo-Spin columns. All spike-in sequences used can be downloaded from figshare.com/s/80c3ab713c261262494b.

Generation of Synthetic Spike-in with N5mCNN and N5hmCNN

Synthetic oligo with N5mCNN and N5hmCNN sequences was produced by annealing and extension method. Oligo sequences are listed in Table 4, below.

TABLE 4

| Oligo | Template sequence (5' to 3') |
|---|---|
| N5mCNN | GAAGATGCAGAAGACAGGAAGGATGAAA CACTCAGGCGCACGCTGGCATN$^m$CNNGA CAAACCACAAGAACAGGCTAGTGAGAAT GAAGGGA (SEQ ID NO: 39) |
| N5hmCNN | CCAACTCTGAAACCCACCAACGCCAACA TCCACCACACAACCCAAGATN$^{hm}$CNNGA CCATCTTACAAACATATCCCTTCATTCTCAC TAGCC (SEQ ID NO: 40) |

Briefly, 10 μM N5mCNN and N5hmCNN oligos (IDT) were annealed together in the annealing buffer containing 5 mM Tris-Cl (pH 7.5), 5 mM MgCl$_2$, and 50 mM NaCl. Extension was performed in the NEB buffer 2 with 0.4 mM dNTPs (dATP/dGTP/dTTP/dCTP) and 5 U of Klenow Polymerase (NEB) for 1 hour at 37° C. After reaction, spike-in control was purified on Zymo-Spin column (Zymo Research). Synthetic spike-in with N5mCNN and N5hmCNN (5' to 3'):

(SEQ ID NO: 41)
GAAGATGCAGAAGACAGGAAGGATGAAACACTCAGGCGCACGCTGGCATN hmCNNGACAAACCACAAGAACAGGCTAGTGAGAATGAAGGGATATGTTTG

TAAGATGGTCNNGNATCTTGGGTTGTGTGGTGGATGTTGGCGTTGGTGGG

TTTCAGAGTTGG.

Complementary strand (5' to 3'):

(SEQ ID NO: 42)
CCAACTCTGAAACCCACCAACGCCAACATCCACCACACAACCCAAGATNh mCNNGACCATCTTACAAACATATCCCTTCATTCTCACTAGCCTGTTCTTG

TGGTTTGTCNNGNATGCCAGCGTGCGCCTGAGTGTTTCATCCTTCCTGTC

TTCTGCATCTTC.

DNA Digestion and HPLC-MS/MS Analysis

DNA samples were digested with 2 U of Nuclease P1 (Sigma-Aldrich) and 10 nM deaminase inhibitor erythro-9-Amino-β-hexyl-α-methyl-9H-purine-9-ethanol hydrochloride (Sigma-Aldrich). After overnight incubation at 37° C., the samples were further treated with 6 U of alkaline phosphatase (Sigma-Aldrich) and 0.5 U of phosphodiesterase I (Sigma-Aldrich) for 3 hours at 37° C. The digested DNA solution was filtered with Amicon Ultra-0.5 mL 10 K centrifugal filters (Merck Millipore) to remove the proteins, and subjected to HPLC-MS/MS analysis.

The HPLC-MS/MS analysis was carried out with 1290 Infinity LC Systems (Agilent) coupled with a 6495B Triple Quadrupole Mass Spectrometer (Agilent). A ZORBAX Eclipse Plus C18 column (2.1×150 mm, 1.8-Micron, Agilent) was used. The column temperature was maintained at 40° C., and the solvent system was water containing 10 mM ammonium acetate (pH 6.0, solvent A) and water-acetonitrile (60/40, v/v, solvent B) with 0.4 mL/min flow rate. The gradient was: 0-5 min; 0 solvent B; 5-8 min; 0-5.63% solvent B; 8-9 min; 5.63% solvent B; 9-16 min; 5.63-13.66% solvent B; 16-17 min; 13.66-100% solvent B; 17-21 min; 100% solvent B; 21-24.3 min; 100-0% solvent B; 24.3-25 min; 0% solvent B. The dynamic multiple reaction monitoring mode (dMRM) of the MS was used for quantification. The source-dependent parameters were as follows: gas temperature 230° C., gas flow 14 L/min, nebulizer 40 psi, sheath gas temperature 400° C., sheath gas flow 11 L/min, capillary voltage 1500 V in the positive ion mode, nozzle voltage 0 V, high pressure RF 110 V and low pressure RF 80 V, both in the positive ion mode. The fragmentor voltage was 380 V for all compounds, while other compound-dependent parameters were as summarized in Table 5.

TABLE 5

Compound-dependent HPLC-MS/MS parameters used for nucleosides quantification.

| Compound | Precursor Ion (m/z) | Product Ion (m/z) | RT (min) | Delta RT (min) | CE (V) | CAE (V) |
| --- | --- | --- | --- | --- | --- | --- |
| dA + H | 252 | 136 | 13.78 | 2 | 10 | 4 |
| dT + H | 243 | 127 | 11.07 | 2 | 10 | 4 |
| dT + Na | 265 | 149 | 11.07 | 2 | 10 | 4 |
| dG + H | 268 | 152 | 9.64 | 2 | 10 | 4 |
| dC + H | 228 | 112 | 3.71 | 1.5 | 10 | 4 |
| dC + Na | 250 | 134 | 3.71 | 1.5 | 10 | 4 |
| mdC + H | 242 | 126 | 9.05 | 1.5 | 10 | 4 |
| mdC + Na | 264 | 148 | 9.05 | 1.5 | 10 | 4 |
| hmdC + H | 258 | 142 | 4.34 | 2 | 12 | 4 |
| hmdC + Na | 280 | 164 | 4.34 | 2 | 12 | 4 |
| fdC + H | 256 | 140 | 10.69 | 2 | 8 | 4 |
| fdC + Na | 278 | 162 | 10.69 | 2 | 8 | 4 |
| cadC + H | 272 | 156 | 1.75 | 3 | 12 | 4 |
| cadC + Na | 294 | 178 | 1.75 | 3 | 12 | 4 |
| DHU + H | 231 | 115 | 3.45 | 3 | 10 | 4 |
| DHU + Na | 253 | 137 | 3.45 | 3 | 10 | 4 |

RT: retention time, CE: collision energy; CAE: cell accelerator voltage.
All the nucleosides were analyzed in the positive mode.

Expression and Purification of NgTET1 pRSET-A plasmid encoding His-tagged NgTET1 protein (GG739552.1) was designed and purchased from Invitrogen. Protein was expressed in *E. coli* BL21 (DE3) bacteria and purified as previously described with some modifications (J. E. Pais et al., Biochemical characterization of a *Naegleria* TET-like oxygenase and its application in single molecule sequencing of 5-methylcytosine. Proc. Natl. Acad. Sci. U.S.A. 112, 4316-4321 (2015), incorporated herein by reference). Briefly, for protein expression bacteria from overnight small-scale culture were grown in LB medium at 37° C. and 200 rpm until OD600 was between 0.7-0.8. Then cultures were cooled down to room temperature and target protein expression was induced with 0.2 mM isopropyl-β-d-1-thiogalactopyranoside (IPTG). Cells were maintained for additional 18 hours at 18° C. and 180 rpm. Subsequently, cells were harvested and re-suspended in the buffer containing 20 mM HEPES (pH 7.5), 500 mM NaCl, 1 mM DTT, 20 mM imidazole, 1 μg/mL leupeptin, 1 μg/mL pepstatin A and 1 mM PMSF. Cells were broken with EmulsiFlex-05 high-pressure homogenizer, and lysate was clarified by centrifugation for 1 hour at 30,000×g and 4° C. Collected supernatant was loaded on Ni-NTA resins and NgTET1 protein was eluted with buffer containing 20 mM HEPES (pH 7.5), 500 mM imidazole, 2 M NaCl, 1 mM DTT. Collected fractions were then purified on HiLoad 16/60 Sdx 75 (20 mM HEPES pH 7.5, 2 M NaCl, 1 mM DTT). Fractions containing NgTET1 were then collected, buffer exchanged to the buffer containing 20 mM HEPES (pH 7.0), 10 mM NaCl, 1 mM DTT, and loaded on HiTrap HP SP column. Pure protein was eluted with the salt gradient, collected and buffer-exchanged to the final buffer containing 20 mM Tris-Cl (pH 8.0), 150 mM NaCl and 1 mM DTT. Protein was then concentrated up to 130 μM, mixed with glycerol (30% v/v) and aliquots were stored at −80° C.

Expression and Purification of mTET1CD mTET1CD catalytic domain (NM_001253857.2, 4371-6392) with N-terminal Flag-tag was cloned into pcDNA3-Flag between KpnI and BamH1 restriction sites. For protein expression, 1 mg plasmid was transfected into 1 L of Expi293F (Gibco) cell culture at density $1×10^6$ cells/mL and cells were grown for 48 h at 37° C., 170 rpm and 5% $CO_2$. Subsequently, cells were harvested by centrifugation, re-suspended in the lysis buffer containing 50 mM Tris-Cl pH=7.5, 500 mM NaCl, 1× cOmplete Protease Inhibitor Cocktail (Sigma), 1 mM PMSF, 1% Triton X-100 and incubated on ice for 20 min. Cell lysate was then clarified by centrifugation for 30 min at 30000×g and 4° C. Collected supernatant was purified on ANTI-FLAG M2 Affinity Gel (Sigma) and pure protein was eluted with buffer containing 20 mM HEPES pH=8.0, 150 mM NaCl, 0.1 mg/mL 3× Flag peptide (Sigma), 1× cOmplete Protease Inhibitor Cocktail (Sigma), 1 mM PMSF. Collected fractions were concentrated and buffer-exchanged to the final buffer containing 20 mM HEPES pH=8.0, 150 mM NaCl and 1 mM DTT. Concentrated protein was mixed with glycerol (30% v/v), frozen in liquid nitrogen and aliquots were stored at −80° C. Activity and quality of recombinant mTET1CD was checked by MALDI Mass Spectrometry analysis. Based on this assay, recombinant mTET1CD is fully active and able to catalyze oxidation of 5mC to 5caC. Any significant digestion of tested model oligo was detected by MALDI confirming that protein is free from nucleases.

TET Oxidation

NgTET1 Oxidation. For Tet oxidation of the 222 bp model DNA oligos, 100 ng of 222 bp DNA was incubated in 20 μl solution containing 50 mM MOPs buffer (pH 6.9), 100 mM ammonium iron (II) sulfate, 1 mM a-ketoglutarate, 2 mM ascorbic acid, 1 mM dithiothreitol (DTT), 50 mM NaCl, and 5 μM NgTET for 1 hr at 37° C. After that, 0.4 U of Proteinase K (New England Biolabs) was added to the reaction mixture and incubated for 30 min at 37° C. The product was purified by Zymo-Spin column (Zymo Research) following manufacturer's instruction.

For NgTET1 oxidation of genomic DNA, 500 ng of genomic DNA were incubated in 50 μl solution containing 50 mM MOPS buffer (pH 6.9), 100 mM ammonium iron (II) sulfate, 1 mM a-ketoglutarate, 2 mM ascorbic acid, 1 mM dithiothreitol, 50 mM NaCl, and 5 μM NgTET1 for 1 hour at 37° C. After that, 4 U of Proteinase K (New England Biolabs) were added to the reaction mixture and incubated for 30 min at 37° C. The product was cleaned-up on 1.8× Ampure beads following the manufacturer's instruction.

mTET1 Oxidation. 100 ng of genomic DNA was incubated in 50 μl reaction containing 50 mM HEPES buffer (pH 8.0), 100 μM ammonium iron (II) sulfate, 1 mM a-ketoglutarate, 2 mM ascorbic acid, 1 mM dithiothreitol, 100 mM NaCl, 1.2 mM ATP and 4 μM mTET1CD for 80 min at 37° C. After that, 0.8 U of Proteinase K (New England Biolabs) were added to the reaction mixture and incubated for 1 hour at 50° C. The product was cleaned-up on Bio-Spin P-30 Gel Column (Bio-Rad) and 1.8× Ampure XP beads following the manufacturer's instruction.

Borane Reduction

Pic-BH$_3$ reduction 25 μL of 5 M α-picoline-borane (pic-BH$_3$, Sigma-Aldrich) in MeOH and 5 μL of 3 M sodium acetate solution (pH 5.2, Thermo Fisher) was added into 20 μL DNA sample and incubated at 60° C. for 1 h. The product was purified by Zymo-Spin column (Zymo Research) following manufacturer's instructions for the 222 bp or by Micro Bio-Spin 6 Columns (Bio-Rad) following manufacturer's instruction for the oligos.

Alternatively, 100 mg of 2-picoline-borane (pic-borane, Sigma-Aldrich) was dissolved in 187 μL of DMSO to give around 3.26 M solution. For each reaction, 25 μL of pic-borane solution and 5 μL of 3 M sodium acetate solution (pH 5.2, Thermo Fisher) were added into 20 μL of DNA sample and incubated for 3 hours at 70° C. The product was purified by Zymo-Spin column for genomic DNA or by Micro Bio-Spin 6 Columns (Bio-Rad) for DNA oligos following the manufacturer's instructions.

Pyridine borane reduction. 50-100 ng of oxidised DNA in 35 μL of water were reduced in 50 μL reaction containing 600 mM sodium acetate solution (pH=4.3) and 1 M pyridine borane for 16 hours at 37° C. and 850 rpm in Eppendorf ThermoMixer. The product was purified by Zymo-Spin column.

Single nucleoside pic-borane reaction. 500 μL of 3.26 M 2-picoline-borane (pic-borane, Sigma-Aldrich) in MeOH and 500 μL of 3 M sodium acetate solution (pH 5.2, Thermo Fisher) were added into 10 mg of 2'-deoxycytidine-5-carboxylic acid sodium salt (Berry&Associates). The mixture was stirred for 1 hour at 60° C. The product was purified by HPLC to give pure compound as white foam. High resolution MS (Q-TOF) m/z [M+Na]+ calculated for $C_9H_{14}N_2O_5Na$: 253.0800; found: 253.0789.

5hmC Blocking

5hmC blocking was performed in 20 μl solution containing 50 mM HEPES buffer (pH 8), 25 mM MgCl$_2$, 200 μM uridine diphosphoglucose (UDP-Glc, New England Biolabs), and 10 U βGT (Thermo Fisher), and 10 μM 5hmC DNA oligo for 1 hr at 37° C. The product was purified by Micro Bio-Spin 6 Columns (Bio-Rad) following manufacturer's instruction.

5fC Blocking

5fC blocking was performed in 100 mM MES buffer (pH 5.0), 10 mM O-ethylhydroxylamine (Sigma-Aldrich), and 10 μM 5fC DNA oligo for 2 hours at 37° C. The product was purified by Micro Bio-Spin 6 Columns (Bio-Rad) following manufacturer's instruction.

5caC Blocking

5caC blocking was performed in 75 mM MES buffer (pH 5.0), 20 mM N-hydroxysuccinimide (NHS, Sigma-Aldrich), 20 mM 1-(3-dimethylaminopropyl)-3-ethylcarbodiimide hydrochloride (EDC, Fluorochem), and 10 μM 5caC DNA oligo at 37° C. for 0.5 h. The buffer was then exchanged to 100 mM sodium phosphate (pH 7.5), 150 mM NaCl using Micro Bio-Spin 6 Columns (Bio-Rad) following manufacturer's instructions. 10 mM ethylamine (Sigma-Aldrich) was added to the oligo and incubated for 1 hour at 37° C. The product was purified by Micro Bio-Spin 6 Columns (Bio-Rad) following manufacturer's instructions.

5hmC Oxidation

46 μL of 5hmC DNA oligo was denatured with 2.5 μL of 1 M NaOH for 30 min at 37° C. in a shaking incubator, then oxidized with 1.5 μL of solution containing 50 mM NaOH and 15 mM potassium perruthenate (KRuO4, Sigma-Aldrich) for 1 hour on ice. The product was purified by Micro Bio-Spin 6 Columns following manufacturer's instructions.

Validation of TAPS Conversion with TaqαI Assay

5mC conversion after TAPS was tested by PCR amplification of a target region which contains TaqαI restriction site (TCGA) and subsequent TaqαI digestion. For example, 5mC conversion in our TAPS libraries can be tested based on 194 bp amplicon containing single TaqαI restriction site that is amplified from CpG methylated lambda DNA spike-in control. PCR product amplified from the 194 bp amplicon is digested with TaqαI restriction enzyme and digestion product is checked on 2% agarose gel. PCR product amplified on unconverted control DNA is digested by TaqαI and shows two bands on the gel. In TAPS-converted sample restriction site is lost due to C-to-T transition, so the 194 bp amplicon would remain intact. Overall conversion level can be assessed based on digested and undigested gel bands quantification and for successful TAPS samples should be higher than 95%.

Briefly, the converted DNA sample was PCR amplified by Taq DNA Polymerase (New England Biolabs) with corresponding primers. The PCR product was incubated with 4 units of TaqαI restriction enzyme (New England Biolabs) in 1× CutSmart buffer (New England Biolabs) for 30 min at 65° C. and checked by 2% agarose gel electrophoresis.

Quantitative Polymerase Chain Reaction (qPCR)

Figure 11:
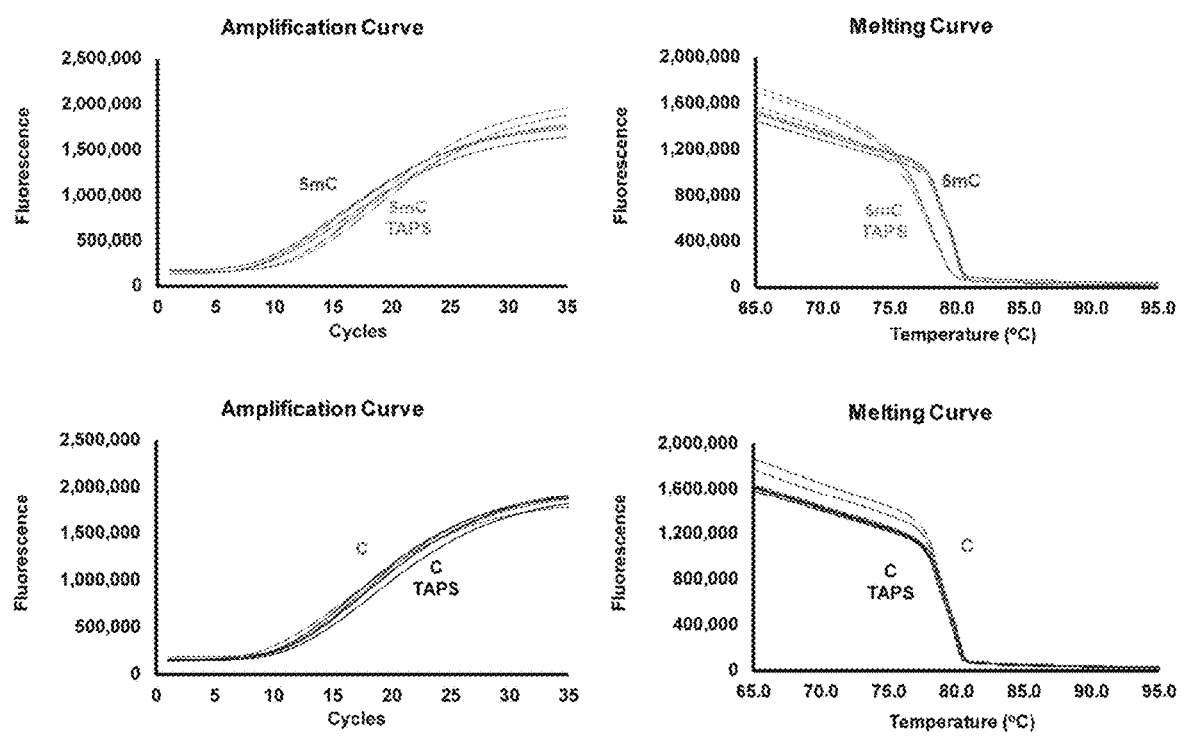
FIG. 11. Comparison of amplification curves and melting curves between model DNAs before and after TAPS. qPCR assay showed minor difference on model DNAs before and after TAPS in amplification curves. Melting curve of methylated DNA (5mC) shifted to lower temperature after TAPS indicated possible Tm-decreasing C-to-T transition while there was no shift for unmethylated DNA (C).

For comparison of amplification curves and melting curves between model DNAs before and after TAPS (FIG. 11), 1 ng of DNA sample was added into 19 μL of PCR master mix containing 1× LightCycler 480 High Resolution Melting Master Mix (Roche Diagnostics Corporation), 250 nM of primers FW-CCTGATGAAACAAGCATGTC (SEQ ID NO: 43) and RV-CATTACTCACTTCCCCACTT (SEQ ID NO: 44) and 3 mM of MgSO$_4$. For PCR amplification, an initial denaturation step was performed for 10 min at 95° C., followed by 40 cycles of 5 sec denaturation at 95° C., 5 sec annealing at customized annealing temperature and 5 sec elongation at 72° C. The final step included 1 min at 95° C., 1 min at 70° C. and a melting curve (0.02° C. step increments, 5 sec hold before each acquisition) from 65° C. to 95° C.

For other assays, qPCR was performed by adding the required amount of DNA sample into 19 μL of PCR master mix containing 1× Fast SYBR Green Master Mix (Thermo Fisher), 200 nM of forward and reverse primers. For PCR amplification, an initial denaturation step was performed for 20 sec at 95° C., followed by 40 cycles of 3 s denaturation at 95° C., 20 s annealing and elongation at 60° C.

Validation of $C_mCGG$ Methylation Level in mESC gDNA with HpaII-qPCR Assay.

1 μg mESC gDNA was incubated with 50 units of HpaII (NEB, 50 units/μL) and 1× CutSmart buffer in 50 μL reaction for 16 hours at 37° C. No HpaII was added for control reaction. 1 μL Proteinase K was added to the reaction and incubated at 40° C. for 30 minutes followed by inactivation of Proteinase K for 10 minutes at 95° C. Ct value of HpaII digested sample or control sample was measured by qPCR assay as above with corresponding primer sets for specific CCGG positions (listed in Table 9).

Sanger Sequencing

The PCR product was purified by Exonuclease I and Shrimp Alkaline Phosphatase (New England Biolabs) or Zymo-Spin column and processed for Sanger sequencing.

DNA Damage Test on Fragments with Different Length.

mESC genomic DNA was spiked-in with 0.5% of CpG methylated lambda DNA and left unfragmented or sonicated with Covaris M220 instrument and size-selected to 500-1 kb or 1 kb-3 kb on Ampure XP beads. 200 ng of DNA were single-oxidised with mTET1CD and reduced with Pyridine borane complex as described above or converted with EpiTect Bisulfite Kit (Qiagen) according to manufacturer's protocol. 10 ng of DNA before and after TAPS and Bisulfite conversion were run on 1% agarose gel. To visualize bisulfite converted gel was cooled down for 10 min samples in ice bath. 5mC conversion in TAPS samples was tested by TaqαI digestion assay as described above.

mESCs Culture and Isolation of Genomic DNA

Mouse ESCs (mESCs) E14 were cultured on gelatin-coated plates in Dulbecco's Modified Eagle Medium (DMEM) (Invitrogen) supplemented with 15% FBS (Gibco), 2 mM L-glutamine (Gibco), 1% non-essential amino acids (Gibco), 1% penicillin/streptavidin (Gibco), 0.1 mM β-mercaptoethanol (Sigma), 1000 units/mL LIF (Millipore), 1 µM PD0325901 (Stemgent), and 3 µM CHIR99021 (Stemgent). Cultures were maintained at 37° C. and 5% $CO_2$ and passaged every 2 days.

For isolation of genomic DNA, cells were harvested by centrifugation for 5 min at 1000×g and room temperature. DNA was extracted with Quick-DNA Plus kit (Zymo Research) according to manufacturer's protocol.

Preparation of mESC gDNA for TAPS and WGBS.

For whole-genome bisulfite sequencing (WGBS), mESC gDNA was spiked-in with 0.5% of unmethylated lambda DNA. For whole-genome TAPS, mESC gDNA was spiked-in with 0.5% of methylated lambda DNA and 0.025% of unmodified 2 kb spike-in control. DNA samples were fragmented by Covaris M220 instrument and size-selected to 200-400 bp on Ampure XP beads. DNA for TAPS was additionally spiked-in with 0.25% of N5mCNN and N5hmCNN control oligo after size-selection with Ampure XP beads.

Whole Genome Bisulfite Sequencing

For Whole Genome Bisulfite Sequencing (WGBS), 200 ng of fragmented mESC gDNA spiked-in with 0.5% of unmethylated bacteriophage lambda DNA was used. End-repaired and A-tailing reaction and ligation of methylated adapter (NextFlex) were prepared with KAPA HyperPlus kit (Kapa Biosystems) according to manufacturer's protocol. Subsequently, DNA underwent bisulfite conversion with EpiTect Bisulfite Kit (Qiagen) according to Illumina's protocol. Final library was amplified with KAPA Hifi Uracil Plus Polymerase (Kapa Biosystems) for 6 cycles and cleaned-up on 1× Ampure beads. WGBS sequencing library was paired-end 80 bp sequenced on a NextSeq 500 sequencer (Illumina) using a NextSeq High Output kit with 15% PhiX control library spike-in.

Whole-Genome TAPS

For whole genome TAPS, 100 ng of fragmented mESC gDNA spiked-in with 0.5% of methylated lambda DNA and 0.025% of unmodified 2 kb spike-in control were used. End-repair and A-tailing reaction and ligation of Illumina Multiplexing adapters were prepared with KAPA HyperPlus kit according to manufacturer's protocol. Ligated DNA was oxidized with mTET1CD twice and then reduced with pyridine borane according to the protocols described above. Final sequencing library was amplified with KAPA Hifi Uracil Plus Polymerase for 5 cycles and cleaned-up on 1× Ampure beads. Whole-genome TAPS sequencing library was paired-end 80 bp sequenced on a NextSeq 500 sequencer (Illumina) using one NextSeq High Output kit with 1% PhiX control library spike-in.

Low-Input Whole-Genome TAPS with dsDNA Library Preparation Kits mESC gDNA prepared as described above for whole-genome TAPS was used for low-input whole-genome TAPS. Briefly, samples containing 100 ng, 10 ng, and 1 ng of mESC gDNA were oxidized with NgTET1 once according to the protocol described above. End-repaired and A-tailing reaction and ligation were performed with NEBNext Ultra II (New England Biolabs) or KAPA HyperPlus kit according to manufacturer's protocol. Subsequently DNA underwent pic-borane reaction as described above. Converted libraries were amplified with KAPA Hifi Uracil Plus Polymerase and cleaned-up on 1× Ampure beads.

Low-Input Whole-Genome TAPS with ssDNA Library Preparation Kit mESC gDNA prepared as described above for whole-genome TAPS was used for low-input whole-genome TAPS. Briefly, samples containing 100 ng, 10 ng, 1 ng, 100 pg, and 10 pg of mESC gDNA were oxidized with NgTET1 once and reduced with pic-borane as described above. Sequencing libraries were prepared with Accel-NGS Methyl-Seq DNA Library Kit (Swift Biosciences) according to manufacturer's protocol. Final libraries were amplified with KAPA Hifi Uracil Plus Polymerase for 6 cycles (100 ng), 9 cycles (10 ng), 13 cycles (1 ng), 16 cycles (100 pg), and 21 cycles (10 pg) and cleaned-up on 0.85× Ampure beads.

In other experiments, mESC gDNA prepared as described above for whole-genome TAPS were used for low-input whole-genome TAPS. Briefly, samples containing 100 ng, 10 ng, and 1 ng of mESC gDNA were used for End-repaired and A-tailing reaction and ligated to Illumina Multiplexing adaptors with KAPA HyperPlus kit according to manufacturer's protocol. Ligated samples were then oxidized with mTET1CD once and then reduced with pyridine borane according to the protocols described above. Converted libraries were amplified with KAPA Hifi Uracil Plus Polymerase for 5 cycles (100 ng), 8 cycles (10 ng), and 13 cycles (1 ng) and cleaned-up on 1× Ampure XP beads.

Cell-Free DNA TAPS

Cell-free DNA TAPS samples were prepared from 10 ng and 1 ng of cell-free DNA sample. Briefly, samples were oxidized with NgTET1 once and reduced with pic-borane as described above. Sequencing libraries were prepared with Accel-NGS Methyl-Seq DNA Library Kit (Swift Biosciences) according to manufacturer's protocol. Final libraries were amplified with KAPA Hifi Uracil Plus Polymerase for 9 cycles (10 ng) and 13 cycles (1 ng) and cleaned-up on 0.85× Ampure beads.

In other experiments, cell-free DNA TAPS samples were prepared from 10 ng and 1 ng of cell-free DNA sample as described above for whole-genome TAPS. Briefly, cell-free DNA samples were used for End-repaired and A-tailing reaction and ligated to Illumina Multiplexing adaptors with KAPA HyperPlus kit according to manufacturer's protocol. Ligated samples were then oxidized with mTET1CD once and then reduced with pyridine borane according to the protocols described above. Converted libraries were amplified with KAPA Hifi Uracil Plus Polymerase for 7 cycles (10 ng), and 13 cycles (1 ng) and cleaned-up on 1× Ampure XP beads.

WGBS Data Processing

Paired-end reads were download as FASTQ from Illumina BaseSpace and subsequently quality-trimmed with Trim Galore! v0.4.4 (https://www.bioinformatics.babraham.ac.uk/projects/trim_galore/). Read pairs where at least one read was shorter than 35 bp after trimming were removed. Trimmed reads were mapped to a genome combining the mm9 version of the mouse genome, lambda phage and PhiX (sequence from Illumina iGENOMES) using Bismark v0.19 using --no_overlap option (F. Krueger, S. R. Andrews, Bismark: a flexible aligner and methylation caller for Bisulfite-Seq applications. *Bioinformatics* 27, 1571-1572

(2011), incorporated herein by reference). The 'three-C' filter was used to remove reads with excessive non-conversion rates. PCR duplicates were called using Picard v1.119 (http://broadinstitute.github.io/picard/) MarkDuplicates. Regions known to be prone to mapping artefacts were downloaded (https://sites.google.com/site/anshulkundaje/projects/blacklists) and excluded from further analysis (E. P. Consortium, An integrated encyclopedia of DNA elements in the human genome. *Nature* 489, 57-74 (2012), incorporated herein by reference).

TAPS Data Pre-Processing

Paired-end reads were downloaded from Illumina BaseSpace and subsequently quality-trimmed with Trim Galore! v0.4.4. Read pairs where at least one read was shorter than 35 bp after trimming were removed. Trimmed reads were mapped to a genome combining spike-in sequences, lambda phage and the mm9 version of the mouse genome using BWA mem v.0.7.15 (H. Li, R. Durbin, Fast and accurate short read alignment with Burrows-Wheeler transform. *Bioinformatics* 25, 1754-1760 (2009), incorporated herein by reference) with default parameters. Regions known to be prone to mapping artefacts were downloaded (https://sites.google.com/site/anshulkundaje/projects/blacklists) and excluded from further analysis (E. P. Consortium, *Nature* 489, 57-74 (2012)).

Detection of Converted Bases in TAPS

Aligned reads were split into original top (OT) and original bottom (OB) strands using a custom python3 script (MF-filter.py). PCR duplicates were then removed with Picard MarkDuplicates on OT and OB separately. Overlapping segments in read pairs were removed using BamUtil clipOverlap (https://github.com/statgen/bamUtil) on the deduplicated, mapped OT and OB reads separately. Modified bases were then detected using samtools mpileup and a custom python3 script (MF-caller_MOD.py).

Sequencing Quality Analysis of TAPS and WGBS

Quality score statistics per nucleotide type were extracted from original FASTQ files as downloaded from Illumina BaseSpace with a python3 script (MF-phredder.py).

Coverage Analysis of TAPS and WGBS

Per-base genome coverage files were generated with Bedtools v2.25 genomecov (A. R. Quinlan, I. M. Hall, BEDTools: a flexible suite of utilities for comparing genomic features. Bioinformatics 26, 841-842 (2010), incorporated herein by reference). To compare the relative coverage distributions between TAPS and WGBS, TAPS reads were subsampled to the corresponding coverage median in WGBS using the -s option of samtools view. In the analyses comparing coverage in WGBS and subsampled TAPS, clipOverlap was used on both TAPS and WGBS bam files.

Analysis of Cytosine Modifications Measured by TAPS and WGBS

The fraction of modified reads per base was calculated from Bismark output, and the output of MF-caller_MOD.py, respectively. Intersections were performed using Bedtools intersect, and statistical analyses and figures were generated in R and Matlab. Genomic regions were visualized using IGV v2.4.6 (J. T. Robinson et al., Integrative genomics viewer. *Nat. Biotechnol.* 29, 24-26 (2011), incorporated herein by reference). To plot the coverage and modification levels around CGIs, all CGI coordinates for mm9 were downloaded from the UCSC genome browser, binned into 20 windows, and extended by up to 50 windows of size 80 bp on both sides (as long as they did not reach half the distance to the next CGI). Average modification levels (in CpGs) and coverage (in all bases, both strands) in each bin were computed using Bedtools map. The values for each bin were again averaged and subsequently plotted in Matlab.

Data Processing Time Simulation

Synthetic pair-end sequencing reads were simulated using ART42 based on the lambda phage genome (with parameters -p -ss NS50--errfree --minQ 15-k 0-nf 0-l 75-c 1000000-m 240-s 0-ir 0-ir2 0-dr 0-dr2 0-sam -rs 10). 50% of all CpG positions were subsequently marked as modified and two libraries were produced, either as TAPS (convert modified bases) or as WGBS (convert unmodified bases), using a custom python3 script. The reads were then processed following the pipeline used for each of the methods in the paper. Processing time was measured with Linux command time. All steps of the analysis were performed in single-threaded mode on one Intel Xeon CPU with 250 GB of memory.

Results and Discussion

Figure 3A:
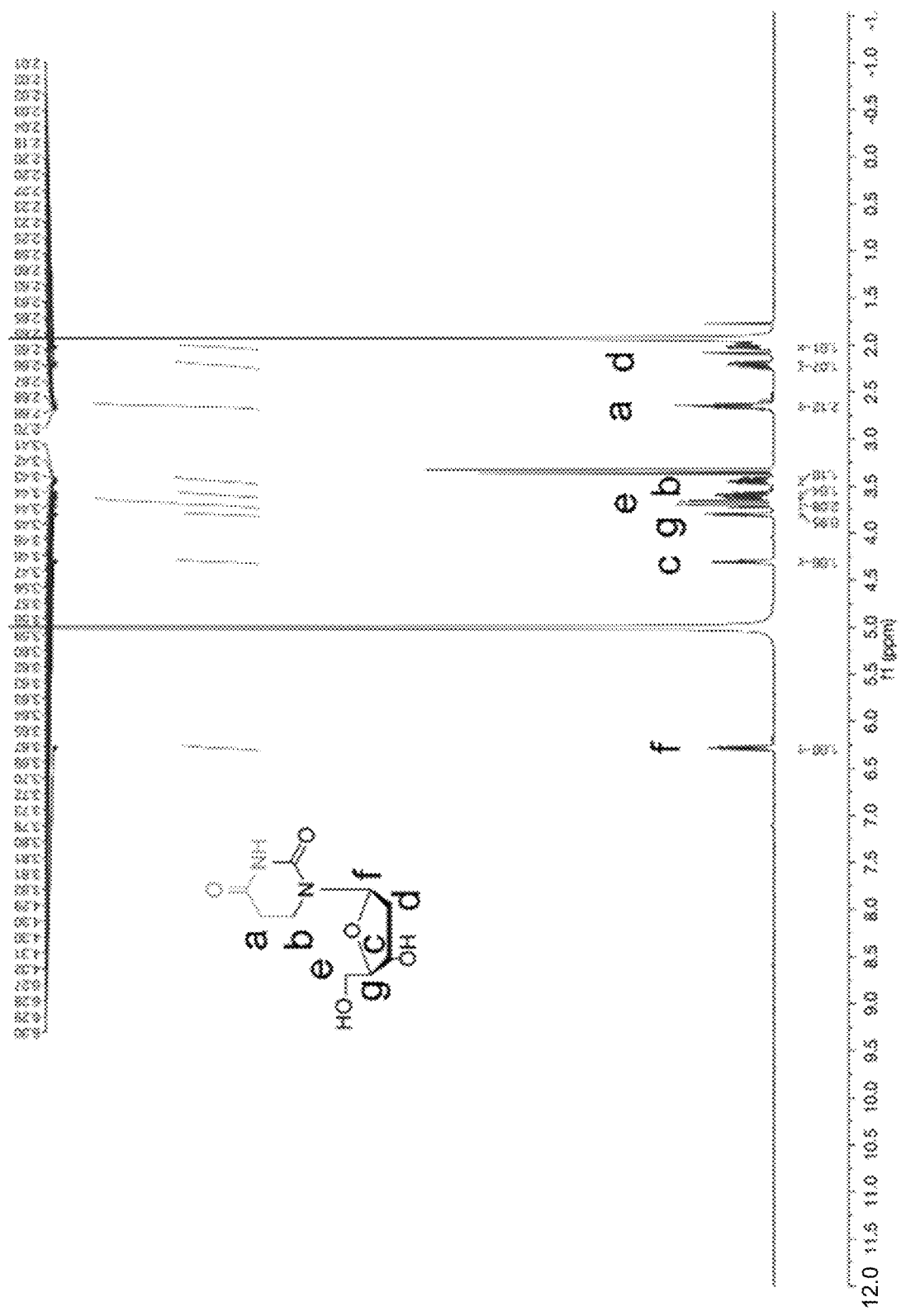
FIG. 3A-B. Single nucleoside pic-borane reaction. $^1$H and $^{13}$C NMR results were in accordance with previous report on 2'-deoxy-5,6-dihydrouridine (I. Aparici-Espert et al., *J. Org. Chem.* 81, 4031-4038 (2016)). (A) $^1$H NMR (MeOH-d$_4$, 400 MHz) chart of the single nucleoside pic-borane reaction product. δ ppm: 6.28 (t, 1H, J=7 Hz), 4.30 (m, 1H), 3.81 (m, 1H), 3.63 (m, 2H), 3.46 (m, 2H), 2.65 (t, 2H, J=6 Hz), 2.20 (m, 1H), 2.03 (m, 1H). (B) $^{13}$C NMR (MeOH-d$_4$, 400 MHz) chart of the single nucleoside pic-borane reaction product. δ ppm: 171.56 (CO), 153.54 (CO), 85.97 (CH), 83.86 (CH), 70.99 (CH), 61.92 (CH$_2$), 36.04 (CH$_2$), 35.46 (CH$_2$), 30.49 (CH$_2$).
Figure 3B:
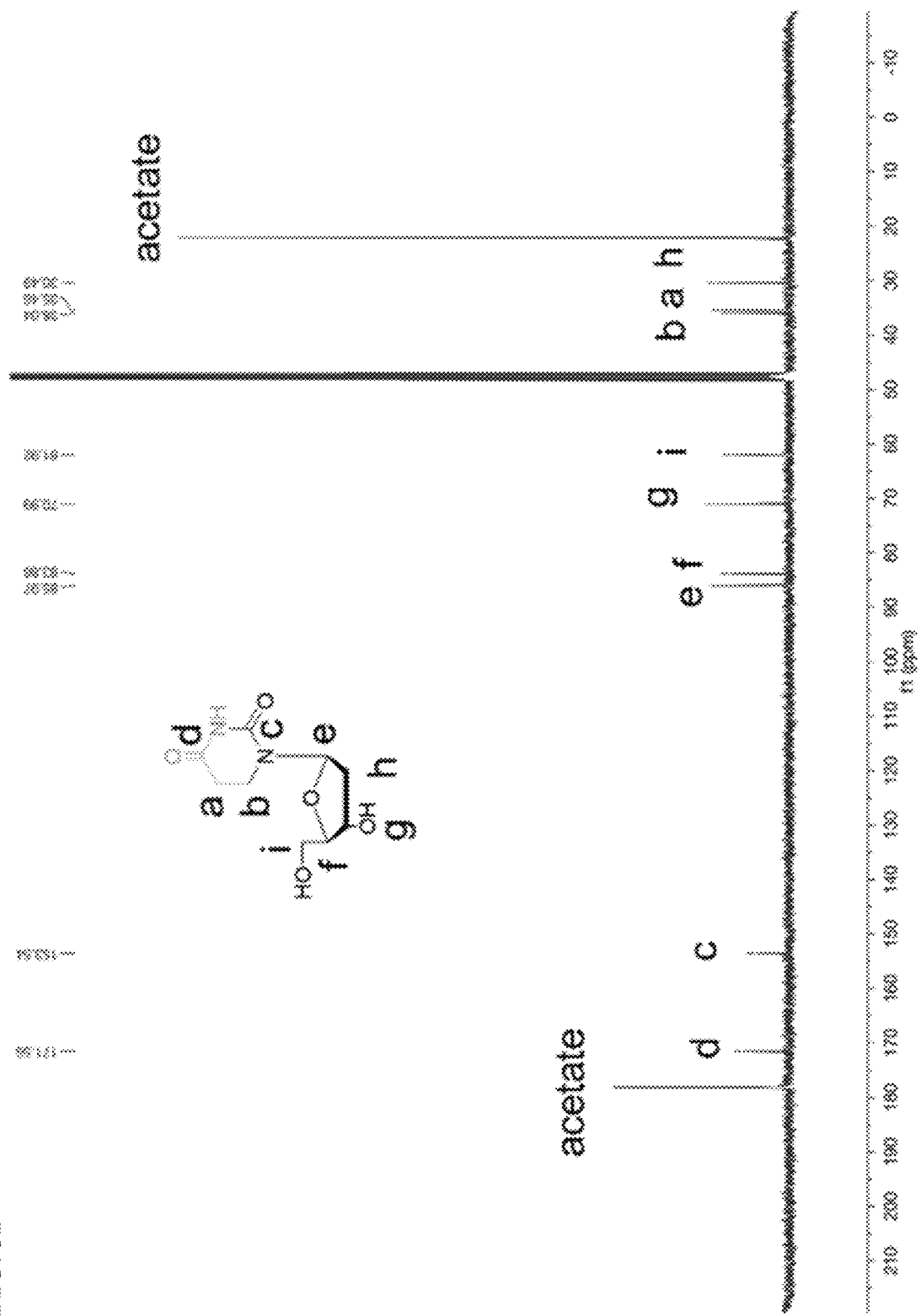
Figure 4A:
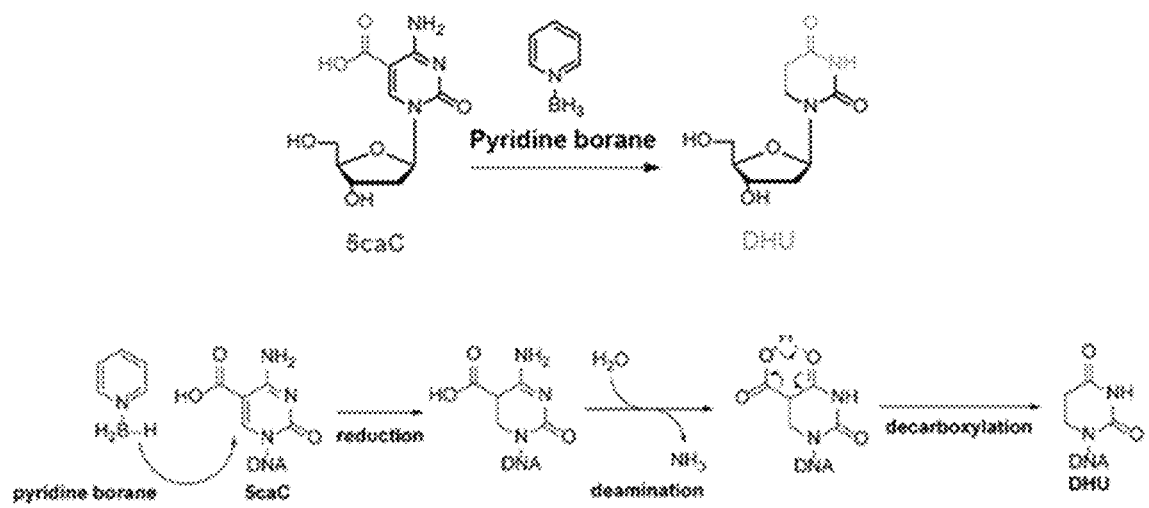
FIG. 4A-B. A diagram showing (A) borane conversion of 5caC to DHU and a proposed mechanism for borane reaction of 5caC to DHU; and (B) borane conversion of 5fC to DHU and a proposed mechanism for borane reaction of 5fC to DHU.

It was discovered that pic-BH$_3$ can readily convert 5fC and 5caC to DHU by a previously unknown reductive decarboxylation/deamination reaction (FIG. 4). The reaction was shown to be quantitative both in single nucleoside and in oligonucleotides using MALDI (FIGS. 2-3, and 6-7).

An 11 mer 5caC-containing DNA oligo was used as a model to screen chemicals that could react with 5caC, as monitored by matrix-assisted laser desorption/ionization mass spectroscopy (MALDI). Certain borane-containing compounds were found to efficiently react with the 5caC oligo, resulting in a molecular weight reduction of 41 Da (FIGS. 1 and 2). Pyridine borane and its derivative 2-picoline borane (pic-borane) were selected for further study as they are commercially available and environmentally benign reducing agents.

Figure 4B:
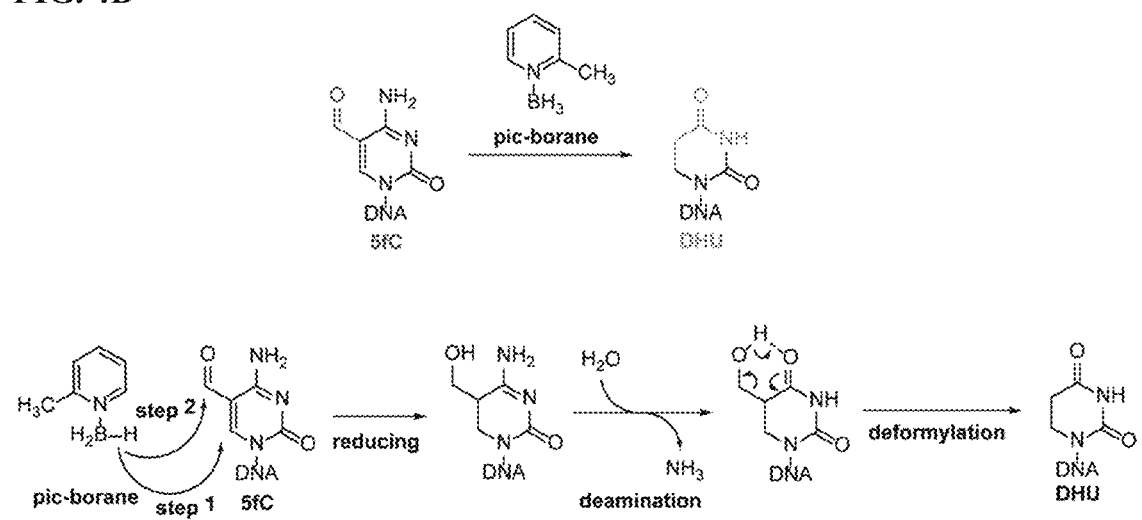
Figure 6:
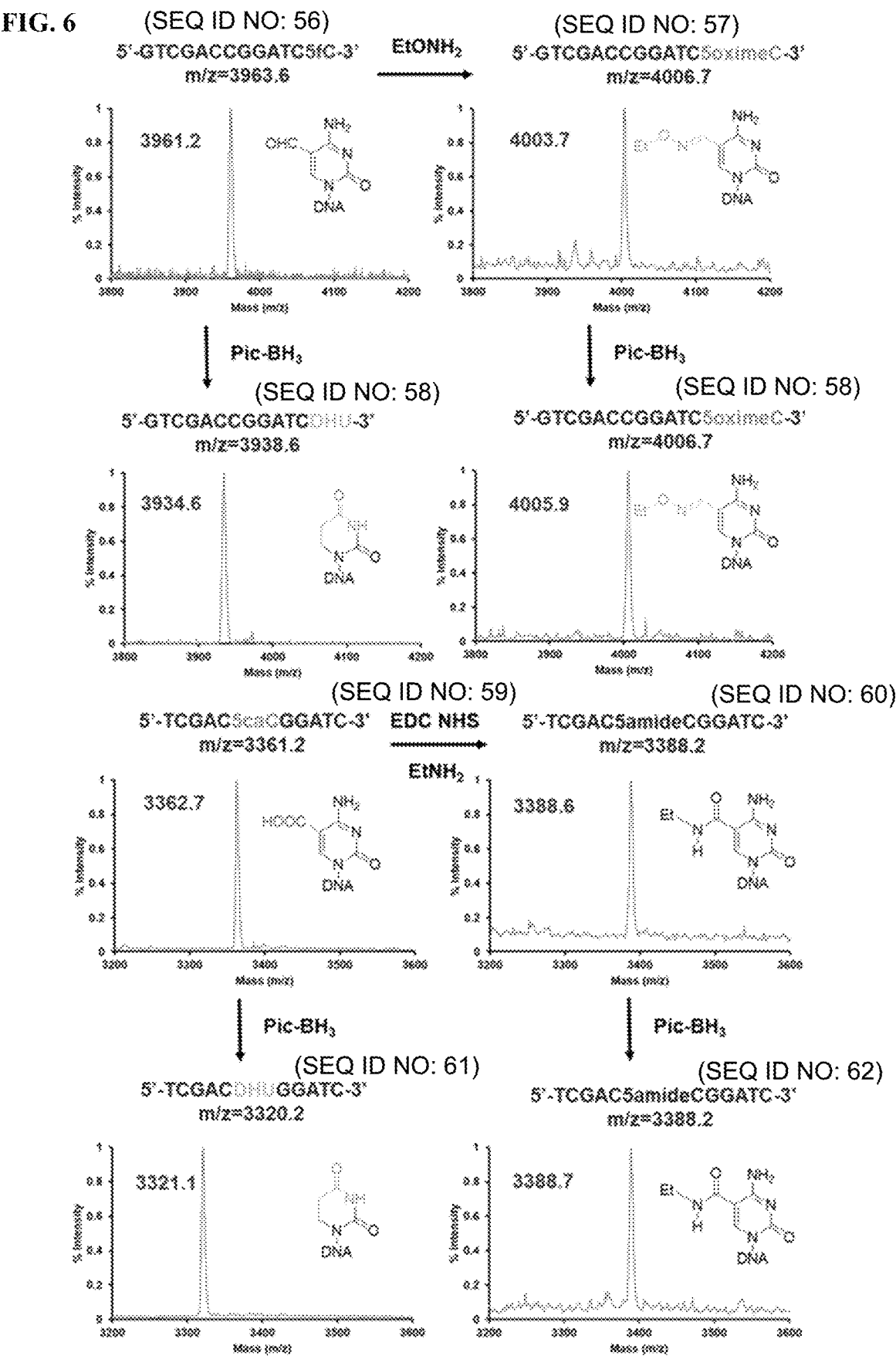
FIG. 6. MALDI characterization of 5fC and 5caC containing model DNA oligos treated by pic-borane with or without blocking 5fC and 5caC. 5fC and 5caC are converted to dihydrouracil (DHU) with pic-BH$_3$. 5fC was blocked by hydroxylamine derivatives such as O-ethylhydroxylamine (EtONH$_2$) which would become oxime and resist pic-borane conversion. 5caC was blocked by ethylamine via EDC conjugation and converted to amide which blocks conversion by pic-borane. Calculated MS (m/z) shown above each graph, observed MS shown to the left of the peak.

The reaction on a single 5caC nucleoside was repeated and confirmed that pyridine borane and pic-borane convert 5caC to dihydrouracil (DHU) (FIGS. 3, 4B). Interestingly, pyridine borane and pic-borane was found to also convert 5fC to DHU through an apparent reductive decarboxylation/deamination mechanism (FIGS. 4C and 6). The detailed mechanism of both reactions remains to be defined. Quantitative analysis of the borane reaction on the DNA oligo by HPLC-MS/MS confirms that pic-borane converts 5caC and 5fC to DHU with around 98% efficiency and has no activity against unmethylated cytosine, 5mC or 5hmC (FIG. 2B).

As a uracil derivative, DHU can be recognized by both DNA and RNA polymerases as thymine. Therefore, borane reduction can be used to induce both 5caC-to-T and 5fC-to-T transitions, and can be used for base-resolution sequencing of 5fC and 5caC, which we termed Pyridine borane Sequencing ("PS") (Table 6). The borane reduction of 5fC and 5caC to T can be blocked through hydroxylamine conjugation (C. X. Song et al., Genome-wide profiling of 5-formylcytosine reveals its roles in epigenetic priming. *Cell* 153, 678-691 (2013), incorporated herein by reference) and EDC coupling (X. Lu et al., Chemical modification-assisted bisulfite sequencing (CAB-Seq) for 5-carboxylcytosine detection in DNA. *J. Am. Chem. Soc.* 135, 9315-9317 (2013), incorporated herein by reference), respectively (FIG. 6). This blocking allows PS to be used to sequence 5fC or 5caC specifically (Table 6).

TABLE 6

Comparison of BS and related methods versus PS for 5fC and 5caC sequencing.

| Base | BS | fCAB-Seq/ redBS-Seq | caCAB-Seq | fC-CET | PS | PS with 5fC blocking | PS with 5caC blocking |
|------|----|----|----|----|----|----|----|
| C    | T  | T  | T  | C  | C  | C  | C  |
| 5mC  | C  | C  | C  | C  | C  | C  | C  |
| 5hmC | C  | C  | C  | C  | C  | C  | C  |
| 5fC  | T  | C  | T  | T  | T  | C  | T  |
| 5caC | T  | T  | C  | C  | T  | T  | C  |

Figure 5A:
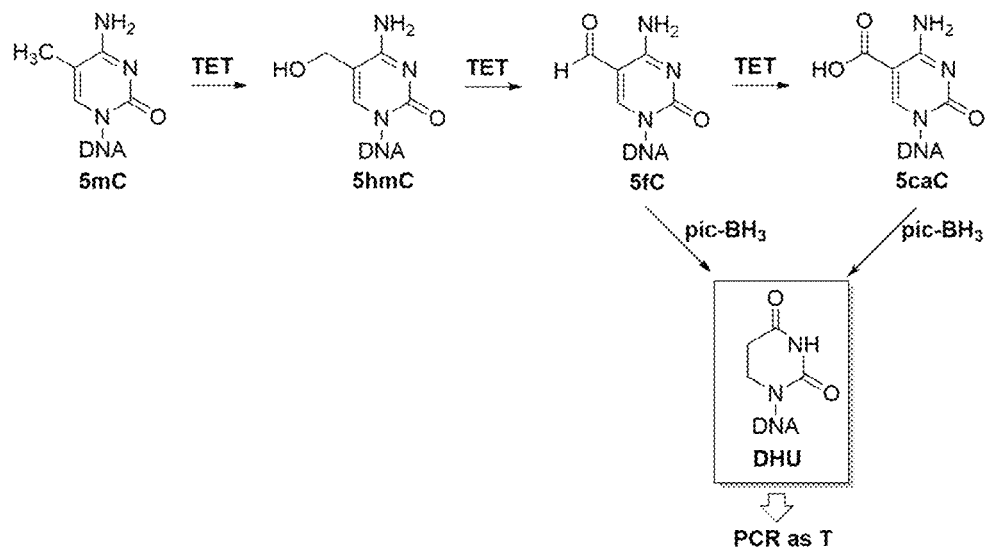
FIG. 5A-B. (A) Diagram showing that the TAPS method converts both 5mC and 5hmC to DHU, which upon replication acts as thymine. (B) Overview of the TAPS, TAPSβ, and CAPS methods.
Figure 5B:
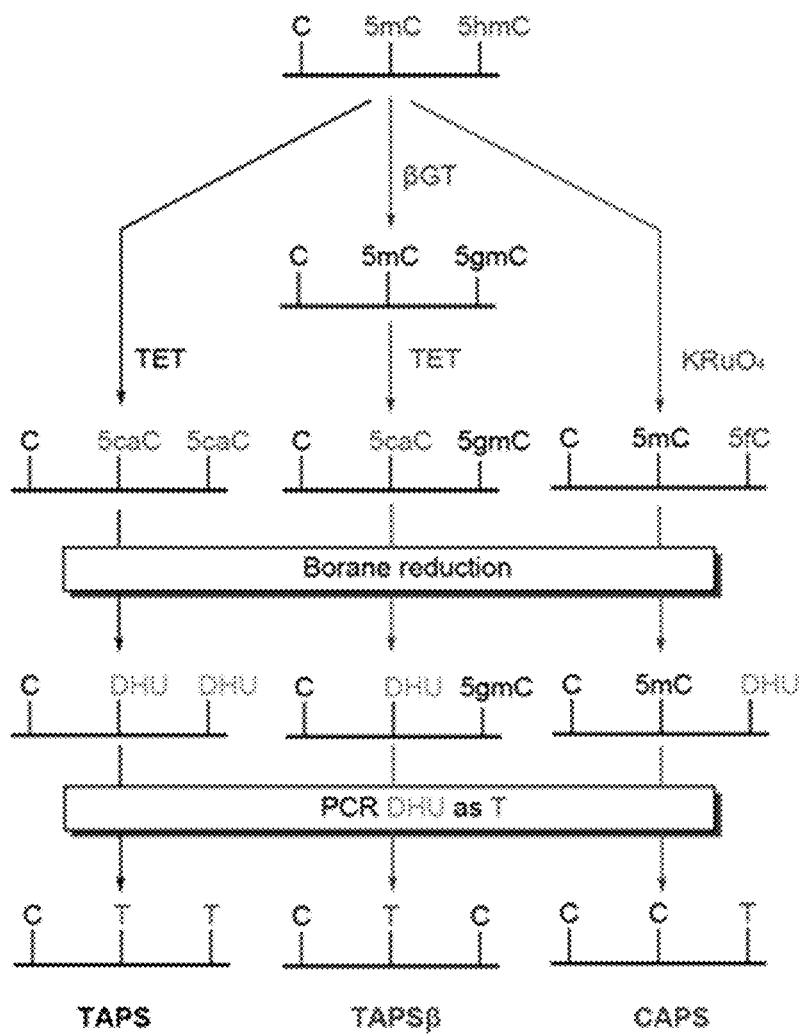

Furthermore, TET enzymes can be used to oxidize 5mC and 5hmC to 5caC, and then subject 5caC to borane reduction in a process herein called TET-Assisted Pyridine borane Sequencing ("TAPS") (FIG. 5A-B, Table 1). TAPS can induce a C-to-T transition of 5mC and 5hmC, and therefore can be used for base-resolution detection of 5mC and 5hmC.

Figure 7:
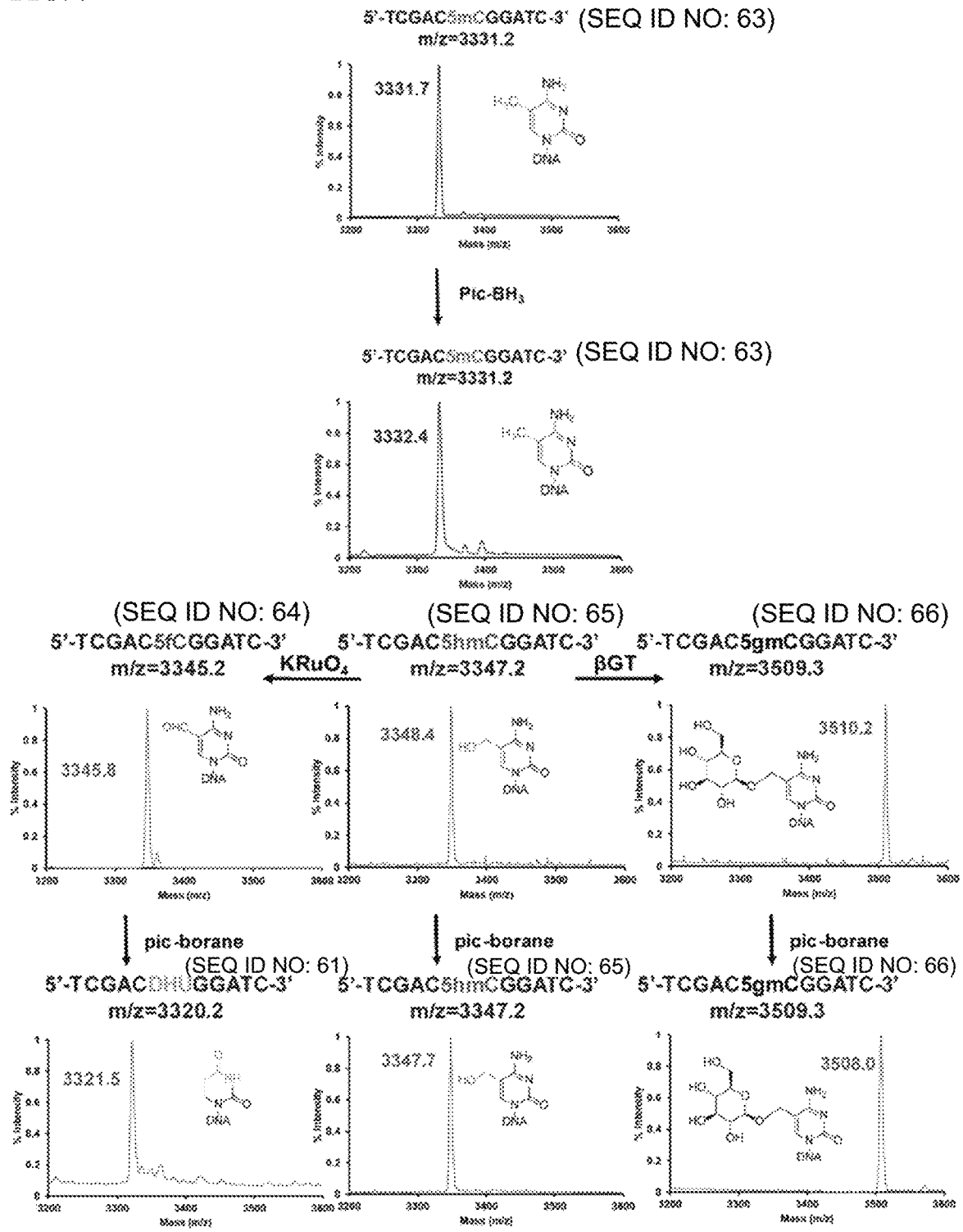
FIG. 7. MALDI characterization of 5mC and 5hmC containing model DNA oligos treated by KRuO$_4$ and pic-borane with or without blocking of 5hmC. 5hmC could be blocked by βGT with glucose and converted to 5gmC. 5mC, 5hmC and 5gmC could not be converted by pic-borane. 5hmC could be oxidized by KRuO$_4$ to 5fC, and then converted to DHU by pic-borane. Calculated MS (m/z) shown above each graph, observed MS shown to the left of the peak.

In addition, β-glucosyltransferase (βGT) can label 5hmC with glucose and thereby protect it from TET oxidation (M. Yu et al., Base-resolution analysis of 5-hydroxymethylcytosine in the mammalian genome. *Cell* 149, 1368-1380 (2012)) and borane reduction (FIG. 7), enabling the selective sequencing of only 5mC, in a process referred to herein as TAPSβ (FIG. 5B, Table 1). 5hmC sites can then be deduced by subtraction of TAPSβ from TAPS measurements. Alternatively, potassium perruthenate (KRuO$_4$), a reagent previously used in oxidative bisulfite sequencing (oxBS) (M. J. Booth et al., Quantitative Sequencing of 5-Methylcytosine and 5-Hydroxymethylcytosine at Single-Base Resolution. *Science* 336, 934-937 (2012)), can be used to replace TET as a chemical oxidant to specifically oxidize 5hmC to 5fC (FIG. 7). This approach, referred to herein as Chemical-Assisted Pyridine borane Sequencing ("CAPS"), can be used to sequence 5hmC specifically (FIG. 5B, Table 1). Therefore, TAPS and related methods can in principle offer a comprehensive suite to sequence all four cytosine epigenetic modifications (FIG. 5B, Table 1, Table 6).

TAPS alone will detect the existing 5fC and 5caC in the genome as well. However, given the extremely low levels of 5fC and 5caC in genomic DNA under normal conditions, this will be acceptable. If under certain conditions, one would like to eliminate the 5fC and 5caC signals completely, it can also be readily accomplished by protecting the 5fC and 5caC by hydroxylamine conjugation and EDC coupling, respectively, thereby preventing conversion to DHU.

Figure 8A:
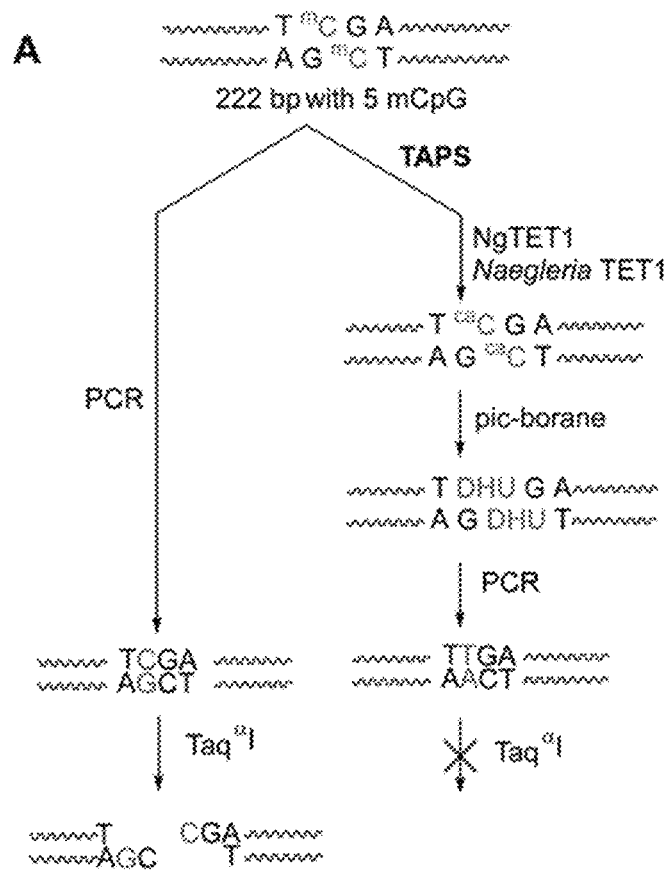
FIG. 8A-B. Restriction enzyme digestion showed TAPS could effectively convert 5mC to T. (A) Illustration of restriction enzyme digestion assay to confirm sequence change caused by TAPS. (B) TaqαI-digestion tests to confirm the C-to-T transition caused by TAPS. TAPS was performed on a 222 bp model DNA having a TaqαI restriction site and containing 5 fully methylated CpG sites (5mC) and its unmethylated control (C). PCR-amplified 222 bp model DNA can be cleaved with TaqαI to ~160 bp and ~60 bp fragments as shown in the 5mC, C and C TAPS. After TAPS on the methylated DNA, the T(mC)GA sequence is converted to TTGA and is no longer cleaved by TaqαI digestion as shown in the 5mC-TAPS lanes.
Figure 8B:
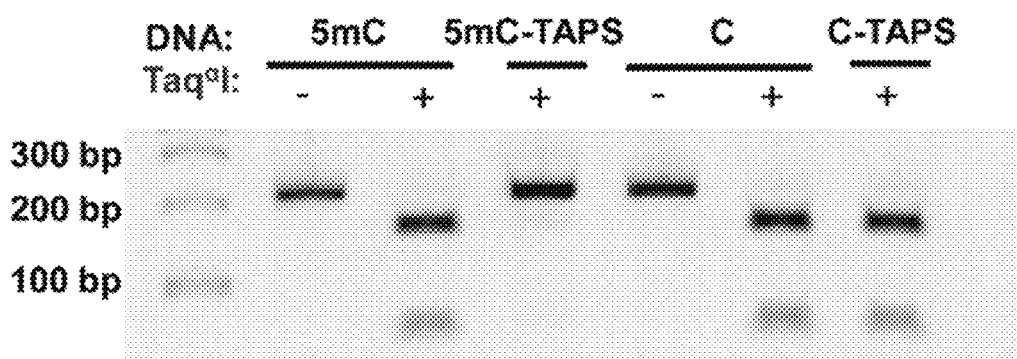
Figure 9A:
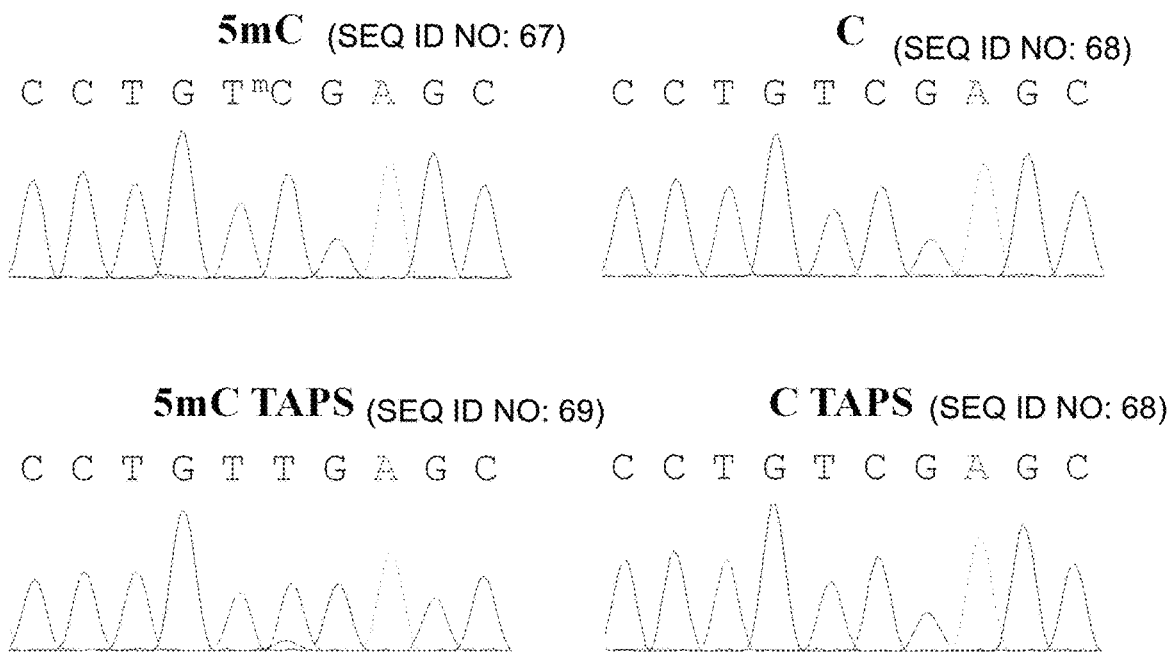
FIG. 9A-B. TAPS on a 222 bp model DNA and mESC gDNA. (A) Sanger sequencing results for the 222 bp model DNA containing 5 fully methylated CpG sites and its unmethylated control before (5mC, C) and after TAPS (5mC TAPS, C TAPS). Only 5mC is converted to T by the TAPS method. (B) HPLC-MS/MS quantification of relative modification levels in the mESCs gDNA control, after NgTET1 oxidation and after pic-borane reduction. Data shown as mean±SD of three replicates.
Figure 12:
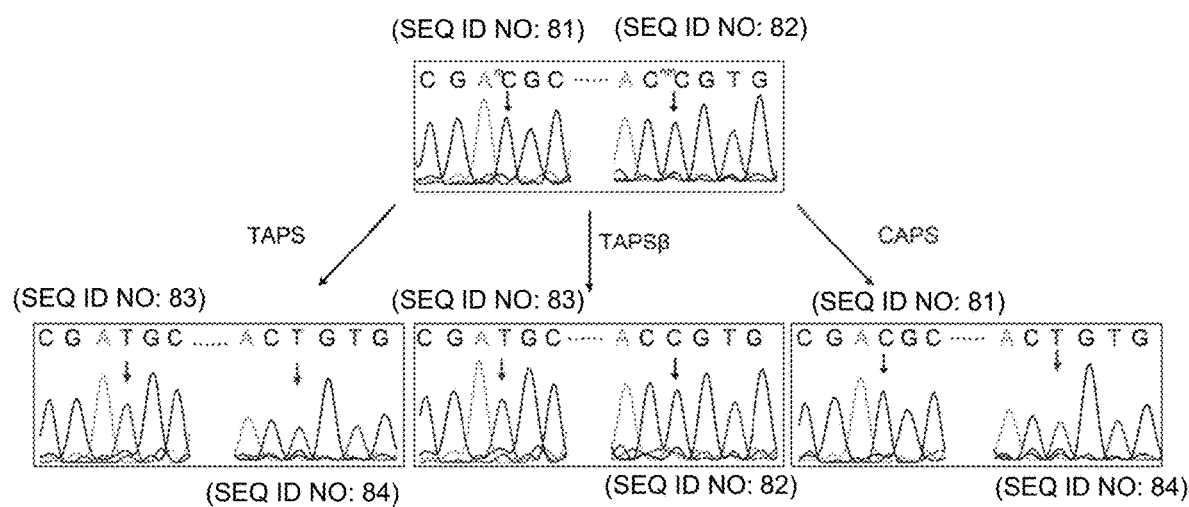
FIG. 12. Complete C-to-T transition induced after TAPS, TAPSβ and CAPS as demonstrated by Sanger sequencing. Model DNA containing single methylated and single hydroxymethylated CpG sites was prepared as described herein. TAPS conversion was done following NgTET1 oxidation and pyridine borane reduction protocol as described herein. TAPSβ conversion was done following 5hmC blocking, NgTET1 Oxidation and Pyridine borane reduction protocol. CAPS conversion was done following 5hmC oxidation and Pyridine borane reduction protocol. After conversion, 1 ng of converted DNA sample was PCR amplified by Taq DNA Polymerase and processed for Sanger sequencing. TAPS converted both 5mC and 5hmC to T. TAPSβ selectively converted 5mC whereas CAPS selectively converted 5hmC. None of the three methods caused conversion on unmodified cytosine and other bases.

The performance of TAPS was evaluated in comparison with bisulfite sequencing, the current standard and most widely used method for base-resolution mapping of 5mC and 5hmC. *Naegleria* TET-like oxygenase (NgTET1) and mouse Tet1 (mTet1) were used because both can efficiently oxidize 5mC to 5caC in vitro. To confirm the 5mC-to-T transition, TAPS was applied to model DNA containing fully methylated CpG sites and showed that it can effectively convert 5mC to T, as demonstrated by restriction enzyme digestion (FIGS. 8A-B) and Sanger sequencing (FIG. 9A). TAPSβ and CAPS were also validated by Sanger sequencing (FIG. 12).

Figure 9B:
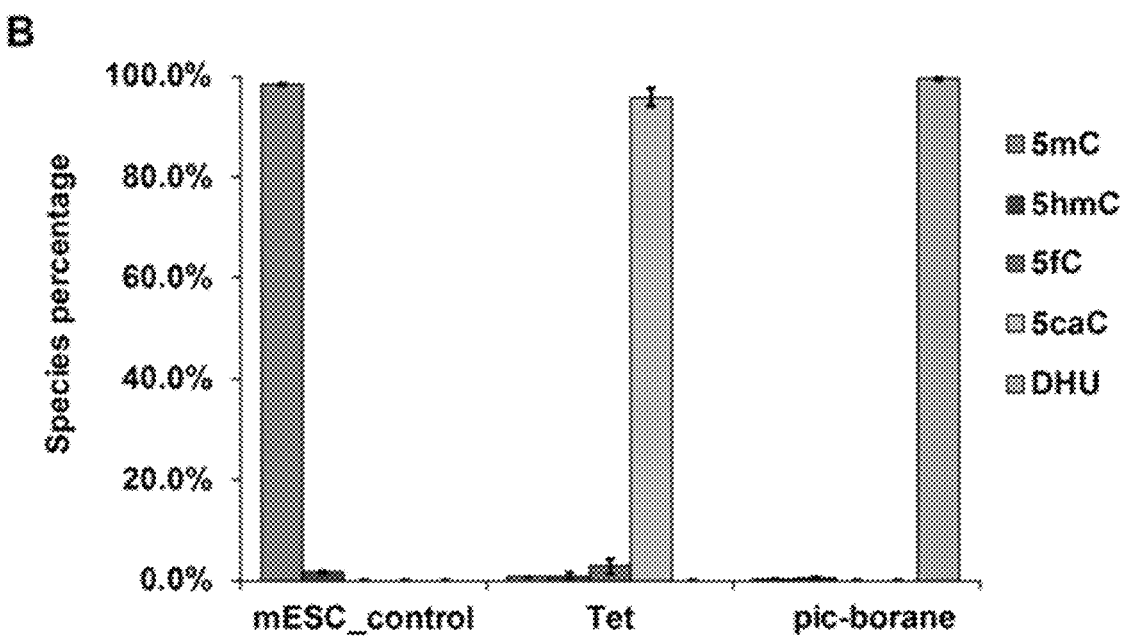

TAPS was also applied to genomic DNA (gDNA) from mouse embryonic stem cells (mESCs). HPLC-MS/MS quantification showed that, as expected, 5mC accounts for 98.5% of cytosine modifications in the mESCs gDNA; the remainder is composed of 5hmC (1.5%) and trace amounts 5fC and 5caC, and no DHU (FIG. 9B). After TET oxidation, about 96% of cytosine modifications were oxidized to 5caC and 3% were oxidized to 5fC (FIG. 9B). After borane reduction, over 99% of the cytosine modifications were converted into DHU (FIG. 9B). These results demonstrate both TET oxidation and borane reduction work efficiently on genomic DNA.

Figure 10A:
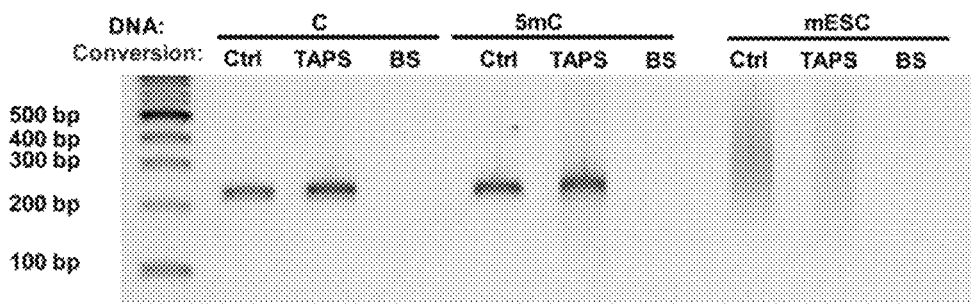
FIG. 10A-D. TAPS caused no significant DNA degradation compared to bisulfite. Agarose gel images of 222 bp unmethylated DNA, 222 bp methylated DNA, and mESC gDNA (A) before and (B) after chilling in an ice bath. No detectable DNA degradation was observed after TAPS and DNA remained double-stranded and could be visualized without chilling. Bisulfite conversion created degradation and DNA became single-stranded and could be visualized only after chilled on ice. (C) Agarose gel images of mESC gDNA of various fragment lengths treated with TAPS and bisulfite before (left panel) and after (right panel) cooling down on ice. DNA after TAPS remained double-stranded and could be directly visualized on the gel. Bisulfite treatment caused more damage and fragmentation to the samples and DNA became single-stranded and could be visualized only after chilled on ice. TAPS conversion was complete for all gDNA regardless of fragment length as shown in FIG. 15. (D) Agarose gel imaging of a 222 bp model DNA before and after TAPS (three independent repeats) showed no detectable degradation after the reaction.
Figure 10B:
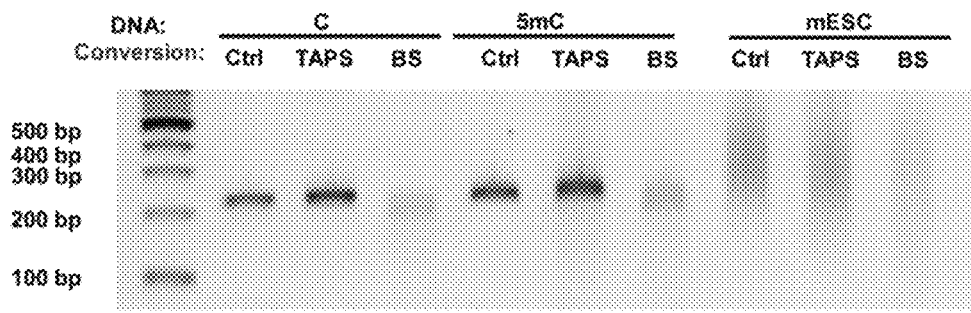
Figure 10C:
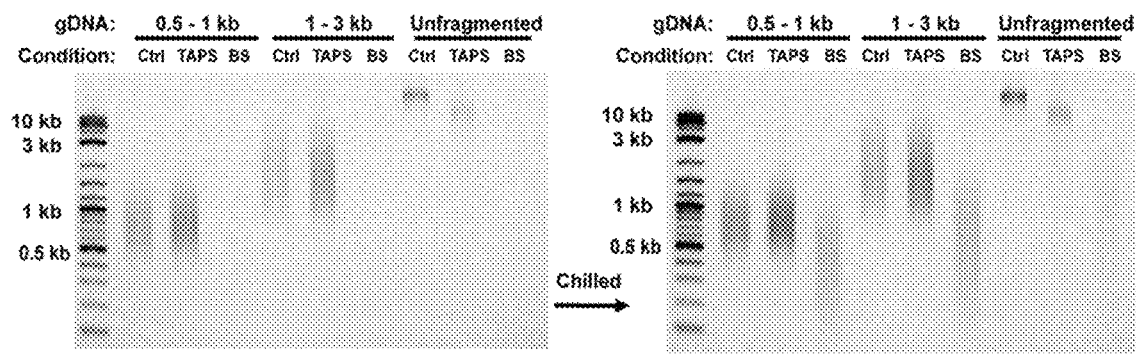
Figure 10D:
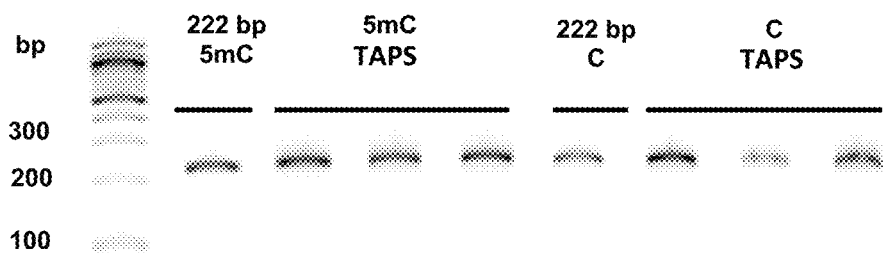
Figure 15A:
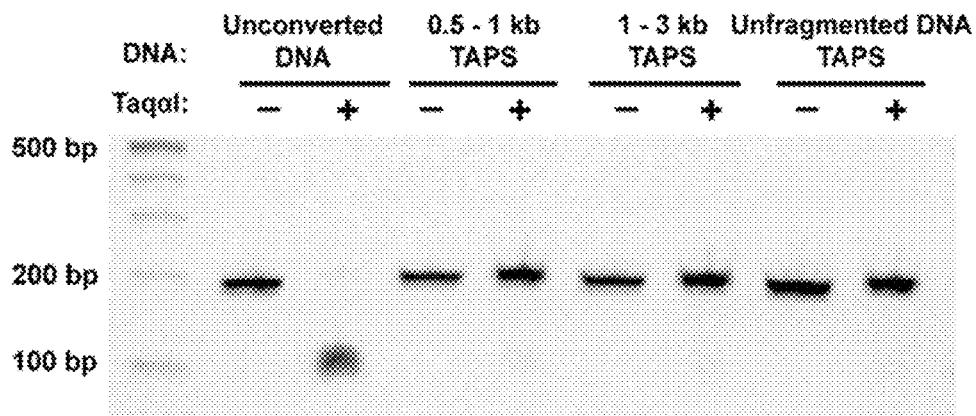
FIG. 15A-B. TAPS completely converted 5mC to T regardless of DNA fragment length. (A) Agarose gel images of TaqαI-digestion assay confirmed complete 5mC to T conversion in all samples regardless of DNA fragment lengths. 194 bp model sequence from lambda genome was PCR amplified after TAPS and digested with TaqαI enzyme. PCR product amplified from unconverted sample could be cleaved, whereas products amplified on TAPS treated samples stayed intact, suggesting loss of restriction site and hence complete 5mC-to-T transition. (B) The C-to-T conversion percentage was estimated by gel band quantification and shown 100% for all DNA fragment lengths tested.
Figure 15B:
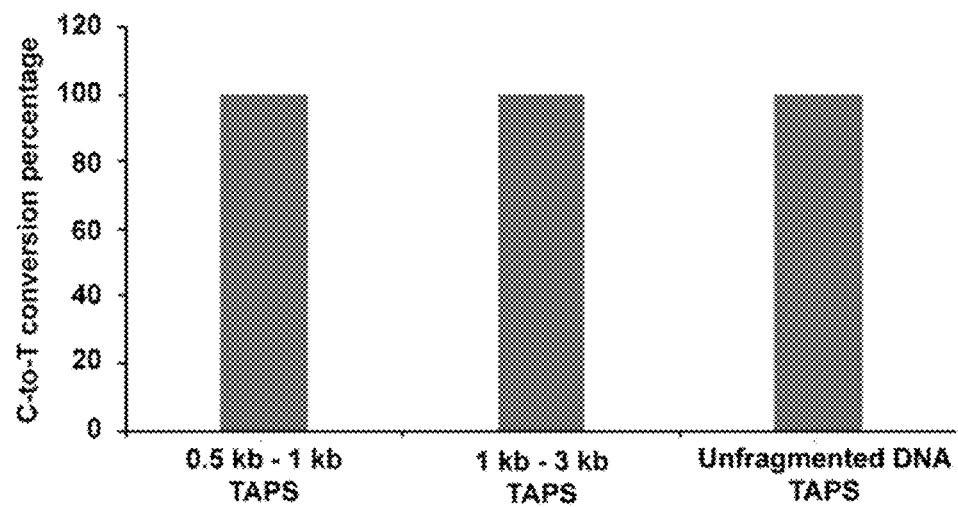

Both TET oxidation and borane reduction are mild reactions, with no notable DNA degradation compared to bisulfite (FIGS. 10A-D) and thereby provide high DNA recovery. Another notable advantage over bisulfite sequencing is that TAPS is non-destructive and can preserve DNA up to 10 kbs long (FIG. 10C). Moreover, DNA remains double stranded after TAPS (FIGS. 10A-C), and the conversion is independent of the DNA length (FIG. 15A-B).

Figure 14:
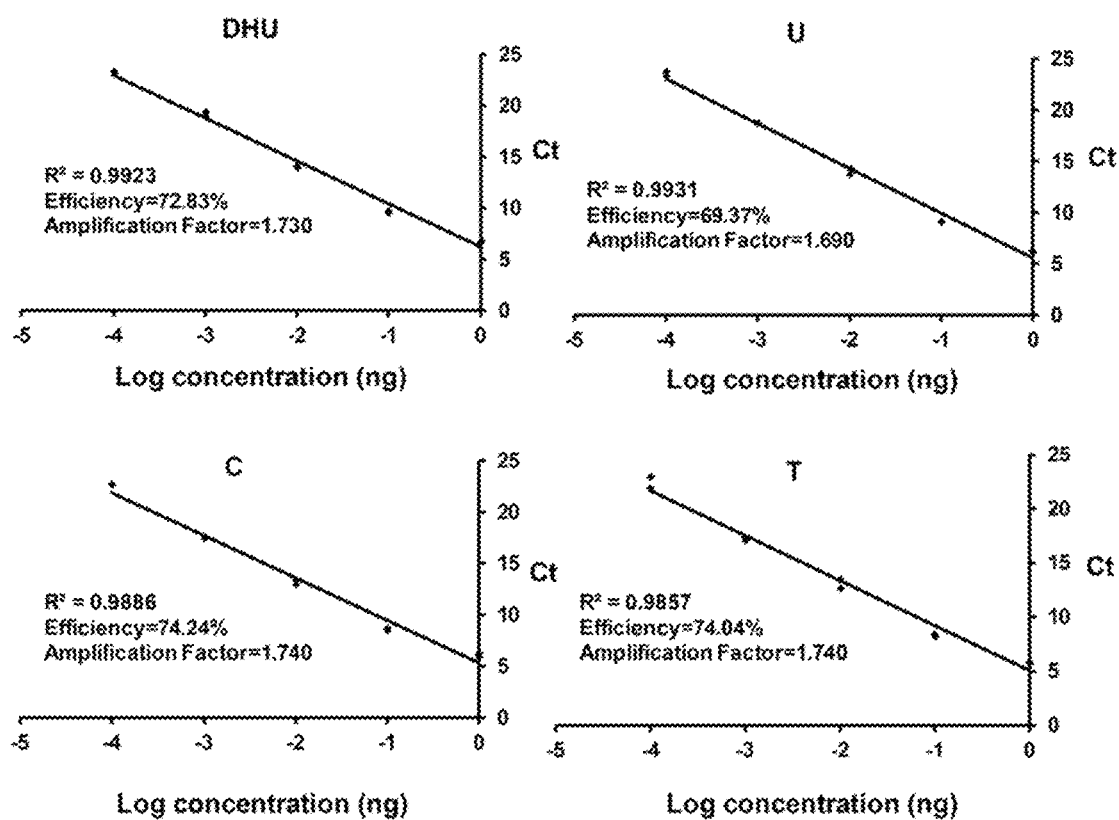
FIG. 14. DHU does not show PCR bias compared to T and C. Model DNA containing one DHU/U/T/C modification was synthesized with the corresponding DNA oligos as described in herein. Standard curves for each model DNA with DHU/U/T/C modification were plotted based on qPCR reactions with 1:10 serial dilutions of the model DNA input (from 0.1 pg to 1 ng, every qPCR experiment was run in triplicates). The slope of the regression between the log concentration (ng) values and the average Ct values was calculated by SLOPE function in Excel. PCR efficiency was calculated using the following equation: Efficiency %= (10^(-1/Slope)-1)*100%. Amplification factor was calculated using the following equation: Amplification factor=10^(-1/Slope). PCR efficiency for model DNAs with DHU or T or C modification were almost the same, which demonstrated that DHU could be read through as a regular base and would not cause PCR bias.

In addition, because DHU is close to a natural base, it is compatible with various DNA polymerases and isothermal DNA or RNA polymerases (FIGS. 13A-B) and does not show a bias compared to T/C during PCR (FIG. 14).

Whole genome sequencing was performed on two samples of mESC gDNA, one converted using TAPS and the other using standard whole-genome bisulfite sequencing (WGBS) for comparison.

Figures 17A, 17B:
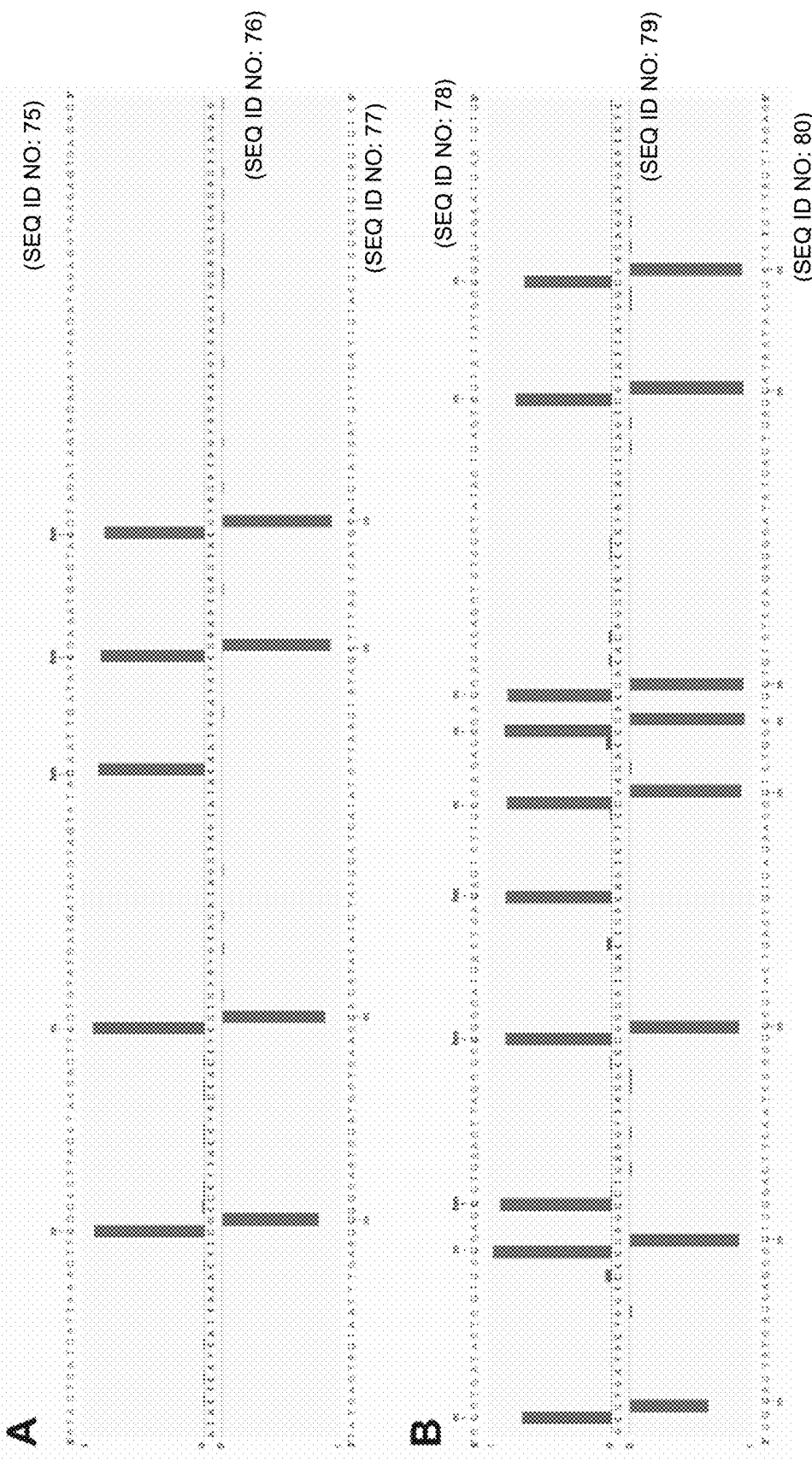
FIG. 17A-B. Conversion rate on short spike-ins. (A) 120 mer-1 and (B) 120 mer-2 containing 5mC and 5hmC. Near complete conversion was archived on 5mC and 5hmC sites from both strands. Actual sequences with modification status shown on top and bottom.

To assess the accuracy of TAPS, spike-ins of different lengths were added that were either fully unmodified, in vitro methylated using CpG Methyltransferase (M.SssI) or GpC Methyltransferase (M.CviPI) (using the above methods). For short spike-ins (120 mer-1 and 120 mer-2) containing 5mC and 5hmC, near complete conversion was observed for both modifications on both strands in both CpG and non-CpG contexts (FIG. 17A-B).

Figure 16:
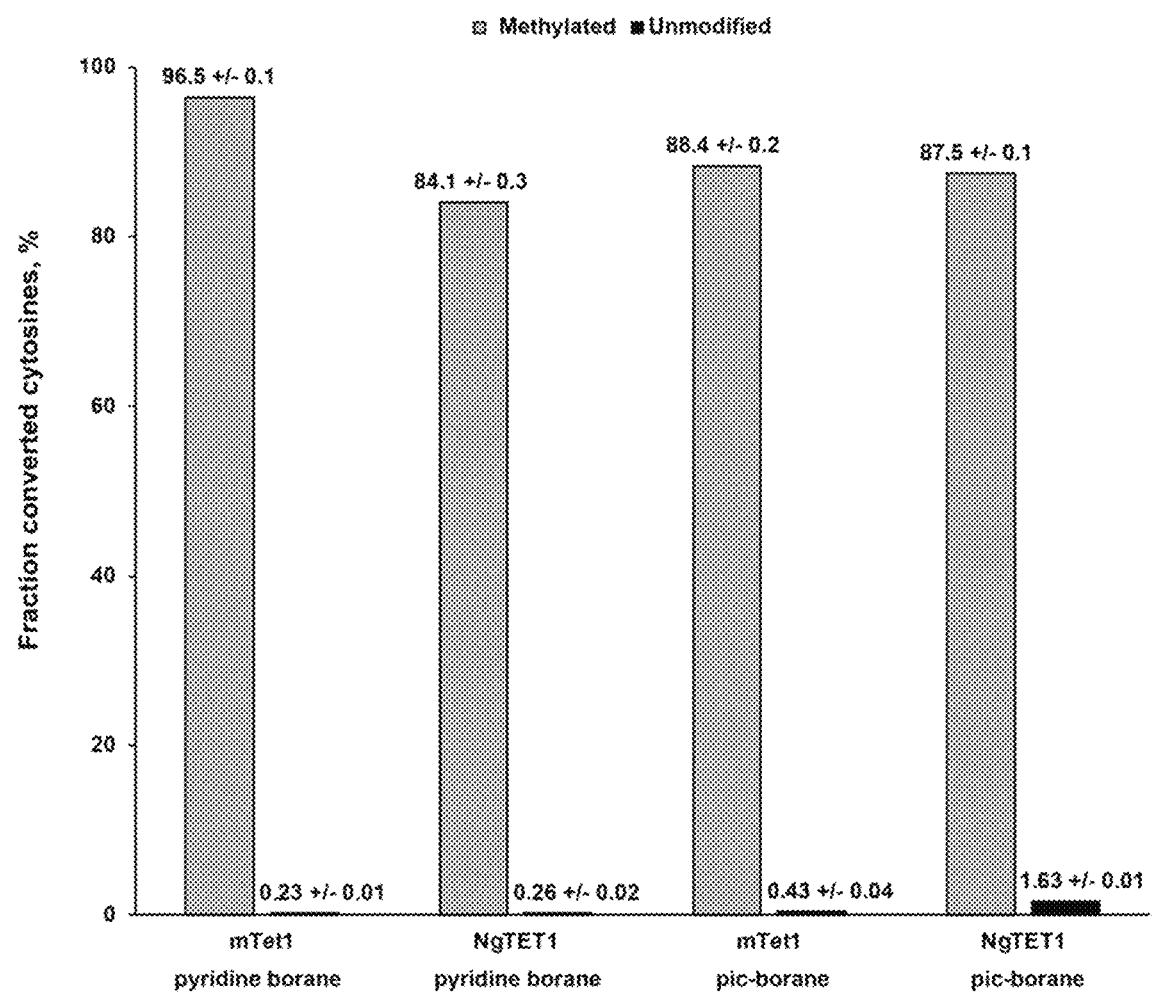
FIG. 16. The conversion and false positive for different TAPS conditions. The combination of mTet1 and pyridine borane achieved the highest conversion rate of methylated C (96.5%, calculated with fully CpG methylated Lambda DNA) and the lowest conversion rate of unmodified C (0.23%, calculated with 2 kb unmodified spike-in), compared to other conditions with NgTET1 or pic-borane. Showing above bars the conversion rate+/-SE of all tested cytosine sites.
Figure 18A:
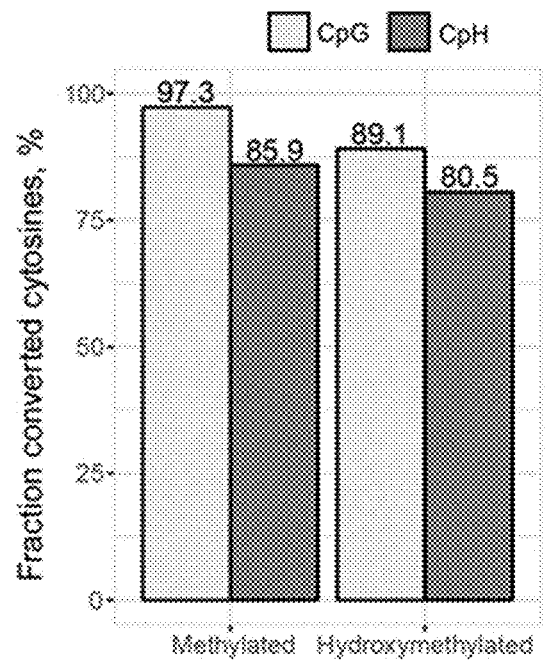
FIG. 18A-E. Improved sequencing quality of TAPS over Whole Genome Bisulfite Sequencing (WGBS). (A) Conversion rate of 5mC and 5hmC in TAPS-treated DNA. Left: Synthetic spike-ins (CpN) methylated or hydroxymethylated at known positions. (B) False positive rate of TAPS from unmodified 2 kb spike-in. (C) Total run time of TAPS and WGBS when processing 1 million simulated reads on one core of one Intel Xeon CPU. (D) Fraction of all sequenced read pairs (after trimming) mapped to the genome. (E) Sequencing quality scores per base for the first and second reads in all sequenced read pairs, as reported by Illumina BaseSpace. Top: TAPS. Bottom: WGBS.
Figure 18B:
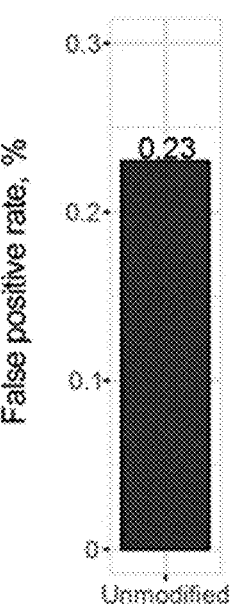

100 ng gDNA was used for TAPS, compared to 200 ng gDNA for WGBS. To assess the accuracy of TAPS, we added three different types of spike-in controls. Lambda DNA where all CpGs were fully methylated was used to estimate the false negative rate (non-conversion rate of 5mC); a 2 kb unmodified amplicon was used to estimate the false positive rate (conversion rate of unmodified C); synthetic oligo spike-ins containing both a methylated and hydroxymethylated C surrounded by any other base (N5mCNN and N5hmCNN, respectively) were used to compare the conversion rate on 5mC and 5hmC in different sequence contexts. The combination of mTet1 and pyridine borane achieved the highest 5mC conversion rate (96.5% and 97.3% in lambda and synthetic spike-ins, respectively) and the lowest conversion rate of unmodified C (0.23%) (FIGS. 18A-B and FIG. 16). A false negative rate between 2.7% and 3.5%, with a false-positive rate of only 0.23%, is comparable to bisulfite sequencing: a recent study showed 9 commercial bisulfite kits had average false negative and false positive rates of 1.7% and 0.6%, respectively (Holmes, E. E. et al. Performance evaluation of kits for bisulfite-conversion of DNA from tissues, cell lines, FFPE tissues, aspirates, lavages, effusions, plasma, serum, and urine. PLoS One 9, e93933 (2014)). The synthetic spike-ins suggest that TAPS works well on both 5mC and 5hmC, and that TAPS performs only slightly worse in non-CpG contexts. The conversion for 5hmC is 8.2% lower than 5mC, and the conversion for non-CpG contexts is 11.4% lower than for CpG contexts (FIG. 18A).

Figure 18C:
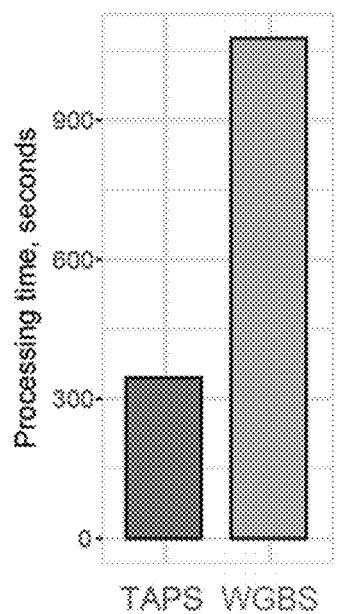

WGBS data requires special software both for the alignment and modification-calling steps. In contrast, our processing pipeline uses a standard genomic aligner (bwa), followed by a custom modification-calling tool that we call "asTair". When processing simulated WGBS and TAPS reads (derived from the same semi-methylated source sequence), TAPS/asTair was more than 3× faster than WGBS/Bismark (FIG. 18C).

Figure 18D:
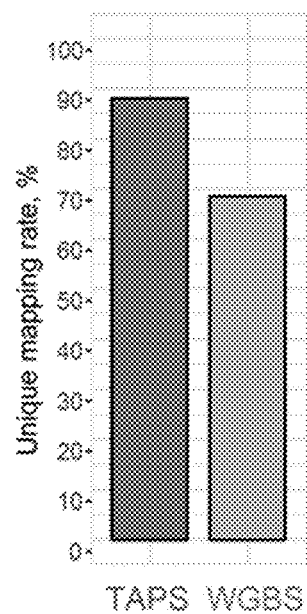
Figure 18E:
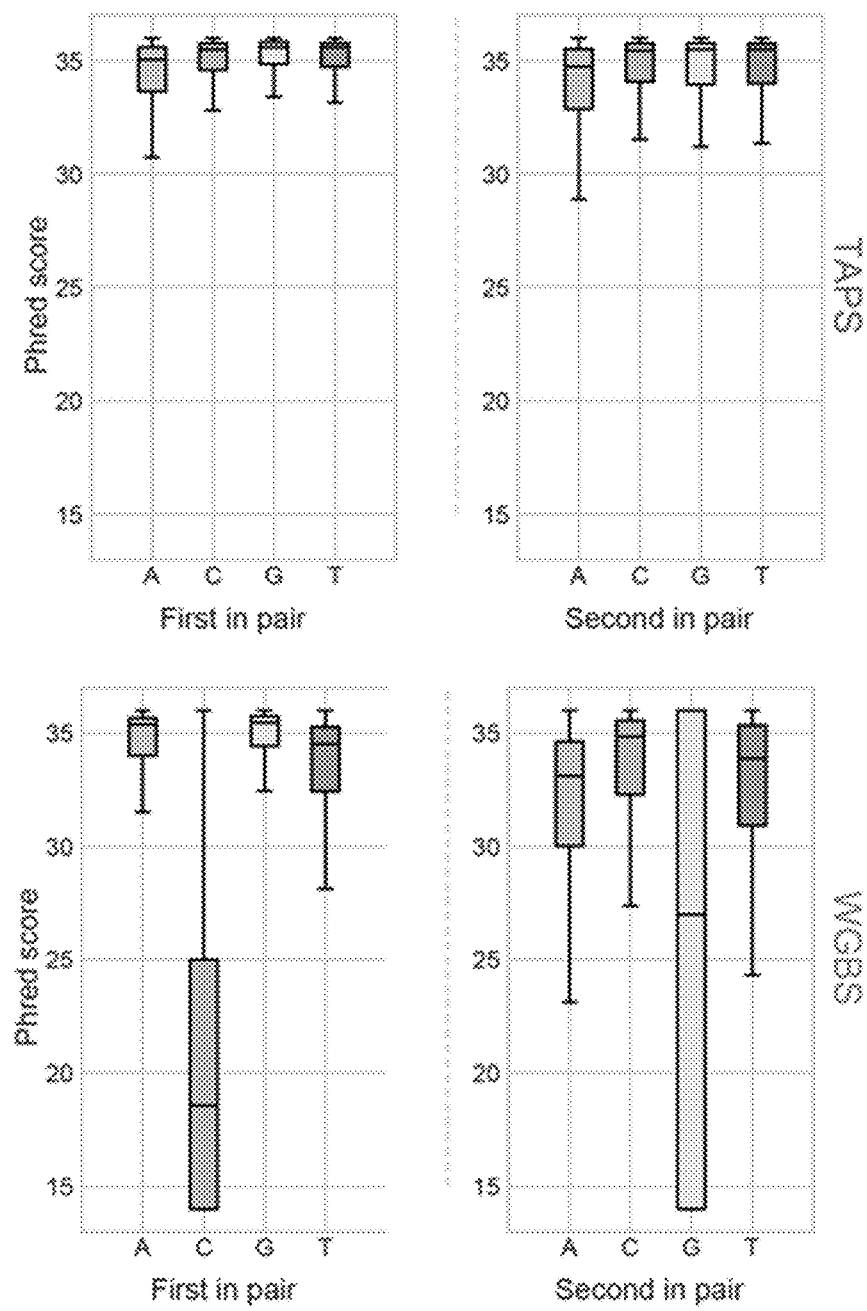

Due to the conversion of nearly all cytosine to thymine, WGBS libraries feature an extremely skewed nucleotide composition which can negatively affect Illumina sequencing. Consequently, WGBS reads showed substantially lower sequencing quality scores at cytosine/guanine base pairs compared to TAPS (FIG. 18E). To compensate for the nucleotide composition bias, at least 10 to 20% PhiX DNA (a base-balanced control library) is commonly added to WGBS libraries (see, e.g., Illumina's Whole-Genome Bisulfite Sequencing on the HiSeq 3000/HiSeq 4000 Systems). Accordingly, we supplemented the WGBS library with 15% PhiX. This, in combination with the reduced information content of BS-converted reads, and DNA degradation as a result of bisulfite treatment, resulted in significantly lower mapping rates for WGBS compared to TAPS (FIG. 18D and Table 7).

TABLE 7

Mapping and sequencing quality statistics for WGBS and TAPS.

| Measure | WGBS | TAPS |
|---|---|---|
| Total raw reads | 376062375 | 455548210 |
| Trimmed reads | 367860813 | 453028186 |
| Mapped reads (mm9 + spike-ins + PhiX) | 251940139 | 451077132 |
| PCR deduplicated reads | 232303596 | 398127851 |
| Mapping rate (mapped reads/trimmed reads) | 68.49% | 99.57% |
| Unique mapping rate (unique reads [MAPQ > 0 for TAPS]/trimmed reads) | 68.49% | 88.08% |
| Unique PCR deduplicated mapping rate (unique PCR deduplicated reads [MAPQ > 0 for TAPS]/trimmed reads) | 63.15% | 81.31% |

Therefore, for the same sequencing cost (one NextSeq High Output run), the average depth of TAPS exceeded that of WGBS (21× and 13.1×, respectively; Table 8). Furthermore, TAPS resulted in fewer uncovered regions, and overall showed a more even coverage distribution, even after down-sampling to the same sequencing depth as WGBS (inter-quartile range: 9 and 11, respectively; FIG. 19A and Table 8).

TABLE 8

Coverage statistics for TAPS, WGBS and TAPS down-sampled to have approximately the same mean coverage as WGBS. Here, coverage was computed for both strands at all positions in the genome.

| Measure | WGBS | TAPS with down-sampling | TAPS without down-sampling |
|---|---|---|---|
| Mean | 13.078 | 12.411 | 21.001 |
| Variance | 1988.242 | 482.242 | 1371.912 |
| median | 13 | 13 | 22 |
| qtl25 | 7 | 8 | 15 |
| qtl75 | 18 | 17 | 28 |
| iqr | 11 | 9 | 13 |
| maximum | 116084 | 37329 | 63526 |

Figure 21A:
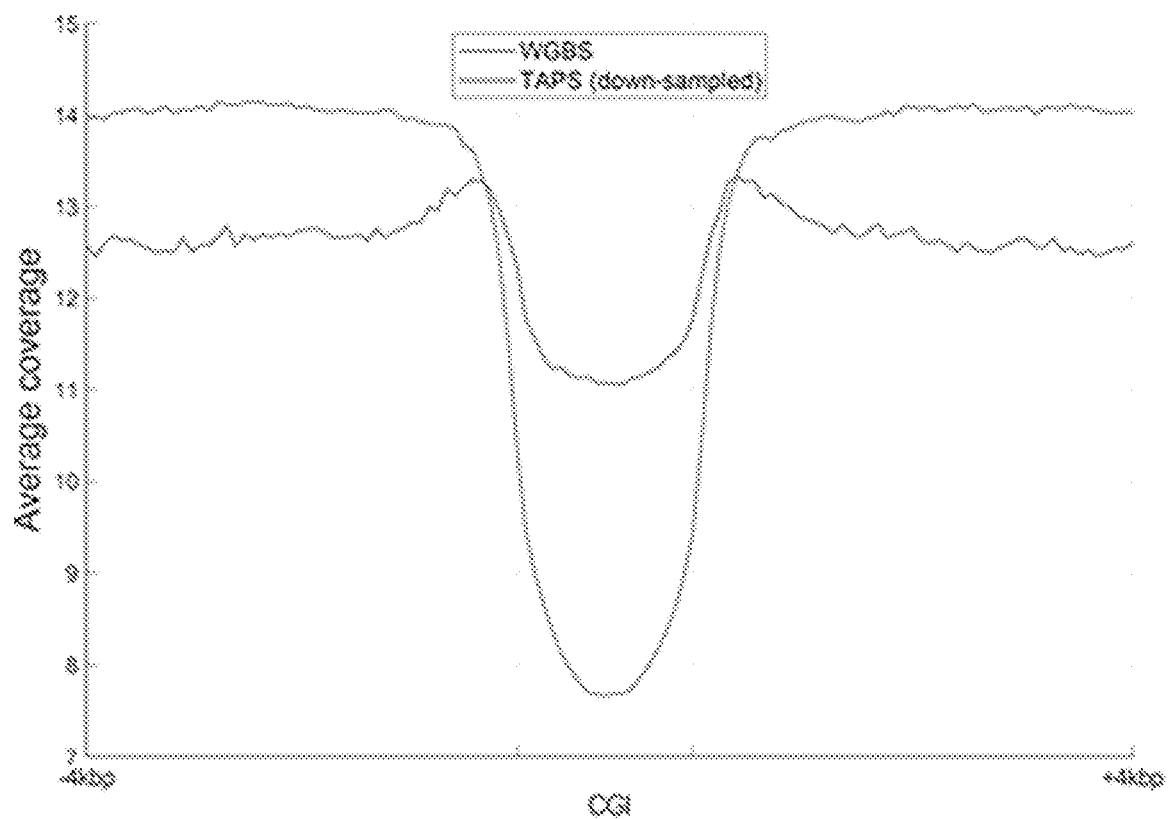
FIG. 21A-E. Comparison of genome-wide methylome measurements by TAPS and WGBS. (A) Average sequencing coverage depth in all mouse CpG islands (binned into 20 windows) and 4 kbp flanking regions (binned into 50 equally sized windows). To account for differences in sequencing depth, all mapped TAPS reads were down-sampled to match the median number of mapped WGBS reads across the genome. (B) CpG sites covered by at least three reads by TAPS alone, both TAPS and WGBS, or WGBS alone. (C) Number of CpG sites covered by at least three reads and modification level>0.1 detected by TAPS alone, TAPS and WGBS, or WGBS alone. (D) Example of the chromosomal distribution of modification levels (in %) for TAPS and WGBS. Average fraction of modified CpGs per 100 kb windows along mouse chromosome 4, smoothed using a Gaussian-weighted moving average filter with window size 10. (E) Heatmap representing the number of CpG sites covered by at least three reads in both TAPS and WGBS, broken down by modification levels as measured by each method. To improve contrast, the first bin, containing CpGs unmodified in both methods, was excluded from the color scale and is denoted by a star.
Figure 22:
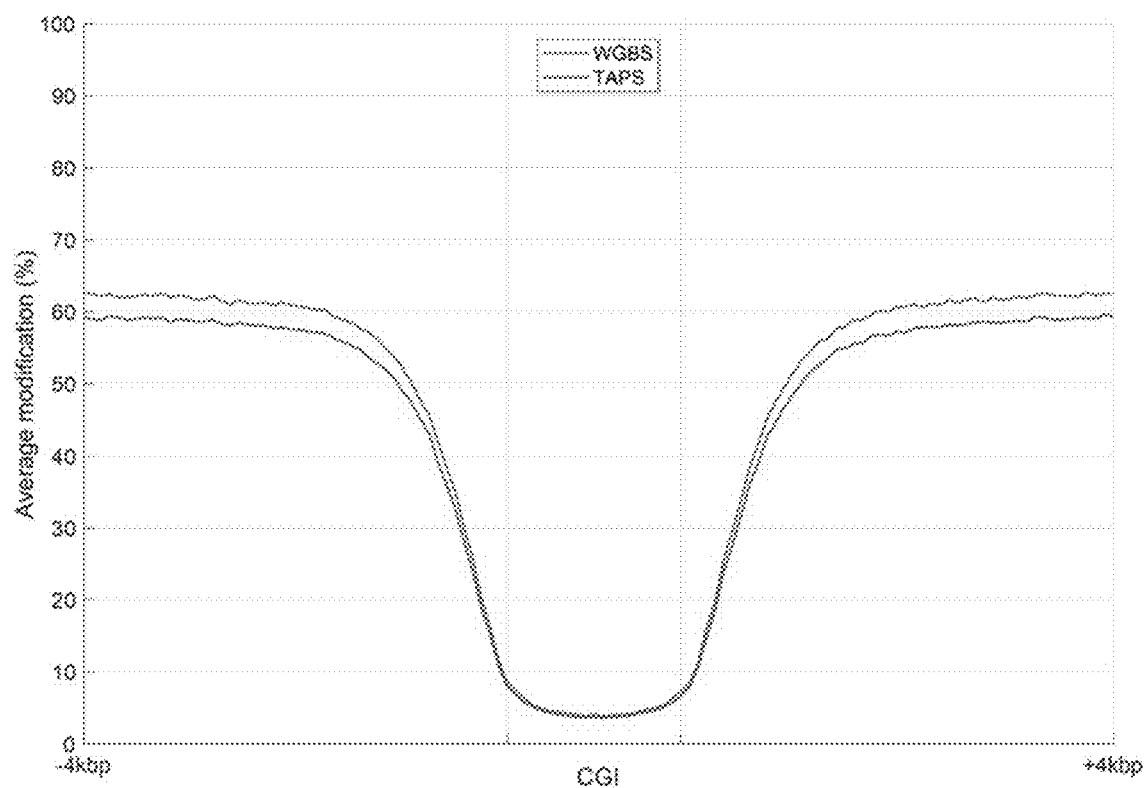
FIG. 22. Modification levels around CpG Islands. Average modification levels in CpG islands (binned into 20 windows) and 4 kbp flanking regions (binned into 50 equally sized windows). Bins with coverage below 3 reads were ignored.
Figure 23A:
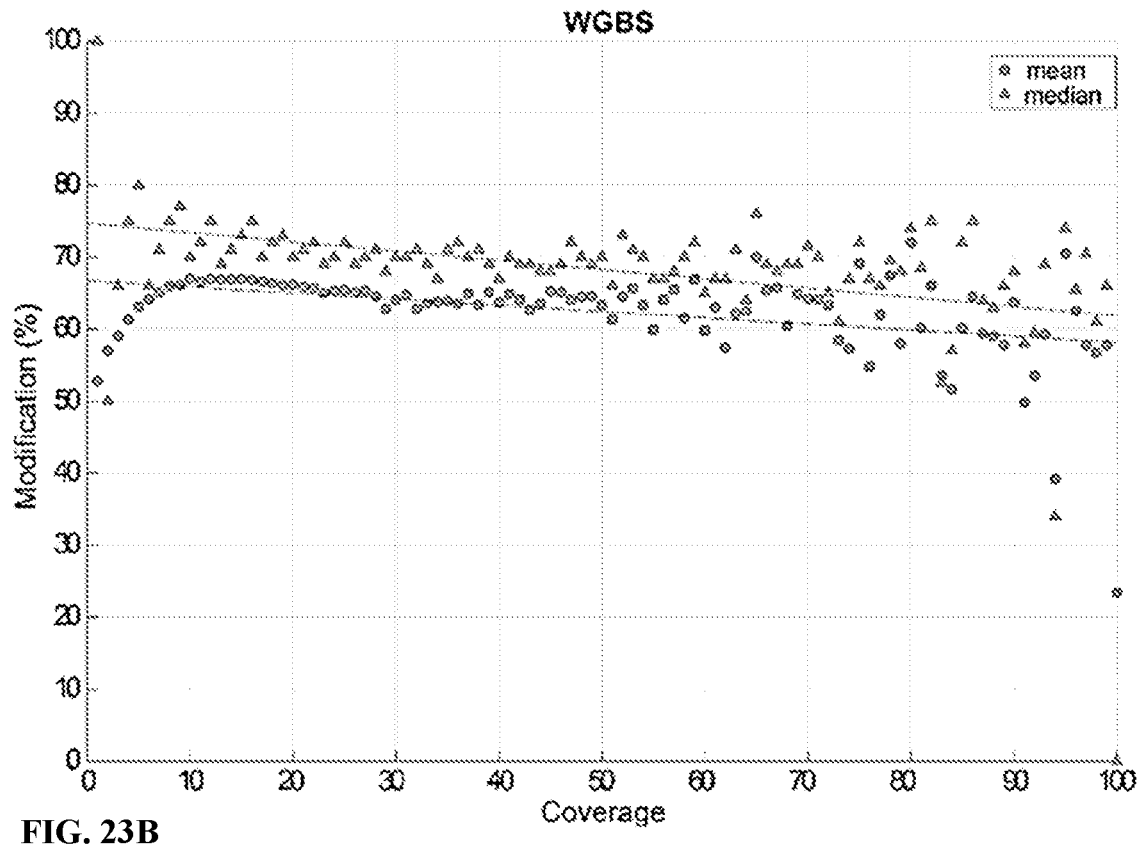
FIG. 23A-B. TAPS exhibits smaller coverage-modification bias than WGBS. All CpG sites were binned according to their coverage and the mean (circles) and the median (triangles) modification value is shown in each bin for WGBS (A) and TAPS (B). The CpG sites covered by more than 100 reads are shown in the last bin. The lines represent a linear fit through the data points.
Figure 23B:
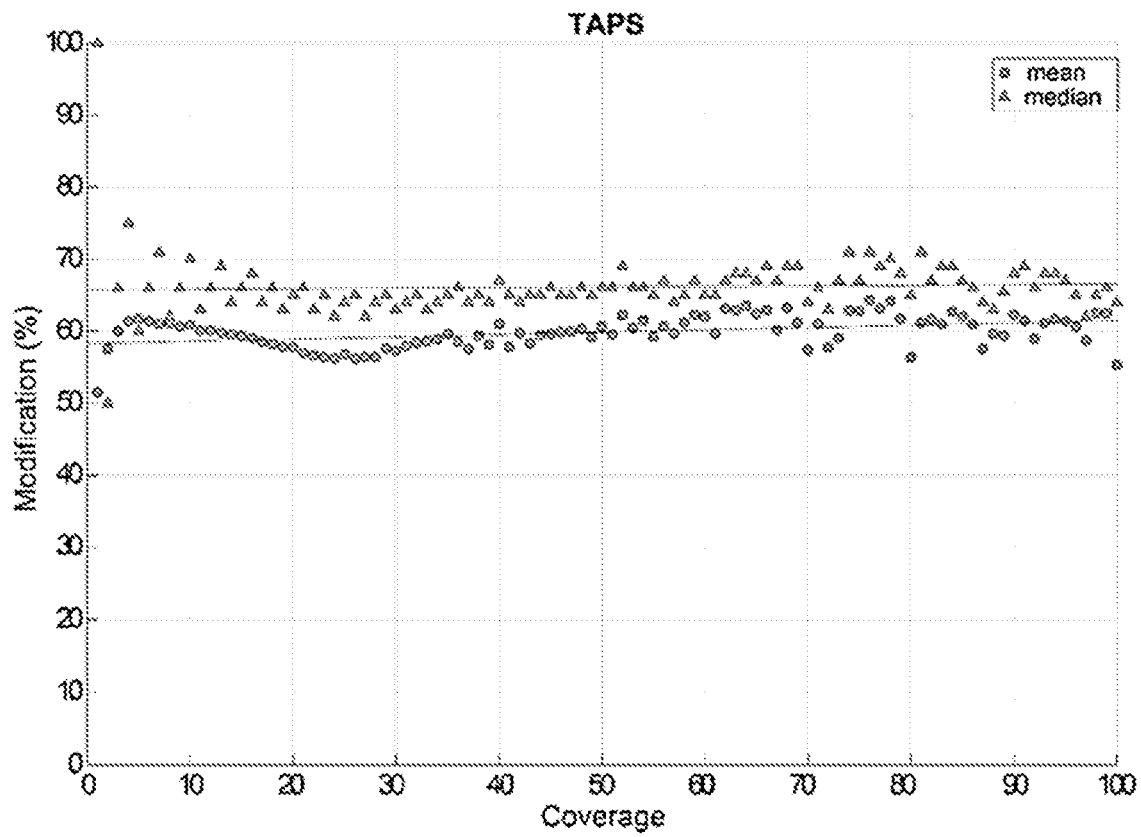
Figure 24A:
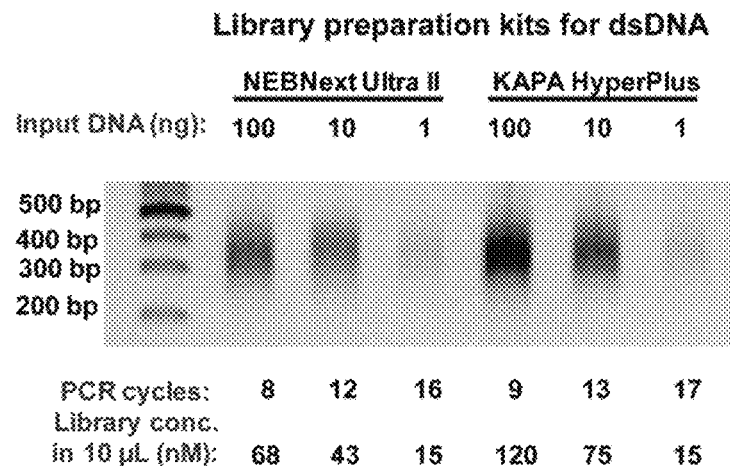
FIG. 24A-C. Low-input gDNA and cell-free DNA TAPS prepared with dsDNA and ssDNA library preparation kits. (A) Sequencing libraries were successfully constructed with down to 1 ng of murine embryonic stem cell (mESC) genomic DNA (gDNA) with dsDNA library kits NEBNext Ultra II or KAPA Hyperplus kits. ssDNA library kit Accel-NGS Methyl-Seq kit was used to further lower the input DNA amount down to (B) 0.01 ng of mESC gDNA or (C) 1 ng of cell-free DNA.
Figure 24B:
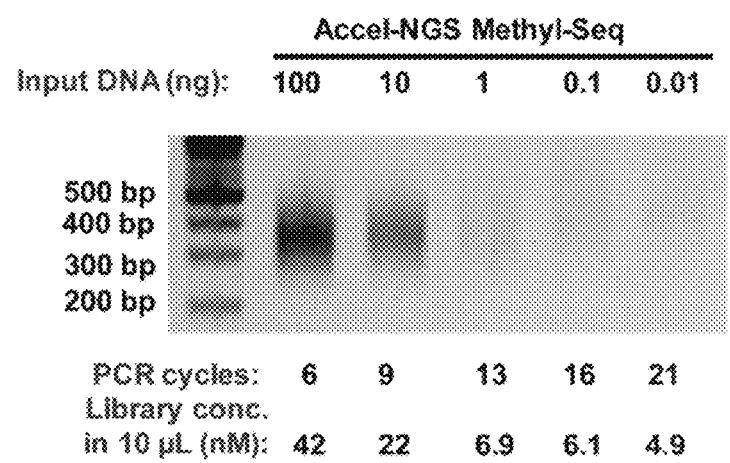
Figure 24C:
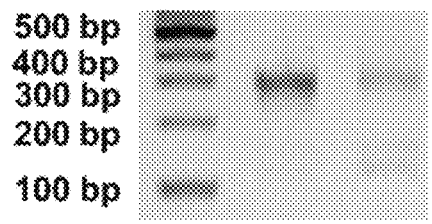
Figure 25A:
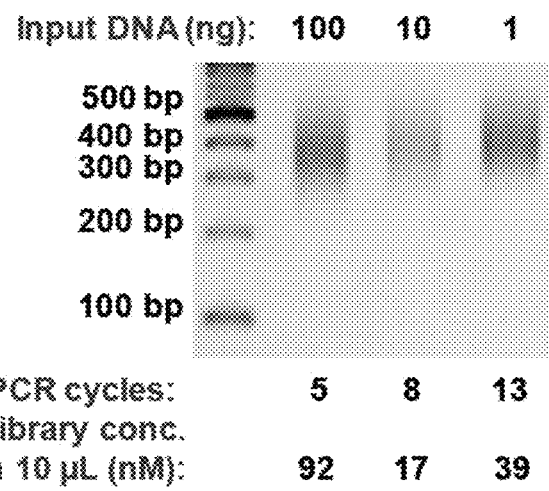
FIG. 25A-B. Low-input gDNA and cell-free DNA TAPS libraries prepared with dsDNA KAPA Hyperplus library preparation kit. Sequencing libraries were successfully constructed with as little as 1 ng of (A) mESC gDNA and (B) cell-free DNA with KAPA Hyperplus kit. Cell-free DNA has a sharp length distribution around 160 bp (nucleosome size)
Figure 25B:
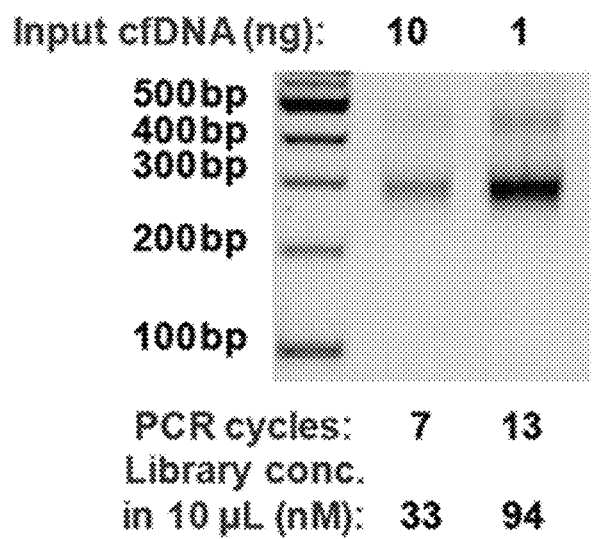

For example, CpG Islands (CGIs) in particular were generally better covered by TAPS, even when controlling for differences in sequencing depth between WGBS and TAPS (FIG. 21A), while both showed equivalent demethylation inside CGIs (FIG. 22). Moreover, WGBS showed a slight bias of decreased modification levels in highly covered CpG sites (FIG. 23A), while our results suggest that TAPS exhibits very little of the modification-coverage bias (FIG. 23B). These results demonstrate that TAPS dramatically improved sequencing quality compared to WGBS, while effectively halving the sequencing cost.

Figure 20:
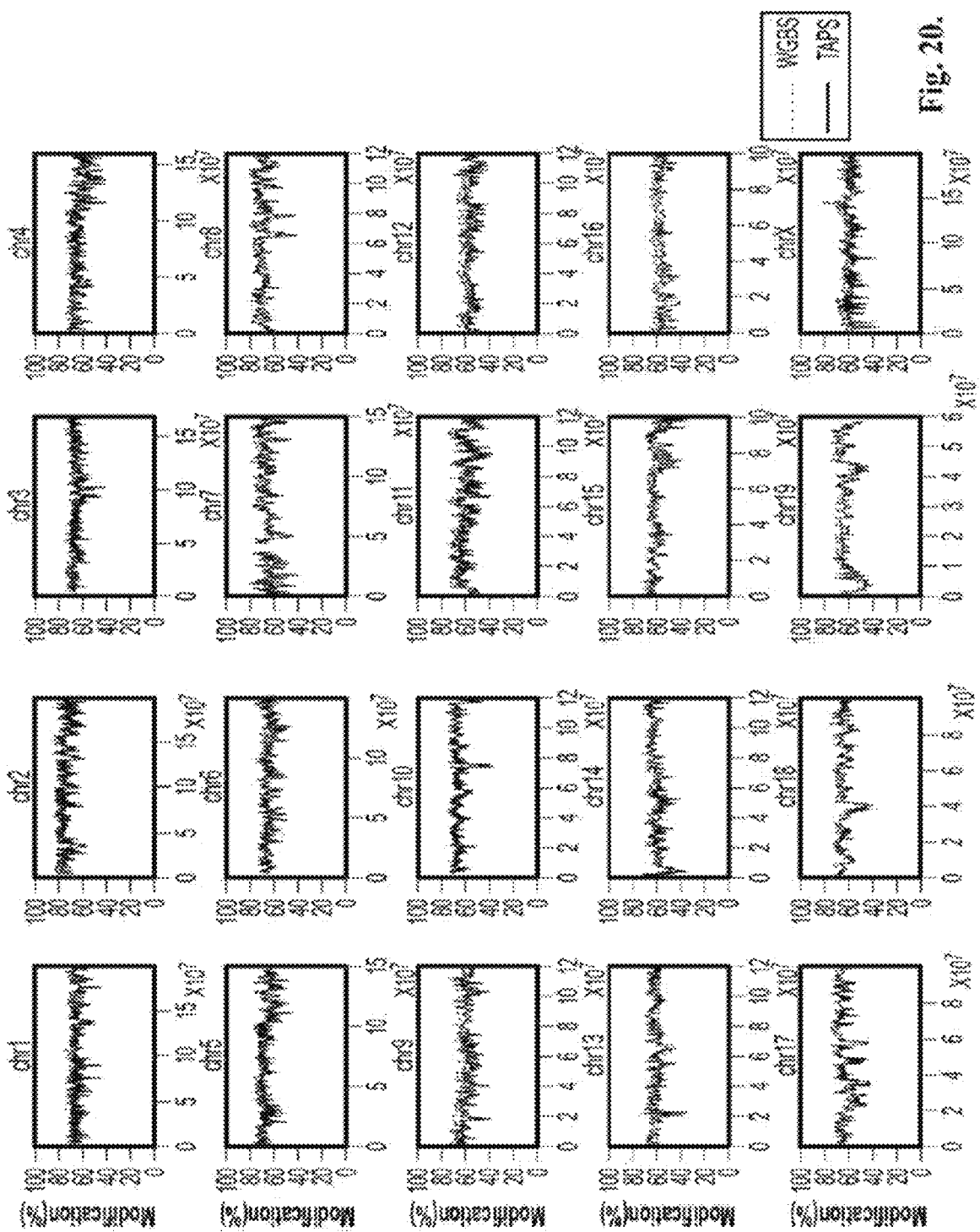
FIG. 20. Distribution of modification levels across all chromosomes. Average modification levels in 100 kb windows along mouse chromosomes, weighted by the coverage of CpG, and smoothed using a Gaussian weighted moving average filter with window size 10.
Figure 21B:
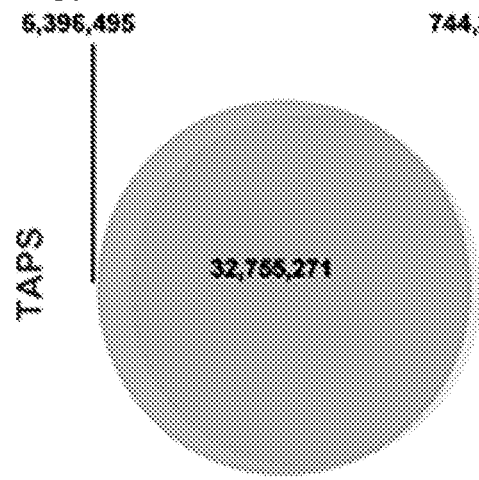
Figure 21C:
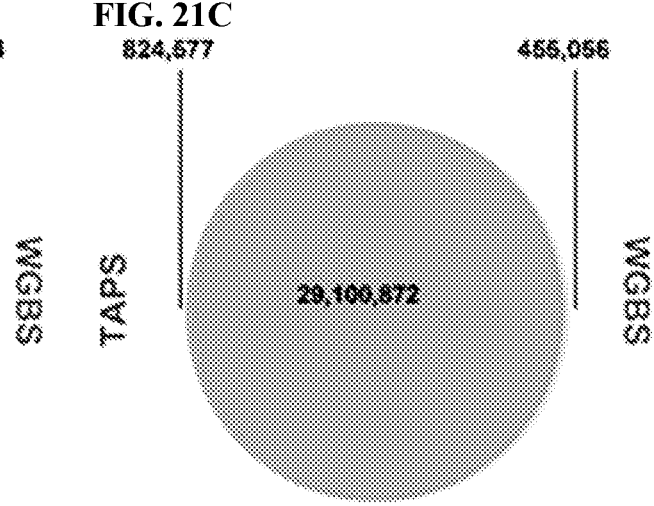
Figure 21D:
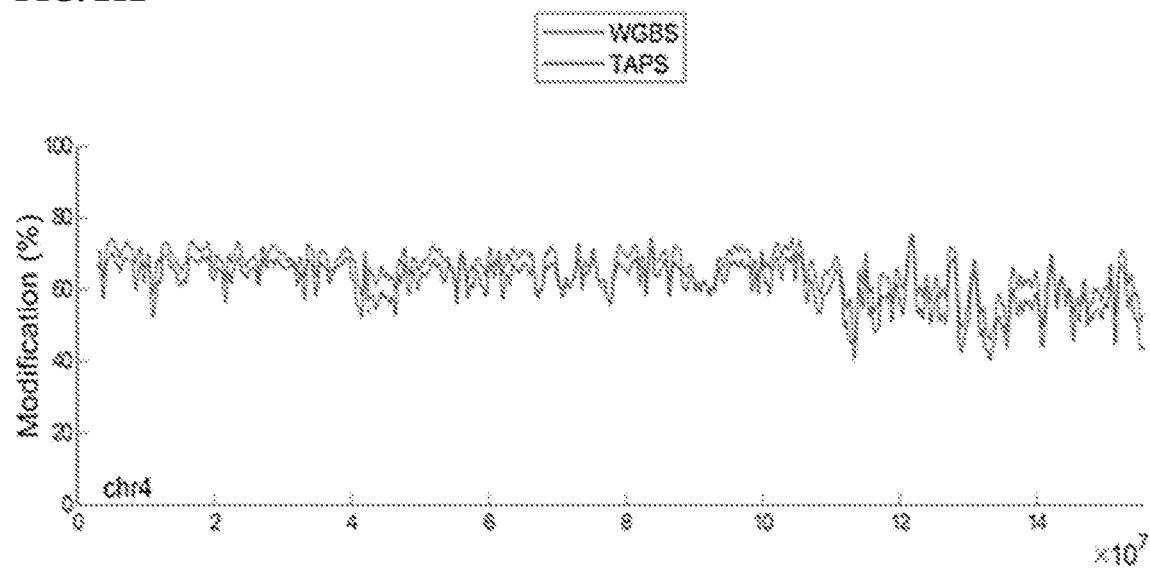
Figure 21E:
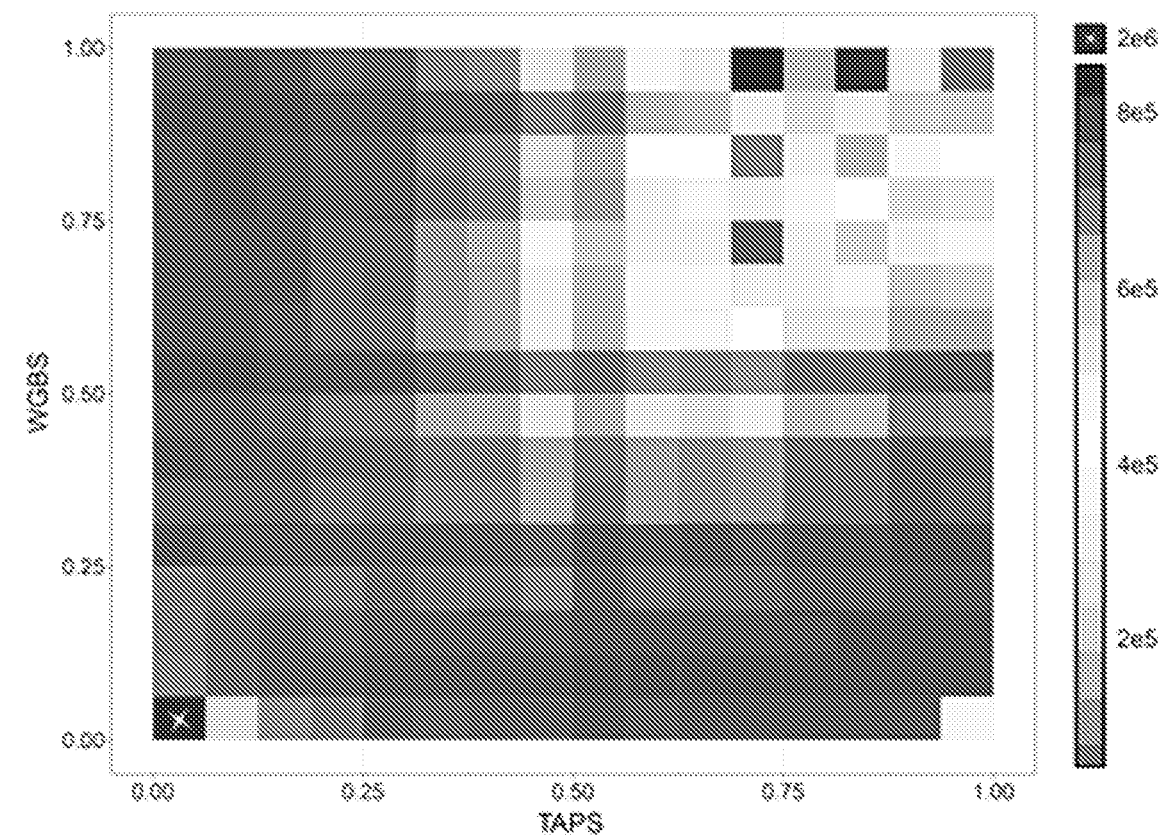

The higher and more even genome coverage of TAPS resulted in a larger number of CpG sites covered by at least three reads. With TAPS, 88.3% of all 43,205,316 CpG sites in the mouse genome were covered at this level, compared to only 77.5% with WGBS (FIGS. 21B and 19B). TAPS and WGBS resulted in highly correlated methylation measurements across chromosomal regions (FIG. 21D and FIG. 20). On a per-nucleotide basis, 32,755,271 CpG positions were covered by at least three reads in both methods (FIG. 21B). Within these sites, we defined "modified CpGs" as all CpG positions with a modification level of at least 10% (L. Wen et al., Whole-genome analysis of 5-hydroxymethylcytosine and 5-methylcytosine at base resolution in the human brain. Genome Biology 15, R49 (2014)). Using this threshold, 95.8% of CpGs showed matching modification states between TAPS and WGBS. 98.5% of all CpGs that were covered by at least three reads and found modified in WGBS were recalled as modified by TAPS, indicating good agreement between WGBS and TAPS (FIG. 21C). When comparing modification levels per each CpG covered by at least three reads in both WGBS and TAPS, good correlation between TAPS and WGBS was observed (Pearson r=0.63, p<2e-16, FIG. 21E). Notably, TAPS identified a subset of highly modified CpG positions which were missed by WGBS (FIG. 21E, bottom right corner). We further validated 7 of these CpGs, using an orthogonal restriction digestion and real-time PCR assay, and confirmed all of them are fully methylated and/or hydroxymethylated (Table 9).

TABLE 9

Comparison of CmCGG methylation level in mESC gDNA quantified by TAPS, WGBS and HpaII-qPCR assay. Coverage and methylation level ($^mC$ %) by TAPS and WGBS were computed for per strand. Ct value for HpaII digested sample ($Ct_{HpaII}$) or control sample ($Ct_{ctrl}$) in the HpaII-qPCR assay was average of triplicates. $^mC$ % is calculated using following equation: $^mC\ \% = 2^{\wedge}(Ct_{ctrl} - Ct_{HpaII})\ 100\%$.

| | TAPS | | WGBS | | HpaII-qPCR assay | | | |
|---|---|---|---|---|---|---|---|---|
| Position of $C^mCGG$ | Coverage | $^mC$ % | Coverage | $^mC$ % | $Ct_{HpaII}$ | $Ct_{Ctrl}$ | $^mC$ % | Forward and reverse primer (5'-3') |
| chr6: 135868201 | 17 | 100% | 11 | 0% | 29.628 | 29.642 | 101.0% | GCTGCAGATTGGAGCC AAAG TTGATGGTGATGGTGG AGCC (SEQ ID NO: 45) |

TABLE 9-continued

Comparison of CmCGG methylation level in mESC gDNA quantified by TAPS, WGBS and HpaII-qPCR assay. Coverage and methylation level ($^mC$ %) by TAPS and WGBS were computed for per strand. Ct value for HpaII digested sample ($Ct_{HpaII}$) or control sample ($Ct_{Ctrl}$) in the HpaII-qPCR assay was average of triplicates. $^mC$ % is calculated using following equation: $^mC\ \% = 2^{\wedge}(Ct_{Ctrl} - Ct_{HpaII})\ 100\%$.

| | TAPS | | WGBS | | HpaII-qPCR assay | | | Forward and reverse primer (5'-3') |
|---|---|---|---|---|---|---|---|---|
| Position of $C^mCGG$ | Coverage | $^mC$ % | Coverage | $^mC$ % | $Ct_{HpaII}$ | $Ct_{Ctrl}$ | $^mC$ % | |
| chr3: 31339449 | 15 | 100% | 10 | 0% | 22.162 | 22.111 | 96.5% | TCAGTGCTCATGGACTC ATACT ATACCCTGGGAGCAAA GTTGTTG (SEQ ID NO: 46) |
| chr4: 128271030 | 12 | 100% | 10 | 0% | 31.304 | 31.279 | 98.3% | CCCACTAGACATGCTCT GCC CAAAATGTTGCTTGCCT TCCG (SEQ ID NO: 47) |
| chr1: 58635199 | 11 | 100% | 8 | 0% | 22.008 | 22.026 | 101.3% | TCCCTGAGCCCTGATCT AGT AATACTGGCTGACCGG TTCT (SEQ ID NO: 48) |
| chr14: 36331351 | 11 | 100% | 14 | 0% | 21.228 | 21.053 | 88.6% | ACACCACAGCAGAAGA GAGC TAGGATTGTTGCACAG GCCA (SEQ ID NO: 49) |
| chr19: 42893499 | 11 | 100% | 18 | 0% | 22.515 | 22.558 | 103.0% | GCTGAGCTGTATCCTTG AGGT ACACGTGGGTATTCCA CAGC (SEQ ID NO: 50) |
| chr3: 113611193 | 10 | 100% | 5 | 0% | 22.439 | 22.545 | 107.6% | GTGGATCTTCAGTGGTG GCA ATGCTCCCTCATCCTTT GCA (SEQ ID NO: 51) |
| Negative CCGG site | | | | | | | | |
| chr19: 9043049 | 25 | 0% | 17 | 0% | 27.11 | 21.409 | 1.9% | AGCCTCTGAACTTGACT GCC GCCTGGAACTCCTGAC AGTC (SEQ ID NO: 52) |
| Positive CCGG site | | | | | | | | |
| chr15: 39335961 | 16 | 100% | 4 | 100% | 22.163 | 22.248 | 106.1% | GGTCCTTGATCCACCCA GAC ACATGGTGCTGGTCTA ACCG (SEQ ID NO: 53) |

Together, these results indicate that TAPS can directly replace WGBS, and in fact provides a more comprehensive view of the methylome than WGBS.

Finally, TAPS was tested with low input DNA and TAPS was shown to work with as little as 1 ng gDNA and in some instances down to 10 pg of gDNA, close to single-cell level. TAPS also works effectively with down to 1 ng of circulating cell-free DNA. These results demonstrate the potential of TAPS for low input DNA and clinical applications (FIG. 24A-C, FIG. 25A-B).

Figure 26A:
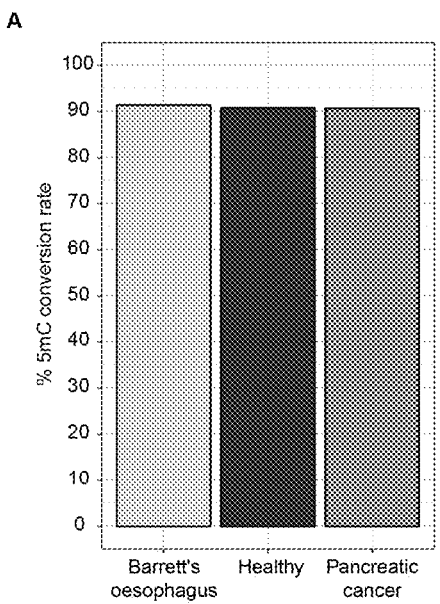
Figure 26B:
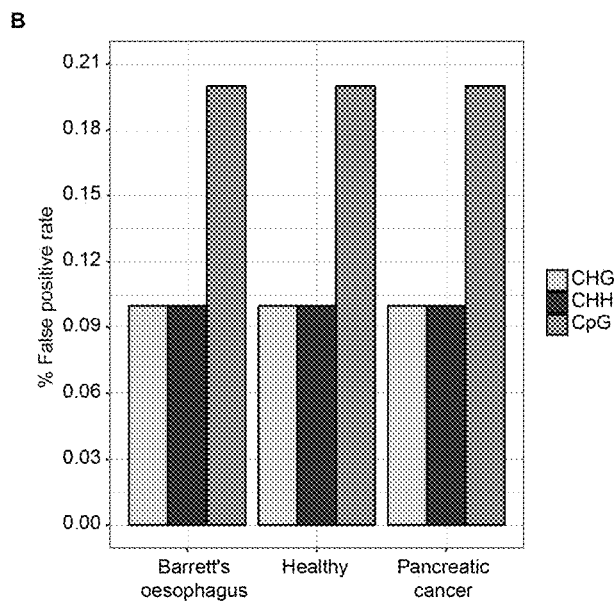
Figure 26C:
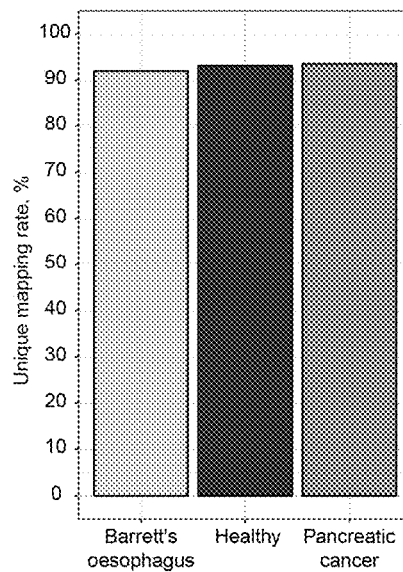
Figure 26D:
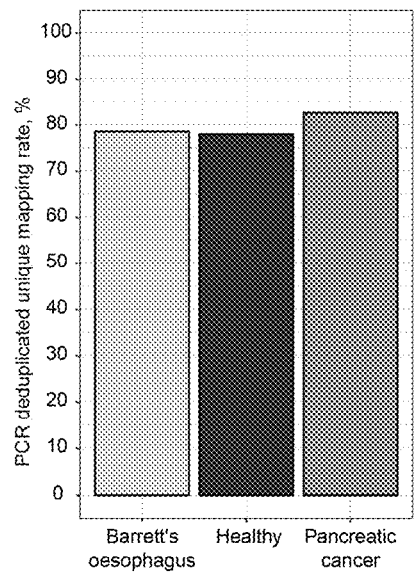

TAPS was tested on three circulating cell-free DNA samples (cfDNA) from one healthy sample, one Barrett's oesophagus (Barrett's) sample, and one pancreatic cancer sample that were obtained from 1-2 ml of plasma. Standard TAPS protocol was followed and each sample sequenced to ~10× coverage. Analysis of the cfDNA TAPS results showed that TAPS provided the same high-quality methylome sequencing from low-input cfDNA as from bulk genomic DNA, including high 5mC conversion rate (FIG. 26A), low false positive rate (conversion of unmodified cytosine, FIG. 26B), high mapping rate (FIG. 26C), and low PCR duplication rate (FIG. 26D). These results demonstrate the power of TAPS for disease diagnostics from cfDNA.

TAPS can also differentiate methylation from C-to-T genetic variants or single nucleotide polymorphisms (SNPs), therefore could detect genetic variants. Methylations and C-to-T SNPs result in different patterns in TAPS: methylations result in T/G reads in original top strand (OT)/original bottom strand (OB) and A/C reads in strands complementary to OT (CTOT) and OB (CTOB), whereas C-to-T SNPs result in T/A reads in OT/OB and (CTOB/CTOT) (FIG. 27). This further increases the utility of TAPS in providing both methylation information and genetic variants, and therefore mutations, in one experiment and sequencing run. This ability of the TAPS method disclosed herein provides integration of genomic analysis with epigenetic analysis, and a substantial reduction of sequencing cost by eliminating the need to perform standard whole genome sequencing (WGS). In summary, we have developed a series of PS-derived bisulfite-free, base-resolution sequencing methods for cytosine epigenetic modifications and demonstrated the utility of TAPS for whole-methylome sequencing. By using mild enzymatic and chemical reactions to detect 5mC and 5hmC directly at base-resolution with high sensitivity and specificity without affecting unmodified cytosines, TAPS outperforms bisulfite sequencing in providing a high quality and more complete methylome at half the sequencing cost. As such TAPS could replace bisulfite sequencing as the new standard in DNA methylcytosine and hydroxymethylcytosine analysis. Rather than introducing a bulky modification on cytosines in the bisulfite-free 5fC sequencing method reported recently (B. Xia et al., Bisulfite-free, base-resolution analysis of 5-formylcytosine at the genome scale. *Nat. Methods* 12, 1047-1050 (2015); C. Zhu et al., Single-Cell 5-Formylcytosine Landscapes of Mammalian Early Embryos and ESCs at Single-Base Resolution. *Cell Stem Cell* 20, 720-731 (2017)), TAPS converts modified cytosine into DHU, a near natural base, which can be "read" as T by common polymerases and is potentially compatible with PCR-free DNA sequencing. TAPS is compatible with a variety of downstream analyses, including but not limit to, pyrosequencing, methylation-sensitive PCR, restriction digestion, MALDI mass spectrometry, microarray and whole-genome sequencing. Since TAPS can preserve long DNA, it can be extremely valuable when combined with long read sequencing technologies, such as SMRT sequencing and nanopore sequencing, to investigate certain difficult to map regions. It is also possible to combine pull-down methods with TAPS to further reduce the sequencing cost and add base-resolution information to the low-resolution affinity-based maps. Herein, it was demonstrated that TAPS could directly replace WGBS in routine use while reducing cost, complexity and time required for analysis. This could lead to wider adoption of epigenetic analyses in academic research and clinical diagnostics.

The invention claimed is:

1. A method for identifying 5-methylcytosine (5mC) or 5-hydroxymethylcytosine (5hmC) in a target nucleic acid comprising the steps of:
   providing a nucleic acid sample comprising the target nucleic acid;
   modifying the target nucleic acid comprising the steps of:
      converting the 5mC and 5hmC in the nucleic acid sample to 5-carboxylcytosine (5caC) and/or 5-formylcytosine (5fC) by contacting the nucleic acid sample with a ten-eleven translocation (TET) enzyme so that one or more 5caC or 5fC residues are generated; and
      converting the 5caC and/or 5fC to dihydrouracil (DHU) by treating the target nucleic acid with a borane reducing agent to provide a modified nucleic acid sample comprising a modified target nucleic acid; and
   detecting the sequence of the modified target nucleic acid;
   wherein a cytosine (C) to thymine (T) transition or a cytosine (C) to DHU transition in the sequence of the modified target nucleic acid compared to the target nucleic acid provides the location of either a 5mC or 5hmC in the target nucleic acid.

2. The method of claim 1, wherein the borane reducing agent is 2-picoline borane.

3. The method of claim 1, wherein the step of detecting the sequence of the modified target nucleic acid comprises one or more of chain termination sequencing, microarray, high-throughput sequencing, and restriction enzyme analysis.

4. The method of claim 1, wherein the TET enzyme is selected from the group consisting of human TET1, TET2, and TET3; murine Tet1, Tet2, and Tet3; *Naegleria* TET (NgTET); and *Coprinopsis cinerea* (CcTET).

5. The method of claim 1, further comprising a step of blocking one or more modified cytosines.

6. The method of claim 5, wherein the step of blocking comprises adding a sugar to a 5hmC.

7. The method of claim 1, wherein the method further comprises a step of amplifying the copy number of one or more nucleic acid sequences.

8. A method for chemically modifying a nucleic acid sample comprising the steps of:
   providing a nucleic acid sample comprising 5-carboxylcytosine (5caC) and/or 5-formylcytosine (5fC); and
   converting the 5caC and/or 5fC to dihydrouracil (DHU) by treating the nucleic acid with a borane reducing agent to provide a modified nucleic acid sample comprising a modified nucleic acid.

9. The method of claim 8, wherein the borane reducing agent is selected from the group consisting of 2-picoline borane (pic-BH3), borane, sodium borohydride, sodium cyanoborohydride, and sodium triacetoxyborohydride.

10. The method of claim 8, wherein the borane reducing agent is 2-picoline borane.

11. The method of claim 8, further comprising the step of detecting the sequence of the modified nucleic acid.

12. The method of claim 11, wherein the step of detecting the sequence of the modified nucleic acid comprises one or more of chain termination sequencing, microarray, high-throughput sequencing, and restriction enzyme analysis.

13. The method of claim 11, wherein the sequencing step provides a quantitative level of one or more cytosine modifications in the nucleic acid sample.

14. The method of claim 8, wherein the method further comprises a step of amplifying the copy number of one or more nucleic acid sequences.

* * * * *